US011015229B2

(12) United States Patent
Tarcic et al.

(10) Patent No.: US 11,015,229 B2
(45) Date of Patent: *May 25, 2021

(54) METHODS AND SYSTEMS FOR DETERMINING ONCOGENIC INDEX OF PATIENT SPECIFIC MUTATIONS

(71) Applicant: NOVELLUSDX LTD., Jerusalem (IL)

(72) Inventors: Gabi Tarcic, Mevasseret Zion (IL); Yoram Altschuler, Mevasseret Zion (IL); Michael Vidne, Caesarea (IL)

(73) Assignee: NOVELLUSDX LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,505

(22) PCT Filed: Jul. 20, 2015

(86) PCT No.: PCT/IL2015/050747
§ 371 (c)(1),
(2) Date: Jan. 19, 2017

(87) PCT Pub. No.: WO2016/013008
PCT Pub. Date: Jan. 28, 2016

(65) Prior Publication Data
US 2017/0159138 A1  Jun. 8, 2017

Related U.S. Application Data

(60) Provisional application No. 62/026,716, filed on Jul. 21, 2014.

(51) Int. Cl.
C12Q 1/68     (2018.01)
C12Q 1/6897   (2018.01)
C12Q 1/6886   (2018.01)

(52) U.S. Cl.
CPC ......... *C12Q 1/6897* (2013.01); *C12Q 1/6886* (2013.01); *C07K 2319/09* (2013.01); *C07K 2319/60* (2013.01); *C12Q 2563/107* (2013.01); *C12Q 2565/501* (2013.01); *C12Q 2600/106* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman |
| 4,034,074 A | 7/1977 | Miles |
| 4,098,876 A | 7/1978 | Piasio |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands |
| 5,011,771 A | 4/1991 | Bellet |
| 5,192,659 A | 3/1993 | Simons |
| 5,272,057 A | 12/1993 | Smulson |
| 5,281,521 A | 1/1994 | Trojanowski |
| 2006/0148715 A1 | 7/2006 | Tweardy |

FOREIGN PATENT DOCUMENTS

| | | |
|---|---|---|
| CN | 1496268 A | 5/2004 |
| CN | 103038643 A | 4/2013 |
| WO | 2004009847 | 1/2004 |
| WO | 2011/130654 A1 | 10/2011 |
| WO | 2014111936 | 4/2014 |

OTHER PUBLICATIONS

Yoshikawa et al (Journal of Controlled Release, 2004. vol. 96, pp. 227-232).*
Morris et al., "Recurrent somatic mutation of FAT1 in multiple human cancers leads to aberrant Wnt activation", Nat Genet, Mar. 2013, 45(3): 253-261; 24 pages.
Extended European Search Report dated Jan. 22, 2016 issued in corresponding EP Application No. 15825517.4; 6 pages.
Office Action dated Nov. 5, 2018 issued in corresponding CN Application No. 2015800507343; 6 pages.
Cardarella et al., (2013) Clinical, pathologic, and biologic features associated with BRAF mutations in non-small cell lung cancer. Clinical Cancer Research, 19(16), 4532-4540.
Chiu et al., (2015) Epidermal growth factor receptor tyrosine kinase inhibitor treatment response in advanced lung adenocarcinomas with G719X/L861Q/S768I mutations. Journal of Thoracic Oncology, 10(5), 793-799.
Kau et al., (2004) Nuclear transport and cancer: from mechanism to intervention. Nature Reviews Cancer, 4(2), 106-117US 2006148715.
Leonardzehr. In conversation with Michael Vidne, BioTuesdays, [Retrieved on Jun. 12, 2016]. Retrieved from the internet: http://www.biotuesdays.com/features/2014/2/11/in-conversation-with-michael-vidne?rq=in%20conversation%20with%20michael Feb. 11, 2014; 4 pages.
Rosell et al., (2012) Erlotinib versus standard chemotherapy as first-line treatment for European patients with advanced EGFR mutation-positive non-small-cell lung cancer (EURTAC): a multicentre, open-label, randomised phase 3 trial. The lancet oncology, 13(3), 239-246.
Vogelstein et al., (2013) Cancer genome landscapes. science, 339(6127), 1546-1558.
International Search Report based on International Patent Application No. PCT/IL2015/050747, dated Nov. 3, 2015.

* cited by examiner

Primary Examiner — Celine X Qian
(74) Attorney, Agent, or Firm — J.A. Lindeman & Co., PLLC

(57) ABSTRACT

Methods for determining various oncogenic-related indexes of patient specific mutations are provided. The methods provided allow determination and grading of various patient specific mutations and qualitative and quantitative determination of various related oncogenic indexes.

6 Claims, 14 Drawing Sheets

Specification includes a Sequence Listing.

Graded increase in subcellular translocation of ERK2 is correlated to the gravity of the BRAF oncogenic mutation Graded increase in subcellular translocation of AKT1 is correlated to the gravity of the EGFR oncogenic mutation Differential increase in subcellular translocation of JNK1a1 is correlated to the gravity of the EGFR oncogenic mutation Differential subcellular translocation of JNK2, ERK2 or STAT3 in response to expression of different EGFR mutants Differential subcellular translocation of JNK2, ERK2, STAT3 or P38 in response to expression of different ERBB2 mutants Differential subcellular translocation of JNK2, ERK2, STAT3, REL-A or P38 in response to expression of different cKIT mutants Differential subcellular translocation of JNK2, ERK2, FOXO3a or NFkB in response to expression of different KRAS mutants Differential subcellular translocation of KOG1, P38, STAT3 or REL-A in response to expression of different PIK3CA mutants Oncogenic map Differential subcellular translocation of JNK2, ERK2 or REL-A in response to expression of different BRAF mutants Differential subcellular translocation of ERK2 in response to expression of different EGFR or KRAS mutants or their combinations Differential subcellular translocation of RelA in response to expression of different EGFR or KRAS mutants or their combinations Differential subcellular translocation of JNK in response to expression of different EGFR or KRAS mutants or their combinations Differential subcellular translocation of ERK2 in response to
expression of different ERBB2 or BRAF mutants or their combinations

SEQUENCE LISTING

<160> NUMBER OF SEQ ID NOS: 47

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
atgagcgacg tggctattgt					20

<210> SEQ ID NO 2
<211> LENGTH: 18
<212> TYPE: DNA
<213> ORGANISM: Artificial sequence
<220> FEATURE:
<223> OTHER INFORMATION: Primer

<400> SEQUENCE: 2
tcaggccgtg ccgctggc					18

<210> SEQ ID NO 3
<211> LENGTH: 19
<212> TYPE: DNA
<213> ORGANISM: Artificial sequence
<220> FEATURE:
<223> OTHER INFORMATION: Primer

<400> SEQUENCE: 3
atggcggcgc tgagcggtg					19

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tcagtggaca ggaaacgcac					20

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
atgcgaccct ccgggacg					18

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
tcatgctcca ataaattcac tgct					24

<210> SEQ ID NO 7
<211> LENGTH: 23
<212> TYPE: DNA
<213> ORGANISM: Artificial sequence

```
<220> FEATURE:
<223> OTHER INFORMATION: Primer

<400> SEQUENCE: 7
atgacggaat ataagctggt ggt                                    23

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
tcaggagagc acacacttgc                                        20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
atgcccaaga agaagccgac                                        20

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
ttagacgcca gcagcatgg                                         19

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
atgactgagt acaaactggt ggt                                    23

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ttacatcacc acacatggca                                        20

<210> SEQ ID NO 13
<211> LENGTH: 19
<212> TYPE: DNA
<213> ORGANISM: Artificial sequence
<220> FEATURE:
<223> OTHER INFORMATION: Primer

<400> SEQUENCE: 13
atggggactt cccatccgg                                         19
```

```
<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
ttacaggaag ctgtcttcca cc                                              22

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
atgcctccac gaccatcatc                                                 20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
tcagttcaat gcatgctgtt                                                 20

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
atgacagcca tcatcaaaga ga                                              22

<210> SEQ ID NO 18
<211> LENGTH: 25
<212> TYPE: DNA
<213> ORGANISM: Artificial sequence
<220> FEATURE:
<223> OTHER INFORMATION: Primer

<400> SEQUENCE: 18
tcagactttt gtaatttgtg tatgc                                           25

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
atggagcaca tacagggagc                                                 20

<210> SEQ ID NO 20
<211> LENGTH: 20
<212> TYPE: DNA
<213> ORGANISM: Artificial sequence
<220> FEATURE:
<223> OTHER INFORMATION: Primer
```

```
<400> SEQUENCE: 20
ctagaagaca ggcagcctcg                                          20

<210> SEQ ID NO 21
<211> LENGTH: 18
<212> TYPE: DNA
<213> ORGANISM: Artificial sequence
<220> FEATURE:
<223> OTHER INFORMATION: Primer

<400> SEQUENCE: 21
atggaggagc cgcagtca                                            18

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
tcagtctgag tcaggcccttt                                         20

<210> SEQ ID NO 23
<211> LENGTH: 25
<212> TYPE: DNA
<213> ORGANISM: Artificial sequence
<220> FEATURE:
<223> OTHER INFORMATION: Primer

<400> SEQUENCE: 23
atgaatgagg tgtctgtcat caaag                                    25

<210> SEQ ID NO 24
<211> LENGTH: 17
<212> TYPE: DNA
<213> ORGANISM: Artificial sequence
<220> FEATURE:
<223> OTHER INFORMATION: Primer

<400> SEQUENCE: 24
tcactcgcgg atgctgg                                             17

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
atgagcgatg ttaccattgt g                                        21

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
ttattctcgt ccacttgcag ag                                       22
```

```
<210> SEQ ID NO 27
<211> LENGTH: 18
<212> TYPE: DNA
<213> ORGANISM: Artificial sequence
<220> FEATURE:
<223> OTHER INFORMATION: Primer

<400> SEQUENCE: 27
atgtggagct ggaagtgc                                                 18

<210> SEQ ID NO 28
<211> LENGTH: 17
<212> TYPE: DNA
<213> ORGANISM: Artificial sequence
<220> FEATURE:
<223> OTHER INFORMATION: Primer

<400> SEQUENCE: 28
tcagcggcgt ttgagtc                                                  17

<210> SEQ ID NO 29
<211> LENGTH: 17
<212> TYPE: DNA
<213> ORGANISM: Artificial sequence
<220> FEATURE:
<223> OTHER INFORMATION: Primer

<400> SEQUENCE: 29
atggtcagct ggggtcg                                                  17

<210> SEQ ID NO 30
<211> LENGTH: 25
<212> TYPE: DNA
<213> ORGANISM: Artificial sequence
<220> FEATURE:
<223> OTHER INFORMATION: Primer

<400> SEQUENCE: 30
tcatgtttta acactgccgt ttatg                                         25

<210> SEQ ID NO 31
<211> LENGTH: 27
<212> TYPE: DNA
<213> ORGANISM: Artificial sequence
<220> FEATURE:
<223> OTHER INFORMATION: Primer

<400> SEQUENCE: 31
gcctgctgaa aatgactgaa tataaac                                       27

<210> SEQ ID NO 32
<211> LENGTH: 31
<212> TYPE: DNA
<213> ORGANISM: Artificial sequence
<220> FEATURE:
<223> OTHER INFORMATION: Primer

<400> SEQUENCE: 32
ttacataatt acacactttg tctttgactt c                                  31

<210> SEQ ID NO 33
<211> LENGTH: 21
<212> TYPE: DNA
<213> ORGANISM: Artificial sequence
<220> FEATURE:
<223> OTHER INFORMATION: Primer
```

```
<400> SEQUENCE: 33
atgtcgtcca tcttgccatt c                                              21

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
ttatgacatg cttgagcaac g                                              21

<210> SEQ ID NO 35
<211> LENGTH: 16
<212> TYPE: DNA
<213> ORGANISM: Artificial sequence
<220> FEATURE:
<223> OTHER INFORMATION: Primer

<400> SEQUENCE: 35
atggcggcgg cggcgg                                                    16

<210> SEQ ID NO 36
<211> LENGTH: 18
<212> TYPE: DNA
<213> ORGANISM: Artificial sequence
<220> FEATURE:
<223> OTHER INFORMATION: Primer

<400> SEQUENCE: 36
ttaagatctg tatcctgg                                                  18

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
atgaagaccc cggcggacac                                                20

<210> SEQ ID NO 38
<211> LENGTH: 19
<212> TYPE: DNA
<213> ORGANISM: Artificial sequence
<220> FEATURE:
<223> OTHER INFORMATION: Primer

<400> SEQUENCE: 38
tcaggagtct cggtgctcc                                                 19

<210> SEQ ID NO 39
<211> LENGTH: 17
<212> TYPE: DNA
<213> ORGANISM: Artificial sequence
<220> FEATURE:
<223> OTHER INFORMATION: Primer

<400> SEQUENCE: 39
atgagcagaa gcaagcg                                                   17
```

```
<210> SEQ ID NO 40
<211> LENGTH: 18
<212> TYPE: DNA
<213> ORGANISM: Artificial sequence
<220> FEATURE:
<223> OTHER INFORMATION: Primer

<400> SEQUENCE: 40
tcactgctgc acctgtgc                                                 18

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
atggacgaac tgttccccct                                               20

<210> SEQ ID NO 42
<211> LENGTH: 21
<212> TYPE: DNA
<213> ORGANISM: Artificial sequence
<220> FEATURE:
<223> OTHER INFORMATION: Primer

<400> SEQUENCE: 42
taggagctga tctgactcag c                                             21

<210> SEQ ID NO 43
<211> LENGTH: 14
<212> TYPE: DNA
<213> ORGANISM: Artificial sequence
<220> FEATURE:
<223> OTHER INFORMATION: Primer

<400> SEQUENCE: 43
atgtcgggcc ctcg                                                     14

<210> SEQ ID NO 44
<211> LENGTH: 20
<212> TYPE: DNA
<213> ORGANISM: Artificial sequence
<220> FEATURE:
<223> OTHER INFORMATION: Primer

<400> SEQUENCE: 44
tcactgctca atctccaggc                                               20

<210> SEQ ID NO 45
<211> LENGTH: 18
<212> TYPE: DNA
<213> ORGANISM: Artificial sequence
<220> FEATURE:
<223> OTHER INFORMATION: Primer

<400> SEQUENCE: 45
atggcccaat ggaatcag                                                 18

<210> SEQ ID NO 46
<211> LENGTH: 18
<212> TYPE: DNA
<213> ORGANISM: Artificial sequence
<220> FEATURE:
<223> OTHER INFORMATION: Primer
```

```
<400> SEQUENCE: 46
tcacatgggg gaggtagc                                                18

<210> SEQ ID NO 47
<211> LENGTH: 6
<212> TYPE: PRT
<213> ORGANISM: Artificial sequence
<220> FEATURE:
<223> OTHER INFORMATION: Peptide

<400> SEQUENCE: 47

Cys Cys Pro Gly Cys Cys
1               5
```

METHODS AND SYSTEMS FOR DETERMINING ONCOGENIC INDEX OF PATIENT SPECIFIC MUTATIONS

CROSS REFERENCE TO RELATED APPLICATIONS

The present application is a U.S. National Stage of International Patent Application Serial No. PCT/IL2015/050747, filed Jul. 20, 2015, which claims priority to, and the benefit of U.S. Provisional Patent Application Ser. No. 60/026,716, filed on Jul. 21, 2014, each of which is herein incorporated by reference in its entirety for all purposes.

FIELD OF THE INVENTION

Methods and systems for determining various oncogenic-related indexes of patient specific mutation(s) are provided. The systems and methods allow determination and grading of various patient specific mutations as well as qualitative and quantitative determination of various related oncogenic indexes.

BACKGROUND OF THE INVENTION

Cancer (malignant tumor or malignant neoplasm), is a group of diseases involving abnormal cell growth with the potential to invade or spread to other body parts. Cancer are extremely diverse and various underlying molecular mechanism are involved therewith. Accordingly, prognosis of patients diagnosed with various cancers, may be drastically different depending on accurate diagnosis of underlying molecular mechanism, as well as, identification of the oncogenic mutations and auto and paracrine effects.

Further, the complexity and heterogeneity of cancer demands a more sensitive and discerning diagnostic approach that mirrors the patient specific tumor signaling pathway in a qualitative and quantitative manner and enables accurate grading the specific mutations for determining an accurate prognosis and optimized therapy. For example, international publication no. WO 2014/111936 to some of the inventors of the current application is directed to methods and systems for identifying patient specific driver mutations. Currently, the suitability of whole-genome sequencing (such as next generation sequencing) for providing accurate prognosis or optimized selection of targeted therapy is limited due to the large pool of mutations accumulating within the tumor, the limited repertoire of identified driver mutations and the very limited insight as to the interplay of the various mutations and, in particular, activity thereof.

Thus, there is unmet need in the art for methods and systems that provide a qualitative and quantitative grading of patient specific mutations and that can allow the determination of various related indexes that can provide a personalized indication of the specific mutations of the patient and that can further provide a patient specific prognosis and/or optimized treatment indications.

SUMMARY OF THE INVENTION

The present invention provides methods and systems for determining and/or calculating and/or generating various oncogenic indexes of patient specific mutation(s) that can provide an insight as to patient's mutations as well as to the specific condition of the patient (prognosis) and that can further aid in determining an optimized treatment. The patient specific mutations, are recognized by identifying changes in signaling pathway activity, which is associated with the function of the driver mutation, in a test cell. According to some embodiments, changes in the signaling pathway activity are determined by identifying changes in subcellular localization of a reporter gene, which is associated with the function of the patient mutation. In some embodiments, specific patient derived marker (PDM) genes are obtained or derived (directly or indirectly) from a biological sample, and their effect on the subcellular translocation of a corresponding fluorescent translocation reporter (FTR) gene is tested in viable test cells, to determine whether the tested PDM is mutated. In some embodiments, the specific patient derived marker is obtained and fused to a fluorescent reporter to create a patient derived reporter (PDR), wherein the subcellular translocation of the PDR is tested in viable test cells, to determine whether the tested PDR is mutated. In some embodiments, the identification of the driver mutations allows determining of drug response of the specific mutation identified to various drugs and/or combinations of drugs and are further configured to provide grading of the identified mutations (with respect to their tumoriogenic effect) and to determine various patient specific oncogenic indexes.

The methods and systems disclosed herein allow the qualitative and quantitative grading of various identified patient mutations and the determination of various indexes related to the tumoriogenity of the identified mutations and of the overall condition and prognosis of the patient.

In some embodiments, the present invention provides methods and systems for identifying patient specific driver mutations involved in cancer and further provides for various related indexes and methods for the determination thereof. In some embodiments, the driver mutations are oncogenic driver mutations. In some embodiments, the methods disclosed herein enable the formation of various cancer-related indexes, such as, for example, but not limited to: progression free survival, overall survival, probability of response to a drug; oncogenic grading index, curative index. In some embodiments, the indexes may be further related to treatment, as they provide a platform for quantitatively determining drug related indexes, such as a curative index of a drug or combination of drugs.

According to some embodiments, the identified mutations along with the quantitative data measured regarding the mutation, together with the data obtained regarding paracrine/autocrine activated pathways may be used to generate a "tumor oncogenic map", which indicates the affected signaling pathways within the patient tumor as well as the mutated genes and the oncogenic activity thereof.

According to some embodiments, there is provided a method for determining oncogenic grading of patient specific driver mutations, the method comprising identifying changes in subcellular localization/translocation of a reporter marker gene, whereby the changes in the subcellular localization are affected by the driver mutation, optionally, in the presence or absence of test drug or combination of drugs. In some embodiments, patient derived markers (PDMs) are obtained/derived from biological sample of the patient (directly or indirectly, for example, based on sequencing data), and are manipulated (engineered) to be expressed in a viable test cell, in the presence of a reporter chimeric gene (Fluorescence Translocation Reporter (FTR), which includes a chimeric product of a reporter gene portion and a target gene portion). The subcellular localization of the FTR in the test cell is then determined. If the subcellular localization of the FTR in the presence of the tested PDM is different than the subcellular localization of the FTR under normal conditions (i.e. in the presence of a corresponding WT PDM) and/or as compared to other known reference, it is indicative that the tested PDM is mutated. Further, the identified mutation may be tested in the presence of a test drug or combination of test drugs to identify a specific drug response of the tested PDM and further be used to determine various curative related indexes. Thus, using the methods disclosed herein, patient specific PDMs can be identified/characterized as being driver mutations and can be further assayed in the presence of a drug to measure the ability of the drug to affect the localization and oncogenic activity thereof to ultimately allow generation of various related indexes. Alternatively or additionally, in some embodiments, a PDM can be tested directly, by creating a PDR (i.e. a PDM linked/attached/fused to a reporter gene), and tracking its subcellular localization, without the use of FTR. By determining such driver mutations, the activated signaling pathways operating within the patient tumor can be identified. Further, this enables to precisely and specifically choose the required targeted therapy treatment needed to eradicate the tumor and avoid resistance mechanisms of the specific patient.

According to some embodiments, there is advantageously provided an enhanced and improved quantitative diagnostic platform for identifying patient specific derived mutations and determining various oncogenic-related indexes thereof, that allow grading and comparing between different mutations or combination of mutations in the same gene and/or in different genes and/or combination of different PDMs in the same test cell. In some embodiments, the methods disclosed include a cell-based assay that is able to identify driver mutations by monitoring their effect on an FTR in live (viable) cells, and based thereupon, to effectively determine/generate/calculate/produce various related indexes. The methods disclosed herein can advantageously further identify the resistance and sensitivity of different targeted therapy drugs, with a high degree of significance and can quantitatively identify and/or compare drug response of various patient mutations and further provide drug selection in the case of multiple drugs to the same target. Further, as exemplified herein below, the indexes determined by the methods disclosed herein are also concordant with the outcome observed in the clinic, providing a correlation between the in-vitro assay and the in-vivo condition. These results thus exemplify the capabilities of the disclosed methods and systems to identify various oncogenic related indexes of various mutations and to provide a quantitative platform to grade and compare between different mutations.

In some embodiments, the methods and systems disclosed herein provide a quantitative platform that enables the identification of the profile of the patient specific tumor activated signaling pathways by monitoring the activation of various signaling proteins (such as, for example, membrane-localized and/or intracellular receptors and signaling proteins), in viable test cells and generate, based on the results various related indexes. In some embodiments, the identification of the driver mutations may be performed by detecting intracellular translocation events and protein-protein interactions involving fluorescent reporter proteins (FTRs) (that is, translocation to/between various subcellular localizations, such as, the plasma membrane, cytosol, endosomes, nucleus, and the like). According to some embodiments, the methods and systems disclosed herein are advantageous as they provide, in addition to merely identifying multiple mutation events in the same biological sample of the same patient (including not yet identified mutations, and determining the oncogenic activity of such mutations), also the quantitative assessment and grading of such mutations, that can ultimately allow the accurate prognosis of the patient and/or determination of personalized treatment regime for the specific patient. Thus, the methods and systems disclosed herein in addition to allowing the identification of cellular events and patient specific mutations leading to cancer or involved in cancer, can also allow the indexing and grading of such events as well as to quantitatively identify/indicate an effective drug treatment specifically suited to the patient.

According to some embodiments, upon identification of the patient specific mutations and the signaling pathways involved, targeted therapy drugs/agents known (or unknown) to inhibit/affect/modulate the identified pathways/mutations may be added to the test cells and the oncogenic activity may be tested again, to identify the drugs/agents exhibiting the best effect on the tumor and the patient, a measurement that can serve as the basis for calculation of a "curative index". In some embodiments, the various drug/agents treatments and their respective curative index may be superimposed on the tumor oncogenic map and provide the health care provider with the patient specific underlying molecular tumor mechanism and the treatment options and their respective expected efficacy for treating the specific patient.

According to some embodiments, upon identification of the patient specific mutations and the signaling pathways involved, an oncogenic grading index (oncogenic index) may be determined/calculated/generated, wherein the identified mutations can be graded based on their oncogenic activity. The grading of the identified mutations may be attributive to the quantitative nature of the methods disclosed herein. The in-vitro effect of the identified mutations (as identified by the methods disclosed herein, in particular as determined by translocation events of a reporter gene) may be quantified so as to provide an oncogenic grading that is indicative of the oncogenic activity between different mutations of the same gene and/or between different mutations in different genes and correlate to the oncogenic activity of theses mutations in-vivo. In other words, the quantitative methods disclosed herein enables the quantitative comparison between different mutations in the same or different genes and correlates to the effect of these mutations in-vivo, which has far reaching implications as to the prognosis and the preferred line of treatment.

According to some embodiments, upon identification of the patient specific mutations and the signaling pathways involved (i.e., generation of the "tumor oncogenic map"), targeted therapy drugs/agents known to inhibit/affect the identified pathways/mutations may be incubated with the test cells and the inhibited/reduced oncogenic activity may be tested again, to identify the drugs/agents providing the highest reduction in the oncogenic index (as detailed below) of the tumor and the patient. In some embodiments, the inhibition in the oncogenic activity induced by the drug/agent is referred to herein as "Curative index". In some embodiments, the various drug/agents treatments and their respective curative index may be superimposed on the tumor oncogenic map and provide the health care provider with the patient specific underlying molecular tumor mechanism and the treatment options and their respective expected efficacy for treating the specific patient.

According to some embodiments, there are provided methods and systems for determining an oncogenic index (grading index). In some embodiments, the oncogenic index is indicative of the capacity of a given oncogenic mutation/ aberration to drive malignant growth within a given patient tumor sample. In some embodiments, the oncogenic index is indicative of the capacity of a given oncogenic mutation/aberration to drive malignant growth in the patient. In some embodiments, the oncogenic index is indicative of the prognosis of the patient, based on the capacity of a given oncogenic mutation/aberration to drive malignant growth within a given patient. In some embodiments the method and system include the calculating/computing/determining the degree of activation or inhibition of the tested FTR/PDR, for example, based on the nucleus to cytoplasm (NCR) ratio thereof. In some embodiments, the summation of all tested FTRs for a given PDM may then be calculated in a complex manner, to infer the impact of the tested PDM on malignant growth. According to some exemplary embodiments the oncogenic index has a numeric value, wherein the higher the value is, the higher the oncogenic index of the tested PDM is. In some embodiments, the value of the oncogenic index and units thereof are determined based on the data and/or additional parameters utilized in the generation of the index. In some embodiments, the step of quantifying comprises assigning a numerical value to the measurement.

According to some embodiments, there is provided a method of providing/generating an oncogenic grading index of one or more patient specific mutations in a biological sample of a cancer patient or of one or more aberrant signal transduction protein in tumor cells, comprising the steps of:
a) obtaining a plurality of mRNAs from the biological sample;
b) generating a cDNA library from the plurality of mRNAs;
c) amplifying specific cDNAs of the cDNA library using a set of primers complementary to polynucleotides encoding for known signal transduction proteins;
d) forming individual expression constructs of the amplified cDNAs wherein the cDNAs are operably linked to a promoter;
e) forming an addressable array of a first set of expression constructs harboring the amplified cDNAs from the biological sample, and a second set of expression constructs of the corresponding wild type cDNAs;
f) adding an expression vector encoding for a Fluorescence Translocation Reporter (FTR) gene comprising a target gene portion linked to a specific reporter gene portion for each locus in the array;
g) adding viable assay cells to each locus under conditions enabling transfection of the DNA constructs and vectors into the assay cells;
h) comparing at least one attribute of the expressed FTR in the assay cells expressing the cDNAs from the biological sample with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation; and
i) quantifying the disparate result of the candidate patient specific driver mutation to thereby determine the oncogenic grading index of said patient specific driver mutation.

In some embodiments, the step of quantifying comprises measuring the at least one attribute of the expressed FTR. In some embodiments, the step of quantifying comprises calculating/computing/determining the degree of translocation of the tested FTR/PDR and/or the NCR thereof. In some embodiments, the degree of translocation of the tested FTR/PDR is further calibrated/normalized/correlated/mapped to a reference value. In some embodiments, the degree of translocation of the tested FTR/PDR is further calibrated/normalized to the impact of the cell signaling pathway in which the tested FTR/PDR is involved, such as, for example, on the cell cycle or cell division. In some embodiments, the method comprises calculating/computing/determining the degree of activation or inhibition of the tested FTR/PDR. The summation of all tested FTRs for a given PDM may then be calculated in a complex manner, to infer the impact of the tested PDM on malignant growth. According to some embodiments the oncogenic index has a numeric value, wherein the higher the value is, the higher the oncogenic index of the tested FTR/PDR is. In some embodiments, the step of quantifying comprises assigning a numerical value to the measurement. In some embodiments, step g) precedes steps e) and/or f), in which case the assay cells are added to each locus, prior to addition of expression constructs and/or expression vectors.

In some embodiments, the attribute of the FTR is selected from localization of a fluorescent protein and translocation of a fluorescent protein. In some embodiments, the localization comprises a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In further embodiments, the reporter gene portion of the FTR encodes for a fluorescent marker, such as, for example, Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, ZsYellow1, DsRed2, AsRed2, and/or HcRed1.

In some embodiments, the biological sample is selected from tumor cells, tumor biopsy, tumor tissue and bodily fluids. In some embodiments, a candidate aberrant signal transduction protein identified by the method is a patient specific mutation. In some embodiments, the mutation is a driver mutation.

In some embodiments, the first and/or second sets of expression constructs comprise a double stranded linear DNA. In other embodiments, the promoter of the first and/or second set of expression constructs is an inducible promoter. In some embodiments, the promoter of the first and/or second set of expression constructs is a constitutive promoter.

In some embodiments, the method further comprises inducing expression of the expression construct and/or expression vector in the transfected cells to obtain gene products of the first set of cDNAs from the biological sample (for example, tumor) and the FTR for each locus in the array.

In further embodiments the expression constructs of the amplified cDNAs further comprise an IRES and a second reporter gene.

In some embodiments, the method further comprises drying the DNA constructs on a solid support in the presence of a transfection reagent. In some embodiments, the expression vector of the FTR is a circular expression vector. In further embodiments, the expression vector comprises a constitutive or inducible promoter.

In some embodiments, the method further comprises drying the DNA constructs on a solid support in the presence of a transfection reagent. In some embodiments, the method further comprises adding a test drug to the test cells. In some embodiments, steps g), h) and/or i) may be repeated in the presence of a drug. In some embodiments, the drug is an anti-cancer drug. In some embodiments, the drug is a test drug. In some embodiments, the method comprises adding more than one drug, concomitantly or sequentially. In some embodiments, the method comprises adding a combination of drugs. In some embodiments, the method comprises adding varying concentrations of drug(s), to quantitatively determine drug response. In some embodiments, the results obtained in the presence of the test compound may be used for determining a curative index, which is indicative of the reduction of the oncogenic activity of the tested gene(s), by the test drug and/or of the drug response of the mutations.

According to some embodiments, there is provided a method of generating/determining/producing/computing an oncogenic index of one or more patient specific mutations, comprising the steps of: a) forming an addressable array of a first set of expression constructs harboring genes comprising patient one or more patient specific mutations, and a second set of expression constructs of corresponding wild type genes; b) adding an expression vector encoding for a Fluorescence Translocation Reporter (FTR) gene comprising a target gene portion linked to a specific reporter gene portion for each locus in the addressable array; c) adding viable assay cells to each locus under conditions enabling transfection of the expression constructs and expression vectors into the assay cells; d) comparing the subcellular localization and/or translocation of the expressed FTR in the assay cells expressing the genes comprising the one or more patient specific mutations with their corresponding wild type expressed genes to identify a disparate result; e) quantifying the disparate result of the candidate patient specific mutation, by: i) processing the disparate result to determine the degree of translocation of the tested FTR in the presence of the first set of expression constructs and the second set of expression construct to determine activation level of the patient specific mutations; ii) normalizing the degree of translocation of the FTR in the presence of the first set of expression vectors, based on the degree of translocation of the FTR in the presence of the second set of expression constructs, to determine normalized activation level of the patient specific mutations; and iii) analyzing the mapping between the normalized activation level of the patient specific mutations and a clinical outcome (reference); to thereby determine the oncogenic grading index of said patient specific mutation. In some embodiments, step c) may precede step a) and/or step b).

According to some embodiments, analyzing may include utilizing machine learning or any other computational techniques. In some embodiments, analyzing may include such methods as, but not limited to: correlation univariate analysis machine, multivariate analysis machine, support vector machine, generalized linear model machine or combinations thereof.

In some embodiments, the degree of translocation is determined based upon nuclear to cytoplasm ratio (NCR).

In some embodiments, the index has a numeric value, indicative of the capacity of the candidate patient specific mutation to drive malignancy.

In some embodiments, the index may be indicative of progression free survival of the patient, overall survival of the patient, probability of drug response, Time to progression (TTP), Tumor response rate, Recurrence, Disease-free survival (DFS).

In some embodiments, the degree of translocation of the patient specific mutation may be further normalized to the impact of the cell signaling pathway in which the patient specific mutation is involved in.

In some embodiments, the subcellular localization may be selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR may encode for a protein selected from tumor suppressor, cytoskeleton protein, growth factor receptor, G-protein coupled receptor, cell adhesion protein, a protein kinase, transcription factor, adaptor protein and exchange factor. In some embodiments, the reporter gene portion of the FTR may encode for a fluorescent marker.

In some embodiments, the patient genes may be derived from a biological sample of the patient. In some embodiments, at least one of the mutations is an oncogenic mutation. In some embodiments, the mutation is a driver mutation. In some embodiments, the genes (or portions thereof) may be artificially synthesized, based on their sequence.

In some embodiments, the first and/or second sets of expression constructs comprise a double stranded linear DNA. In some embodiments, the promoter of the first and/or second set of expression constructs is an inducible or constitutive promoter. In some embodiments, the first and/or second set of expression constructs harbors a portion of a gene. In some embodiments, the method may further include a step of drying the constructs and/or vectors on a solid support in the presence of a transfection reagent.

In some embodiments, the method may further include a step of adding a test drug to the cells. In some embodiments, the method may further include calculating a curative index, indicative of the reduction in the capacity of the patient specific mutation to drive malignant growth in response to the test drug.

According to some embodiments, there is provided a system for generating an oncogenic grading index, comprising a processing circuitry configured to: a) obtain a disparate result indicative of the degree of subcellular translocation of a Fluorescence Translocation Reporter (FTR) gene product in the presence of a first set of expression constructs and in the presence of a second set of expression construct in test cells; b) determine activation level of patient specific mutations based on the degree of the subcellular translocation or localization of the FTR; c) normalize the subcellular translocation of localization of the FTR in the presence of the first set of expression constructs, based on the degree of translocation of the FTR in the presence of the second set of expression constructs, to determine normalized activation level of the patient specific mutations; and d) analyze the correlation between the activation level of the patient specific mutations and a clinical outcome (reference), to thereby determine the oncogenic index; wherein the disparate result is obtained by: i) forming an addressable array of a first set of expression constructs harboring genes comprising one or more patient specific mutations, and a second set of expression constructs of corresponding wild type genes; ii) adding an expression vector encoding for a Fluorescence Translocation Reporter (FTR) gene comprising a target gene portion linked to a specific reporter gene portion for each locus in the addressable array; and iii) adding viable assay cells to each locus under conditions enabling transfection of the expression constructs and expression vectors into the assay cells.

In some embodiments, analyzing may include machine learning. In some embodiments, analyzing may include correlation uni-variate analysis, multi-variate analysis machine, support vector machine analysis, generalized linear model analysis or any combination thereof.

In some embodiments, step iii) may precede step i) and/or step ii).

In some embodiments, the disparate result may be obtained by: i) adding viable assay cells to a substrate in an addressable array, under conditions enabling transfection of expression constructs and expression vectors into the assay cells; ii) adding to the assay cells an expression vector of a Fluorescence Translocation Reporter (FTR) gene comprising a target gene portion linked to a specific reporter gene portion for each locus in the array; iii) adding to the assay cells, at specific loci of the addressable array, a first set of expression constructs harboring genes comprising patient specific mutations, and adding to the assay cells, at specific locuses a second set of expression constructs of corresponding wild type genes, wherein the first set of expression constructs and the second sets of expression constructs are not added to a common locus. In some embodiments, step (ii) and/or step (iii) may precede step i).

In some embodiments, the processing circuitry may be further configured to calculate a curative index, indicative of the reduction in the capacity of the patient specific mutation to drive malignant growth in response to the test drug.

According to some embodiments, there is provided a method of generating a curative index indicative of susceptibility to drug treatment of one or more patient specific mutations, comprising the steps of: a) forming an addressable array of a first set of expression constructs harboring genes comprising one or more patient specific mutations, and a second set of expression constructs of corresponding wild type genes; b) adding an expression vector encoding for a Fluorescence Translocation Reporter (FTR) gene comprising a target gene portion linked to a specific reporter gene portion for each locus in the addressable array; c) adding viable assay cells to each locus under conditions enabling transfection of the expression constructs and expression vectors into the assay cells; d) comparing the subcellular localization and/or translocation of the expressed FTR in the assay cells expressing the genes comprising the mutation from with their corresponding wild type expressed genes in the presence and/or absence of a drug, to identify a disparate result; e) quantifying the disparate result of the candidate patient specific mutation, by: i) processing the disparate result to determine the degree of subcellular translocation of the tested FTR in the presence of the first set of expression constructs and the second set of expression construct to determine activation level of the patient specific mutations in the presence or absence of the drug; ii) normalizing the degree of subcellular translocation of the FTR in the presence of the first set of expression vectors, based on the degree of subcellular translocation of the FTR in the presence of the second set of expression constructs, in the presence or absence of the drug, to determine normalized activation level of the patient specific mutations; and iii) analyzing the correlation between the normalized activation level of the patient specific mutations in the presence or absence of the drug, and with a clinical outcome (reference); to thereby determine the curative index of the drug on the patient specific mutation.

In some embodiments the drug is an anti-cancer drug. In some embodiments, the method may include adding more than one drug, concomitantly or sequentially. In some embodiments, the method may include adding a combination of drugs. In some embodiments, the method may include adding varying concentration of drug(s). In some embodiments, step c) may precede step a) and/or step b).

According to some embodiments, the expression constructs may be obtained by a process comprising one or more of the following steps: i) generating a cDNA library from a plurality of mRNAs obtained from the biological sample of the patient; ii) amplifying specific cDNAs of the cDNA library using a set of primers complementary to polynucleotides encoding for genes suspected of harboring an oncogenic mutation; and iii) operably linking the amplified cDNAs to a promoter.

In some embodiments, the patient's genes or gene portions, suspected of harboring one or more mutations, may be synthesized by methods known in the art and optionally be operably linked to a promoter to obtain the expression constructs. In some embodiments, the patient genes (or portions thereof) and/or the corresponding wild-type genes may be artificially synthesized, based on their sequence and further processed to generate the corresponding PDMs.

According to some embodiments, there is further provided a kit for identifying patient specific driver mutations in biological sample of a cancer patient and for determining/calculating/computing various oncogenic-related indexes of the patient specific driver mutations. In further embodiments, there is provided a kit for identifying aberrant signal transduction pathways in tumor cells of a patient.

DESCRIPTION OF THE TEXT FILE SUBMITTED ELECTRONICALLY

The contents of the text file submitted electronically are incorporated herein by reference in their entirety: A computer readable format copy of the Sequence Listing (filename: NODX-002-01US_PCT_SEQ_LIST_ST25.txt, date recorded: Jan. 16, 2017, file size 9 kilobytes).

BRIEF DESCRIPTION OF THE DRAWINGS

FIG. 2B—A schematic representation of the signaling pathway affected by the PDM (BRAF) and the corresponding FTR (ERK2).

FIG. 3B—A schematic representation of the signaling pathway affected by PDM (EGFR) and the corresponding FTR (AKT1).

FIG. 4B—A schematic representation of the signaling pathway affected by PDM (EGFR) and the corresponding FTR (JNK1A1).

FIG. 5B—A bar graph showing the results of a cell based assay in which the genes encoding for EGFR in mutant forms (EGFR L861Q, EGFR L858R, EGFR 746Del, G719A/T790M/L861Q (EGFRtripleM)) have been expressed in test cells, along with different reporter proteins (FTR), and the amount of the FTR (JNK2-GFP, ERK2-GFP, STAT3-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 6B—A bar graph showing the results of a cell based assay in which the genes encoding for ERBB2 in mutant forms (ERBB2 V8421, ERBB2 V777L, ERBB2 S310F, ERBB2 L755S, ERBB2 D769Y, ERBB2 A1170P) have been expressed in test cells, along with different reporter proteins (FTR), and the amount of the FTR (ERK2-GFP, JNK2-GFP, STAT3-GFP, P38-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 7B—A bar graph showing the results of a cell based assay in which the genes encoding for cKIT in mutant forms (cKIT K642E, cKIT W557-K558 Del) have been expressed in test cells, along with different reporter proteins (FTR), and the amount of the FTR (ERK2-GFP, JNK2-GFP, STAT3-GFP, P38-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 8B—A bar graph showing the results of a cell based assay in which the genes encoding for KRAS in mutant forms (KRAS Q61H, KRAS G12V, KRAS G12R, KRAS G12A, KRAS G12D, KRAS G12C, KRAS G12S, KRAS A146V, KRAS A146T, KRAS G13D) have been expressed in test cells, along with different reporter proteins (FTR), and the amount of the FTR (ERK2-GFP, JNK2-GFP, FOXO3a-GFP, REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 9B—A bar graph showing the results of a cell based assay in which the genes encoding for PIK3CA in mutant forms (PIK3CA Y1021C, PIK3CA V344A, PIK3CA R38H, PIK3CA Q546L, PIK3CA N345K, PIK3CA H1047R, PIK3CA H1047L, PIK3CA E579K, PIK3CA E545K, PIK3CA E542K, PIK3CA C420R, PIK3CA R88Q/D350G) have been expressed in test cells, along with different reporter proteins (FTR), and the amount of the FTR (KOG1-GFP, P38-GFP, STAT3-GFP, REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 10B—A bar graph showing the results of a cell based assay in which the genes encoding for BRAF in mutant forms (BRAF V600E, BRAF V600K, BRAF G469V, BRAF G469A, BRAF G466V, BRAF G466E) have been expressed in test cells, along with different reporter proteins (FTR), and the amount of the FTR (ERK2-GFP, JNK2-GFP, REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 11B—A bar graph showing the results of a cell based assay in which the genes encoding for EGFR in WT form and KRAS in WT or mutant forms (KRAS G12V, KRAS G13D) have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 11C—A bar graph showing the results of a cell based assay in which the genes encoding for EGFR in WT or mutant forms (EGFR L858R, EGFR T790M) and KRAS in WT have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 11D—A bar graph showing the results of a cell based assay in which the genes encoding for EGFR in WT or mutant forms (EGFR L858R, EGFR T790M) and KRAS in WT or mutant forms (KRAS G12V, KRAS G13D) have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 12B—A bar graph showing the results of a cell based assay in which the genes encoding for EGFR in WT form and KRAS in WT or mutant forms (KRAS G12V, KRAS G13D) have been expressed in test cells, along with different reporter proteins (FTR), and the amount of the FTR (REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 12C—A bar graph showing the results of a cell based assay in which the genes encoding for EGFR in WT or mutant forms (EGFR L858R, EGFR T790M) and KRAS in WT have been expressed in test cells, along with different reporter proteins (FTR), and the amount of the FTR (REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 12D—A bar graph showing the results of a cell based assay in which the genes encoding for EGFR in WT or mutant forms (EGFR L858R, EGFR T790M) and KRAS in WT or mutant forms (KRAS G12V, KRAS G13D) have been expressed in test cells, along with different reporter proteins (FTR), and the amount of the FTR (REL-A-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 13B—A bar graph showing the results of a cell based assay in which the genes encoding for EGFR in WT form and KRAS in WT or mutant forms (KRAS G12V, KRAS G13D) have been expressed in test cells, along with different reporter proteins (FTR), and the amount of the FTR (JNK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 13C—A bar graph showing the results of a cell based assay in which the genes encoding for EGFR in WT or mutant forms (EGFR L858R, EGFR T790M) and KRAS in WT have been expressed in test cells, along with different reporter proteins (FTR), and the amount of the FTR (JNK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 13D—A bar graph showing the results of a cell based assay in which the genes encoding for EGFR in WT or mutant forms (EGFR L858R, EGFR T790M) and KRAS in WT or mutant forms (KRAS G12V, KRAS G13D) have been expressed in test cells, along with different reporter proteins (FTR), and the amount of the FTR (JNK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 14B—A bar graph showing the results of a cell based assay in which the genes encoding for EGFR in WT form and BRAF in WT or mutant forms (BRAF V600E, BRAF V600K) have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 13C—A bar graph showing the results of a cell based assay in which the genes encoding for EGFR in WT or mutant forms (EGFR L858R, EGFR T790M) and BRAF in WT have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

FIG. 13D—A bar graph showing the results of a cell based assay in which the genes encoding for EGFR in WT or mutant forms (EGFR L858R, EGFR T790M) and BRAF in WT or mutant forms (BRAF V600E, BRAF V600K) have been expressed in test cells, along with different reporter proteins (FTR), and the amount of the FTR (ERK2-GFP) in the cytoplasm and in the nucleus was quantified based on fluorescence microscope images of the cells (fixed 24 hours after transfection). The difference in ratio between the intensity of the FTR in the nucleus (N) and cytoplasm (C) was measured (Delta N:C ratio).

DETAILED DESCRIPTION OF THE INVENTION

Figure 1:
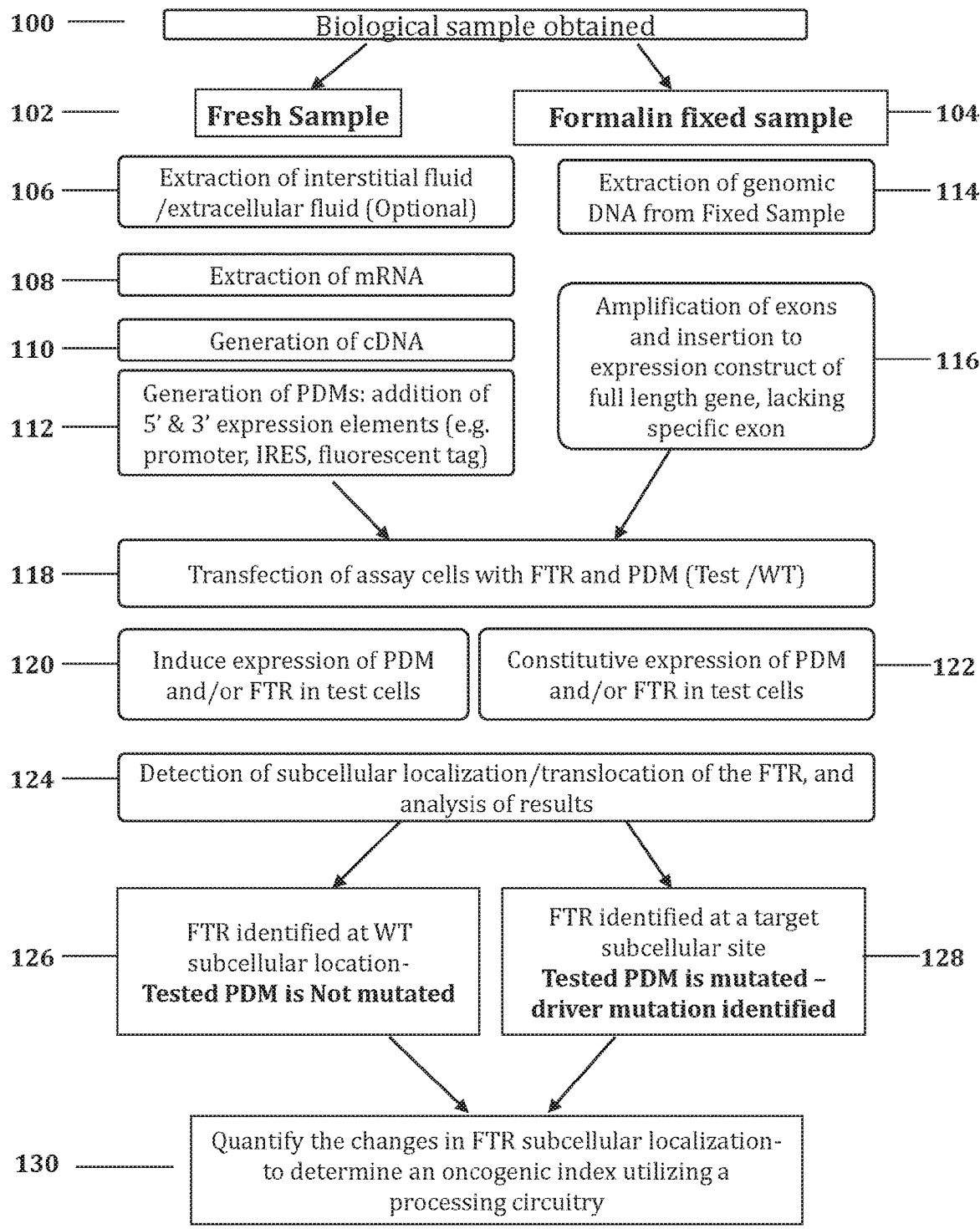
FIG. 1 is a schematic block diagram of steps of a method for identification of patient driver mutations and detection of drug response thereof, according to some embodiments.

According to some embodiments, there are provided methods and systems for determining various oncogenic related indexes of patient specific driver mutations, by identifying and quantifying changes in signaling pathway activity, which is associated with the function of the driver mutation. In some embodiments, the changes in the signaling pathway activity are determined by identifying and quantifying changes in subcellular localization of a reporter gene, whereby the changes in the subcellular localization of the reporter gene and the degree of said changes are affected by the driver mutation. In some embodiments, patient derived markers (PDMs) may be obtained from biological sample of the patient, and are manipulated (engineered) to be expressed in a test cell, in the presence of a reporter chimeric gene (FTR). In some embodiments, patient derived markers (PDMs) may be obtained by artificially generating (synthesizing) the corresponding patient genes(s), based on their identified sequence and further manipulating those to be expressed in a test cell. In some embodiments, additionally or alternatively, the patient specific marker is fused to the fluorescent reporter to create a patient derived reporter (PDR). The subcellular localization of the FTR (and/or PDR, if applicable) in the test cell is then determined. If the subcellular localization of the FTR in the presence of the tested PDM (and/or the PDR, if applicable) is different than the subcellular localization of the FTR (and/or PDR, if applicable) under normal conditions (i.e. in the presence of a corresponding WT PDM) or as compared to other predetermined reference, it is indicative that the tested PDM (or PDR) is mutated. Further, the method advantageously allows quantification of the response of the identified PDM (and/or PDR, if applicable) and the determination of various oncogenic related indexes, such as, oncogenic grading index, which is indicative of the severity of the identified mutation(s). Thus, using the methods disclosed herein, patient specific PDMs can be identified/characterized as being driver mutations and further, their relative importance (for example, in terms of oncogenic activity) may be determined and quantified. Moreover, by determining such driver mutations, the activated signaling pathways operating within the patient tumor and the drugs response thereof can be identified, quantified and graded so as to determine the relative importance of the various pathways for the specific patient. This enables to precisely and specifically provide prognosis and further choose an optimized and personalized targeted therapy treatment.

In some embodiments, the methods and systems disclosed herein allow the quantitative analysis and comparison of the effect of the identified mutations and aberrant signaling proteins and signaling pathways. According to some embodiments, the methods and systems disclosed herein are advantageous since they allow identification of multiple mutation events in the same biological sample of the same patient, in addition to yet unidentified mutations, and further allow the quantitative determination of the oncogenic activity of such mutations and the grading and indexing thereof as well as grading the curative impact of various drugs on the identified mutations. For example, in currently used methods of treatment, gastrointestinal stromal tumor patients harboring cKit mutations are treated with Gleevec. However, common resistance mechanisms occur through secondary mutations within cKit itself or in downstream pathways, rendering such treatment ineffective. Likewise, lung cancer patients that have an EGFR oncogenic mutation are eligible for targeted therapy treatment, but there are several such drugs available. Thus, the methods and systems disclosed herein allow the detection, identification, quantification and grading/indexing of the identified mutations, to eventually provide accurate prognosis and optionally further determine a personalized and optimized drug treatment to the specific patient.

In some embodiments, the methods and systems disclosed herein enable the emulation of the patient tumor to identify activated signaling pathways and the graded oncogenic activity and moreover determine tumor sensitivity/resistance to various drugs. In some embodiments, this is performed by incubating the transfected test cells with one or more test drugs. In some embodiments, this may be performed by incubating the transfected test cells with the patient body fluids (such as plasma, pleural effusion, or interstitial fluid).

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The term "construct", as used herein refers to an artificially assembled or isolated nucleic acid molecule which may include one or more nucleic acid sequences, wherein the nucleic acid sequences may include coding sequences (that is, sequence which encodes for an end product), regulatory sequences, non-coding sequences, or any combination thereof. The term construct includes, for example, vectors but should not be seen as being limited thereto.

The term "Expression vector" refers to vectors that have the ability to incorporate and express heterologous nucleic acid fragments (such as DNA) in a target cell. In other words, an expression vector comprises nucleic acid sequences/fragments capable of being transcribed. Many viral, prokaryotic and eukaryotic expression vectors are known and/or commercially available. Selection of appropriate expression vectors is within the knowledge of those having skill in the art.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, a mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

As used herein, the terms "introducing" and "transfection" may interchangeably be used and refer to the transfer or introduction of molecules, such as, for example, nucleic acids, polynucleotide molecules, vectors, and the like into a target cell(s), and more specifically into the interior of a membrane-enclosed space of a target cell(s), such as the cytosol of a cell, the nucleus of a cell, an interior space of a mitochondria, endoplasmic reticulum (ER), and the like. The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. In some embodiments, the introduced nucleic acid may be, for example, a modified nucleic acid that may be in the form of DNA, RNA. In some embodiments, the nucleic acid is dehydrated prior to being transfected to a cell. In some embodiments, the nucleic acid is incorporated into a vector, such as, for example, an expression vector. Each possibility represents a separate embodiment of the present invention.

The term "expression", as used herein, refers to the production of a desired end-product molecule in a target cell. The end-product molecule may include, for example an RNA molecule; a peptide or a protein; and the like; or combinations thereof.

As referred to herein, the term "patient" is directed to a subject suspected of having or diagnosed with a disease. In some embodiments, the term patient is directed to a subject having or diagnosed with cancer. In some embodiments, a patient is eligible for tumor biopsy.

As referred to herein, the term "biological sample" is directed to include any appropriate body-derived sample. The sample may include fluid samples such as whole blood, peripheral blood monocytes, leukocytes, bone marrow. The samples may include various cells and tissues. The sample may include biopsies. The sample may include fixed and/or embedded tissue sections. The samples may be either freshly extracted or frozen. In another embodiment, the sample is a blood sample. In another embodiment, the sample is a bone marrow sample. In another embodiment, methods for isolating and maintaining a sample comprising blood cells from a subject are known to one of average skill in the art. In some embodiments, a sample comprising polynucleotides, polypeptides, peptides, antibodies fragments and derivatives thereof may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof. In some embodiments, the biological sample is obtained from a tumor.

As referred to herein, the terms "Patient Derived Marker" ("PDM"), and "subject PDM" are directed to a gene or gene product (or portions thereof) that is isolated or obtained or derived (directly or indirectly) from a biological sample of the subject and its activity in a functional assay is determined. In some embodiments, to the PDM nucleic acid sequence, (which is directly obtained from the biological sample (for example, by generation of a cDNA), or is artificially synthesized (i.e., indirectly obtained)), 5' and/or 3' regulatory elements and/or additional reporter genes are added. In some examples, a PDM as used herein comprises a chimeric nucleic acid sequence molecule comprising a regulatory element (promoter)—the PDM sequence regulatory element (IRES)-reporter gene, not necessarily in this order. Thus, when such a nucleic acid molecule is introduced and expressed in a target cell, the PDM gene product (protein) and the reporter gene product (protein) are expressed in the cell. Additionally or alternatively, an IRES sequence can be omitted and a chimeric protein comprising the PDM gene product and the reporter gene product is expressed in the cell. The thus formed chimeric protein is referred to herein as "Patient Derived Reporter" ("PDR"), or "subject PDR". In some embodiments, the terms "control PDM", "wild type PDM", "corresponding PDM" and "corresponding wild type PDM" are directed to a wild type gene corresponding to the PDM gene (i.e. a non-mutated, fully active), that is used as control. In some embodiments, the wild type PDM is not derived from a biological sample of the patient. The control PDM is used to compare the activity of the subject PDM and the wild type (wt) PDM.

As referred to herein, the term "Fluorescence Translocation Reporter" ("FTR") is directed to a chimeric reporter gene and the corresponding gene product. The chimeric FTR comprising a reporter gene portion (such as a fluorescent marker (protein)) linked to a predetermined target (marker) gene portion (such as, for example, a cell signaling protein, kinase, enzyme, and the like), whereby at least one attribute of the target (marker) gene may be affected (directly or indirectly) by the tested PDM.

As referred to herein, the terms "test cell", "target cell" and "assay cell" may interchangeably be used. The terms are directed to an assay cell which is transfected with a poly nucleic acid molecule such as PDM and/or PDR and/or FTR and/or any of control genes, as described herein. In some embodiments, the test cell is an eukaryotic cell. In some embodiments, the test cell may be a primary cell or a cell line. In another embodiment, an assay cell is a non-cancerous cell. In another embodiment, an assay cell is derived from a cell line. In another embodiment, an assay cell is responsive to at least one cancer-secreted growth factor. In another embodiment, an assay cell is amenable by transfection. In another embodiment, an assay cell is amenable by transient transfection. In another embodiment, an assay cell is a cell, in which the expression of one or more endogenous genes have been reduced or eliminated by any molecular method. In another embodiment, an assay cell is HeLa cell. In another embodiment, an assay cell is HEK 293 cell. In another embodiment, an assay cell is PC12 cell. In another embodiment, an assay cell is U2OS cell. In another embodiment, an assay cell is NCI60 cell lines, such as, A549, EKVX, T47D, HT29. In some embodiments, the assay cell is a cell derived from the patient. In some embodiments, the assay cell is a cell derived from a cancer patient.

As used herein, the terms "subcellular localization", "subcellular region" and "subcellular compartment" refer to any defined part of a cell that may be distinguished by various means (such as, for example, by visual means) from other regions of the cell. In some examples, a subcellular region may be a restricted area within a cell. In some embodiments, a subcellular region may include an organelle. Non limiting examples of subcellular localization include, for example, but not limited to: nucleus, nucleolus, cytosol, mitochondria, endoplasmic reticulum (ER), chloroplasts, membranes, dendritic spines, Golgi apparatus, lysosomes, peroxisomes, endosomal compartments, cytoskeleton, and the like. Each possibility is a separate embodiment. In some embodiments, the term "subcellular translocation" refers to a detected change in the subcellular localization of a reporter gene (such as, FTR or PDR) under various conditions. For example, translocation may be to/from the nucleus from/to the cytosol.

As referred to herein, the terms "drug", "test compound" and "test drug" may interchangeably be used. The term drug is directed to any compound, substance, molecule, agent and/or reagent that has an effect in treating a condition. In some embodiments, the drug is an anti-cancer drug. In some embodiments, the term drug may encompass more than one drug. In some embodiments, the term drug includes a combination of drugs. In some embodiments the drug is an inhibitor of expression and/or activity of a cellular protein.

As referred to herein, the terms "drug response" and "susceptibility to drug" may interchangeably be used. The terms refer a response or effect elicited by a test drug. In some embodiments, the terms relate to capability of the drug(s) to suppress the effect of a mutation, such as, an oncogenic mutation.

In some embodiments, the terms "Treating a disease" or "treating a condition" are directed to administering of one or more compounds, effective to ameliorate symptoms associated with a disease, to lessen the severity or cure the disease, or to prevent the disease from occurring.

The terms "Detection, "Diagnosis" refer to methods of detection of a disease, symptom, disorder, pathological or normal condition; classifying a disease, symptom, disorder, pathological condition; determining a severity of a disease, symptom, disorder, pathological condition; monitoring disease, symptom, disorder, pathological condition progression; forecasting an outcome and/or prospects of recovery thereof. The term "Diagnostic" means identifying the presence or nature of a pathologic condition.

The term "substrate" is directed to a solid support on which the nucleic acid molecules, constructs, vectors and/or assay cells are placed. The substrate may include any type of suitable substrate, such as, but not limited to: chip, slide, well, container, tube, vial, and the like. In some embodiments, the substrate is a chip. In some embodiments, the substrate is a microscope slide. In some embodiments the substrate is a multi-well plate, such as a 6-well plate, 12-well plate, 24-well plate, 48-well plate, 96 well plate, 384 well plate, and the like. In some embodiments, the substrate is constructed such that it includes a matrix array (locuses), whereby each locus (or point in the array) is designated and identifiable. In some embodiments, the nucleic acid molecules are dehydrated on the substrate. In some embodiments, the nucleic acid molecules are dehydrated on the substrate in the presence or absence of a transfection reagent.

The terms "driver mutation" and "oncogenic mutation" may interchangeably be used. The terms are directed to a mutated gene or gene product, which is directly or indirectly related to a disease. In some embodiments, the terms are directed to a mutated gene or gene product that is related to and/or involved in and/or can lead and/or cause a disease, such as cancer.

The term "addressable array" is directed to a matrix, which includes spatially separated locuses, the location of which is identifiable and distinguishable. In some exemplary embodiments, an addressable array may include a multi-well plate, wherein each well (locus) is spatially identifiable. In other exemplary embodiments, an addressable array may include any substrate having separable locuses situated/located in a designated array.

The term "polynucleotides encoding for a protein" refers to a polynucleotide sequence or molecule encoding for the corresponding protein or a portion thereof. In some embodiments, the polynucleotide encoding for a protein comprises the nucleotide sequence of the gene or a portion thereof, which encodes for the corresponding protein.

The term "oncogenic related index" is directed to include any type of index, which may be generated by a calculation or grading of identified mutation(s) (one or more, or combinations thereof), with respect to their oncogenic activity or ability. In some embodiments, the oncogenic related index is a numerical value. In some embodiments, the oncogenic related index is reflective of the activity of the mutation(s) in-vivo. In some embodiments, the oncogenic-related index may be used to compare between different mutations in the same gene and/or different mutations in different genes.

Reference is now made to FIG. 1, which schematically illustrates a block diagram of exemplary steps in a method for identifying patient specific driver mutations, in a biological sample of a patient, and for identifying drug response thereof, according to some embodiments. As shown in FIG. 1, at step 100, a biological sample of the patient is obtained. The biological sample may be selected from, but not limited to: blood, serum, biopsy, needle biopsy, bronchoalveolar lavage, pleural effusion, tumor tissue, urine, saliva and tumor tissue. In some embodiments, the biological sample may be fresh (fresh or freshly frozen), i.e. samples which are not fixed (step 102). In some embodiments, the biological sample may be fixed, by methods known in the art for fixation of biological sample (Step 104).

As shown in FIG. 1, from a fresh biological sample (Step 102), various components may be extracted, each by appropriate methods well known in the art. For example, as shown in Step 106, interstitial fluid (IF) (extracellular fluid) may be extracted and saved for future use. Additionally, mRNA may be extracted from the fresh biological sample (Step 108). The extracted/isolated mRNA is then used for the generation of cDNA libraries (Step 110), by methods well known in the art (such as, by using polydT primers). Specific PDM cDNAs are amplified from the cDNA library and created by using appropriate primer pairs, corresponding to desired gene regions (polynucleotides) of predetermined PDMs. The selected PDMs, may be chosen based on the known function/activity/role of a corresponding WT PDM or mutated PDM in various disease states (for example, oncogenes). Next, at step 112, an assay PDM is created, by adding a regulating promoter element to the 5' end of the PDM cDNA, and optionally adding a 3' IRES and a tag, such as a reporter gene, fluorescent tag, and the like. In some embodiments, the promoter element may be a constitutive promoter or an inducible promoter. In some embodiments, the PDM cDNA may further include an additional expression cassette which includes an FTR encoding portion. In some embodiments, the specific PDMs are generated by artificially synthesizing/generating the specific PDMs (based on their identified sequence), without the step of generation of a cDNA library.

As further shown in FIG. 1, at step 114, genomic DNA may be extracted from a fixed biological sample (such as a formalin fixed sample (Step 104)). At step 116, the extracted DNA may undergo amplification of specific, predetermined exons (which are known to be mutated in cancer cases) and consequent ligation/fusion to expression constructs comprising the corresponding full length gene, lacking the specific exons amplified to generate a tested PDM.

Next, in step 118, the nucleic acid molecule of each of the PDMs generated in step 112 and/or step 116 (via generation of cDNA, or artificially synthesized) may be placed/spotted on a support substrate (such as, a slide, well (for example, microplate well), chip, and the like) at a designated locus (location). The PDM is placed in a mixture with a nucleic acid molecule encoding for the chimeric reporter (FTR), wherein the FTR is selected to correspond to the PDM (i.e., the selected FTR may be functionally affected (directly or indirectly) by the PDM). The mixture of the nucleic acid molecules encoding for the PDM and the FTR may further comprise appropriate transfection reagents to allow the transfection of the molecules to a test cell. Optionally, the PDM+FTR mixtures are dehydrated onto the substrate. In another option, the PDM and FTR are constructed to be located on a single nucleic acid molecule, allowing independent expression of both proteins in the cell. In parallel, a control assay is prepared, which comprises a WT PDM and a corresponding FTR. Further in step 118, a sufficient amount of selected test cells are added to the substrate, together with appropriate growth media. The cells may be added prior to or after the addition of the nucleic acid molecules. In some embodiments, a sufficient amount of test cells comprises about 1-10000 cells per well (96 multi-plate well). In some embodiments, a sufficient amount of test cells comprises about 1-50000 cells per well (24 multi-plate well). In some embodiments, a sufficient amount of test cells comprises about 1-100000 cells per well (12 multi-plate well). In some embodiments, a sufficient amount of test cells comprises about 1-1000 cells per well (96 multi-plate well). In some embodiments, a sufficient amount of test cells comprises about 1-1000 cells per well (384 multi-plate well). In some embodiments, the test cell is selected from, but not limited to: HeLa cells, HEK 293 cells, U205, PC12, NCI60, A549, EKVX, T47D, HT29, and the like. The cells are then incubated for a designated period of time (such as, in the range of about 6-60 hours) to allow expression of the FTR and optionally of the PDM. Optionally, in some embodiments, in step 118, the cells are added to the solid substrate (with a suitable growth medium) for a period of time (such as 0.5-48 hours) and then the nucleic acid molecules encoding for the PDMs and/or FTR are added to the cells, under conditions allowing transfection of the molecules into the cells.

Next, at step 120, after a predetermined period of time (such as, 4-60 hours), cell growth medium may be replaced with fresh media. In some embodiments, the replacement media is low serum media. Next, after an additional incubation period (such as, in the range of 4-16 hours), induction of the expression of the PDM, controlled by an inducible promoter is initiated. Induction of the inducible promoter may be initiated, for example by addition of tetracycline when using a tetracycline inducible promoter, or ecdysone when using in an ecdysone inducible promoter or any other methods known in the art.

Optionally, at step 122, for PDMs generated from fixed samples (step 116), after a predetermined period of time (such as, 4-60 hours), cell growth medium is replaced with fresh media. In some embodiments, the replacement media is low serum media. Next, after an additional incubation period (such as, in the range of 4-24 hours), the PDMs are expressed under the control of a constitutive promoter.

Next, at step 124, after an additional period of time that allows for the expression of the PDMs in the test cells (such as, for example, in the range of about 4-48 hours), the subcellular localization of the FTR is determined. Determination of the subcellular localization of the FTR may be performed by various means, such as, imaging using a fluorescent microscope, fractionation of subcellular compartments using biochemical methods, and the like. In some exemplary embodiments, the cells are fixed and the fluorescent FTR localization is determined by fluorescent imaging. Analysis and comparison of the subcellular localization of the FTR under various experimental conditions allows the determination as to whether the tested PDM is defective (i.e. mutated), or not. For example, subcellular localization of the FTR is determined in cells, in which it is co-expressed with the tested PDM (test assay). In addition, subcellular localization of the same FTR is determined in cells, in which it was co-expressed with WT PDM (control assay). Differences in subcellular localization of the FTR between the test assay and the control assay indicate as to the functional activity of the tested PDM. Thus, for example, in Step 126, if the FTR is identified in the test assay to be at the same subcellular localization as in the control assay, the tested PDM is not mutated. For example, in Step 128, if the FTR is identified in the test assay to be at a different subcellular localization as in the control assay, the tested PDM is mutated, which indicates that this PDM is a driver mutation. Next, at step 130, the results are quantified (i.e. the changes in subcellular localization of the FTR, such as, for example, nuclear to cytoplasm (N:C) ratio), so as to determine/calculate/generate an oncogenic grading index (for example, by a processing circuitry), that may be used as is, or with further manipulations, to compare between different mutations, different genes, and the like, and to provide further patient-specific related information (such as, prognosis), as further detailed below.

According to some embodiments, there is provided a method of determining an oncogenic-related index of one or more patient specific driver mutations in a biological sample of a cancer patient, comprising one or more of the steps of (in any selected order):
  a) obtaining a plurality of mRNAs from the biological sample;
  b) generating a cDNA library from the plurality of mRNAs;
  c) amplifying specific cDNAs of the cDNA library using a set of primers complementary to polynucleotides encoding for known signal transduction proteins;
  d) forming individual expression constructs of the amplified cDNAs wherein the cDNAs are operably linked to a promoter;
  e) forming an addressable array of a first set of expression constructs harboring the amplified cDNAs from the sample, and a second set of expression constructs of the corresponding wild type cDNAs;
  f) adding an expression vector encoding for a Fluorescence Translocation Reporter (FTR) gene comprising a target gene portion linked to a specific reporter gene portion for each locus in the array;
  g) adding viable assay cells to each locus under conditions enabling transfection of the DNA constructs and vectors into the assay cells;
  h) comparing at least one attribute of the expressed FTR in the assay cells expressing the cDNAs from the sample with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation; and
  i) quantifying the disparate result of the candidate patient specific driver mutation, to thereby determine the oncogenic-related index of said patient specific driver mutation.

In some embodiments, the step of quantifying comprises measuring the at least one attribute of the expressed FTR. In some embodiments, the step of quantifying comprises calculating/computing/determining the degree of translocation of the tested FTR/PDR. In some embodiments, the degree of translocation of the tested FTR/PDR is further calibrated/normalized to infer the impact of the tested PDM on malignant growth. According to some embodiments the oncogenic index has a numeric value, wherein the higher the value is, the higher the oncogenic index of the tested FTR/PDR is. In some embodiments, the step of quantifying comprises assigning a numerical value to the measurement.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In such embodiments, steps d) and f), above, are combined to one step: (alternative step d)): forming individual expression constructs of the amplified cDNAs wherein the cDNAs are operably linked to a promoter, to produce test patient derived markers (test PDMs); wherein said expression constructs further includes a specific reporter gene (FTR). In some embodiments, the FTR is linked to a promoter (that may be identical or different from the promoter of the PDM). In further embodiments, the FTR comprises a target gene portion linked to a reporter gene portion.

In some embodiments, step g) precedes steps e) and/or f), in which case the assay cells are added to each locus prior to addition of the expression cassettes.

In some embodiments, the method includes, in step e), a third set of expression constructs of corresponding proteins of the PDMs, which comprises one or more known driver mutations in said genes (herein "artificial PDMs"), that may be used as experimental control. The third set of expression constructs is added to the addressable array.

In some embodiments, the oncogenic related index may be selected from: oncogenic grading index, curative index, total oncogenic index, total curative index, Metastatic index, angiogenic index, genomic instability index, Microtubule dynamic instability index, cell cycle progression index, apoptotic index, differentiation index and the like or combinations thereof. Each possibility is a separate embodiment.

According to some embodiments, there is provided a method of determining an oncogenic grading index of one or more patient specific driver mutations in a biological sample of a cancer patient, comprising one or more of the steps of (in any selected order):
a) obtaining a plurality of mRNAs from the biological sample;
b) generating a cDNA library from the plurality of mRNAs;
c) amplifying specific cDNAs of the cDNA library using a set of primers complementary to polynucleotides encoding for known signal transduction proteins;
d) forming individual expression constructs of the amplified cDNAs wherein the cDNAs are operably linked to a promoter;
e) forming an addressable array of a first set of expression constructs harboring the amplified cDNAs from the biological sample, and a second set of expression constructs of the corresponding wild type cDNAs;
f) adding an expression vector encoding for a Fluorescence Translocation Reporter (FTR) gene comprising a target gene portion linked to a specific reporter gene portion for each locus in the array;
g) adding viable assay cells to each locus under conditions enabling transfection of the DNA constructs and vectors into the assay cells;
h) comparing at least one attribute of the expressed FTR in the assay cells expressing the cDNAs from the biological sample with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation; and
i) quantifying the disparate result of the candidate patient specific driver mutation, to thereby determine the oncogenic grading index of said patient specific driver mutation.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In such embodiments, steps d) and f), above, are combined to one step: (alternative step d)): forming individual expression constructs of the amplified cDNAs wherein the cDNAs are operably linked to a promoter, to produce test patient derived markers (test PDMs); wherein said expression constructs further includes a specific reporter gene (FTR). In some embodiments, the FTR is linked to a promoter (that may be identical or different from the promoter of the PDM). In further embodiments, the FTR comprises a target gene portion linked to a reporter gene portion.

In some embodiments, step g) precedes steps e) and/or f), in which case the assay cells are added to each locus prior to addition of the expression cassettes.

In some embodiments, the method includes, in step e), a third set of expression constructs of corresponding proteins of the PDMs, which comprises one or more known driver mutations in said genes (artificial PDMs), that may be used as experimental control. The third set of expression constructs is added to the addressable array.

In additional embodiments, the method further comprises a step j) which comprises repeating any one of steps g) to i) in the presence of a drug and comparing at least one attribute of the expressed FTR in the assay cells expressing the cDNAs from the sample and/or the corresponding wild type expressed cDNAs in the presence and/or absence of the drug; wherein a disparate result between the assay cells expressing the cDNA derived from the biological sample of the cancer patient and the corresponding wild type cDNA, is used for identifying the cDNA from the biological sample as a candidate patient specific driver mutation; and wherein a disparate result between the assay cells expressing the cDNA derived from the biological sample of the cancer patient in the absence or presence of a drug is indicative of a drug response of the candidate patient specific driver mutation.

In some embodiments, the step of quantifying comprises measuring the at least one attribute of the expressed FTR. In some embodiments, the step of quantifying comprises calculating/computing/determining the degree of translocation of the tested FTR/PDR. In some embodiments, the degree of translocation of the tested FTR/PDR is further calibrated/normalized to infer the impact of the tested PDM on malignant growth. According to some embodiments the oncogenic index has a numeric value, wherein the higher the value is, the higher the oncogenic index of the tested FTR/PDR is. In some embodiments, the step of quantifying comprises assigning a numerical value to the measurement.

In some embodiments, the biological sample is selected from tumor cells, tumor biopsy, tumor tissue and bodily fluids.

According to some embodiments, a combination of 2 or more PDMs may be tested with a given FTR in assay cells so as to measure/determine/identify the cumulative effect of the PDMs.

According to some embodiments, the method may include introducing into the assay cells discrete expression constructs of more than one PDM. In some embodiments, the discrete expression constructs may be introduced concomitantly or sequentially. In some embodiments, the methods may include introducing into the cells an expression cassette encoding for more than one PDM (for example, encoding for two discrete PDMs, three discrete PDM, and the like).

According to some embodiments, there is provided a method of determining an oncogenic grading index of one or more patient specific driver mutations in a biological sample of a cancer patient, comprising one or more of the steps of:
  a) obtaining a plurality of mRNAs from the biological sample;
  b) generating a cDNA library from the plurality of mRNAs;
  c) amplifying specific cDNAs of the cDNA library using a set of primers complementary to polynucleotides encoding for known signal transduction proteins;
  d) forming individual expression constructs of the amplified cDNAs wherein the cDNAs are operably linked to a promoter;
  e) adding viable assay cells to a substrate, in an addressable array;
  f) adding to the assay cells a first set of expression constructs harboring the amplified cDNAs from the biological sample, and a second set of expression constructs of the corresponding wild type cDNAs; wherein each of the expression constructs is added to the assay cells at a disparate, addressable locus, under conditions enabling transfection of the expression constructs into the assay cells;
  g) adding to the assay cells an expression vector encoding for a Fluorescence Translocation Reporter (FTR) gene comprising a target gene portion linked to a specific reporter gene portion for each locus in the array;
  h) comparing at least one attribute of the expressed FTR in the assay cells expressing the cDNAs from the sample with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific driver mutation; and
  i) quantifying the disparate result of the candidate patient specific driver mutation, to thereby determine the oncogenic grading index of said patient specific driver mutation.

In some embodiments, the assay cells are stably transfected with a designated FTR, and such assay cells, expressing the corresponding FTR may be used in the methods disclosed herein.

In some embodiments, the method includes, in step f), adding to assay cells at a disparate, addressable locus, under conditions enabling transfection, a third set of expression constructs of corresponding proteins of the PDMs, which comprises one or more known driver mutations in said genes (corresponding artificial PDMs).

In some embodiments, the method further comprises comparing at least one attribute of the FTR in the cells expressing the cDNAs from the sample with its corresponding wild type expressed cDNAs; wherein a disparate result between the assay cells expressing the biological sample derived cDNA and the corresponding wild type cDNA is used for identifying the cDNA from the biological sample as a candidate patient specific oncogenic mutation.

In some embodiments, the method further comprises repeating a step adding to the assay cells a drug and comparing at least one attribute of the expressed FTR in the assay cells expressing the cDNAs from the sample and/or the corresponding wild type expressed cDNAs in the presence and absence of the drug; wherein a disparate result between the assay cells expressing the cDNA derived from the biological sample of the cancer patient in the absence or presence of a drug is indicative of a drug response of the candidate patient specific oncogenic mutation.

According to some embodiments, there is provided a method for determining an oncogenic-related index of aberrant signal transduction proteins in biological samples of cancer patient, and/or of patient specific driver mutation, comprising one or more of the steps of (in any appropriate order):
  a) obtaining a sample of a plurality of mRNAs from a biological sample of the cancer patient, such as from a biopsy of the tumor;
  b) generating a cDNA library from the plurality of tumor mRNAs, by methods known in the art;
  c) amplifying individual cDNA samples of the cDNA library using a set of primers complementary to polynucleotides encoding for known proteins, wherein the proteins are involved in various cell signaling pathways;
  d) forming individual expression constructs of the amplified cDNAs wherein the cDNAs are operably linked to a promoter and to a reporter gene, to produce chimeric test patient derived reporters (test PDRs);
  e) forming an addressable array of a first set of expression constructs harboring the amplified cDNAs from the tumor (test PDRs), and in parallel a second set of expression constructs of the cDNAs (wt PDRs);
  f) optionally drying the cDNA constructs on a support solid substrate;
  g) adding viable assay cells to each locus under conditions enabling transfection of the DNA constructs into the assay cells;
  h) allowing expression of the constructs and expression vector in the transfected cells to obtain gene products of the first set of cDNAs from the tumor;
  i) comparing at least one attribute of the chimeric reporter gene in the cells expressing the cDNAs from the tumor with its corresponding wild type expressed cDNAs, wherein a disparate result between the assay cells expressing the cDNA derived from the biological sample of the cancer patient and the corresponding wild type cDNA, is used for identifying the cDNA from the biological sample as a candidate patient specific driver mutation; and
  j) quantifying the disparate result of the candidate patient specific driver mutation to thereby determine the oncogenic grading index of said patient specific driver mutation.

In some embodiments, the method further includes a step incubating the cells with a test drug. In some embodiments, the drug is an anti-cancer drug/agent. In some embodiments, the more than one drug is added to the cells. In some embodiments, a combination (cocktail) of drugs may be added to the cells. In some embodiments, when more than one drug is added to the cells, the drugs may be added concomitantly or sequentially, at any time interval and for any incubation period.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In some embodiments, step g) may precede steps e) and/or f), in which case the assay cells are added to each locus prior to addition of the expression constructs and/or expression vectors.

In some embodiments, the results obtained in the presence of the test compound may be used for determining a curative index, which is indicative of the reduction of the oncogenic index.

According to some embodiments, there is provided a method for determining an oncogenic-related index of extracellular and/or intracellular factors capable of affecting tumoriogenity from a biological sample of a cancer patient, comprising one or more of the steps of (in any appropriate order):
a) adding viable assay cells to a substrate, in an addressable array;
b) adding to the assay cells an expression vector of a Fluorescence Translocation Reporter (FTR) gene comprising a target gene portion linked to a specific reporter gene portion for each locus in the array;
c) adding to the assay cells the biological sample of the patient at specific locuses of the array;
d) comparing at least one attribute of the expressed FTR in the cells to which the biological sample of the patient was added, with the corresponding cells to which the biological sample was not added, wherein a disparate result between the cells to which the biological sample of the patient was added and the corresponding cells to which the biological sample was not added, is used to identifying the factors capable of affecting tumoriogenity; and
e) quantifying the disparate result of the factors capable of affecting tumoriogenity to thereby determine the oncogenic grading index of said factors capable of affecting tumoriogenity.

In some embodiments, the biological sample is selected from patient tumor microenvironment, extracellular fluid, secreted fluid from the tumor, plasma, Bronchoalveolar lavage, and the like, or combinations thereof.

In some embodiments, the factors capable of affecting tumoriogenity are selected from autocrine factors, paracrine factors, or both. In some embodiments, the factors are extracellular factors, intracellular factors, or both. In some embodiments, the factors may be selected from any type of molecule, such as, but not limited to: proteins (for example, growth factors), nucleic acids, and the like.

In some embodiments, the assay cells stably express an FTR. In some embodiments, step b) may precede step a), in which case, the cells are added to the expression vector of the FTR, which is added in an addressable array.

According to some embodiments, there is provided a method of generating and/or determining and/or producing and/or computing an oncogenic index of one or more patient specific mutations, comprising the steps of:
a) forming an addressable array of a first set of expression constructs harboring genes comprising patient specific mutations, and a second set of expression constructs of corresponding wild type genes;
b) adding an expression vector encoding for a Fluorescence Translocation Reporter (FTR) gene comprising a target gene portion linked to a specific reporter gene portion for each locus in the addressable array;
c) adding viable assay cells to each locus under conditions enabling transfection of the expression constructs and expression vectors into the assay cells;
d) comparing the subcellular localization and/or translocation of the expressed FTR in the assay cells expressing the genes comprising the mutation with their corresponding wild type expressed genes to identify a disparate result;
e) quantifying the disparate result of the candidate patient specific mutation, by:
  i) processing the disparate result to determine the degree of translocation of the tested FTR in the presence of the first set of expression constructs and the second set of expression construct to determine activation level of the patient specific mutations;
  ii) normalizing the degree of translocation of the FTR in the presence of the first set of expression vectors, based on the degree of translocation of the FTR in the presence of the second set of expression constructs, to determine normalized activation level of the patient specific mutations; and
  iii) analyzing the mapping/correlation between the normalized activation level of the patient specific mutations and a clinical outcome (reference);
to thereby determine the oncogenic grading index of said patient specific mutation.

According to some embodiments, analyzing may include utilizing machine learning. In some embodiments, analyzing may include such methods as, but not limited to: correlation univariate analysis machine, multi variate analysis machine, support vector machine, generalized linear model machine or combinations thereof.

In some embodiments, the degree of translocation is determined based upon nuclear to cytoplasm ratio (NCR). In some embodiments, clinical outcome references/outcomes may include such references as, but not limited to: clinical trials, clinical results of test labs, clinical results of treatments by health care providers, references of the art, and the like, or combinations thereof.

In some embodiments, the index has a numeric value, indicative of the capacity of the candidate patient specific mutation to drive malignancy.

In some embodiments, the index may be indicative of progression free survival of the patient, overall survival of the patient, probability of drug response, Time to progression (TTP), Tumor response rate, Recurrence, Disease-free survival (DFS).

In some embodiments, the degree of translocation of the patient specific mutation may be further normalized to the impact of the cell signaling pathway in which the patient specific mutation is involved in.

In some embodiments, the patient genes may be derived (directly or indirectly) from a biological sample of the patient. In some embodiments, at least one of the mutations is an oncogenic mutation. In some embodiments, the mutation is a driver mutation. In some embodiments, the patient specific gene(s) may be artificially generated (for example, by synthesis of oligonucleotides), based on the sequence of the gene.

In some embodiments, the first and/or second sets of expression constructs comprise a double stranded linear DNA. In some embodiments, the promoter of the first and/or second set of expression constructs is an inducible or constitutive promoter. In some embodiments, the first and/or second set of expression constructs harbors a portion of a gene. In some embodiments, the method may further include a step of drying the constructs and/or vectors on a solid support in the presence of a transfection reagent.

In some embodiments, step c) may precede step a) and/or step b), in which case the assay cells are added to each locus prior to addition of the expression cassettes.

In some embodiments, the method may further include, a third set of expression constructs of corresponding proteins of the PDMs, which comprises one or more known mutations in said genes (artificial PDMs), that may be used as experimental control. The third set of expression constructs is added to the addressable array.

In some embodiments, the method may further include a step of adding a test drug to the cells. In some embodiments, the method may further include calculating a curative index, indicative of the reduction in the capacity of the patient specific mutation to drive malignant growth in response to the test drug.

According to some embodiments, there is provided a method of generating and/or determining and/or producing and/or computing an oncogenic index of one or more patient specific mutations, comprising the steps of:
 a) adding viable assay cells to a substrate, in an addressable array under conditions enabling transfection of expression constructs and expression vectors into the assay cells;
 b) adding to the assay cells an expression vector of a Fluorescence Translocation Reporter (FTR) gene comprising a target gene portion linked to a specific reporter gene portion for each locus in the array;
 c) adding to the assay cells, at specific locuses of the addressable array, a first set of expression constructs harboring genes comprising patient specific mutations, and adding to the assay cells, at specific locuses a second set of expression constructs of corresponding wild type genes, wherein the first set of expression constructs and the second sets of expression constructs are not added to a common locus;
 d) comparing the subcellular localization and/or translocation of the expressed FTR in the assay cells expressing the genes comprising the mutation(s) with their corresponding wild type expressed genes to identify a disparate result;
 e) quantifying the disparate result of the candidate patient specific mutation, by:
  i) processing the disparate result to determine the degree of translocation of the tested FTR in the presence of the first set of expression constructs and the second set of expression construct to determine activation level of the patient specific mutations;
  ii) normalizing the degree of translocation of the FTR in the presence of the first set of expression vectors, based on the degree of translocation of the FTR in the presence of the second set of expression constructs, to determine normalized activation level of the patient specific mutations; and
  iii) analyzing the mapping/correlation between the normalized activation level of the patient specific mutations and a clinical outcome (reference);
 to thereby determine the oncogenic grading index of said patient specific mutation.

According to some embodiments, there is provided a system for generating an oncogenic grading index, comprising a processing circuitry configured to:
 a) obtain a disparate result indicative of the degree of subcellular translocation of a Fluorescence Translocation Reporter (FTR) gene product in the presence of a first set of expression constructs and in the presence of a second set of expression construct in test cells;
 b) determine activation level of patient specific mutations based on the degree of the subcellular translocation or localization of the FTR;
 c) normalize the subcellular translocation of localization of the FTR in the presence of the first set of expression constructs, based on the degree of translocation of the FTR in the presence of the second set of expression constructs, to determine normalized activation level of the patient specific mutations; and
 d) analyze the correlation/mapping between the activation level of the patient specific mutations and a clinical outcome (reference), to thereby determine the oncogenic index;
 wherein the disparate result is obtained by:
  i) forming an addressable array of a first set of expression constructs harboring genes comprising patient specific mutation(s), and a second set of expression constructs of corresponding wild type genes;
  ii) adding an expression vector encoding for a Fluorescence Translocation Reporter (FTR) gene comprising a target gene portion linked to a specific reporter gene portion for each locus in the addressable array; and
  iii) adding viable assay cells to each locus under conditions enabling transfection of the expression constructs and expression vectors into the assay cells.

In some embodiments, analyzing may include machine learning or any other appropriate computational methods. In some embodiments, analyzing may include correlation univariate analysis, correlation multivariate analysis, support vector machine, generalized linear model analysis or any combination thereof.

In some embodiments, step iii) precedes steps i) and/or ii), in which case the assay cells are added to each locus prior to addition of the expression constructs and/or expression vectors.

In some embodiments, the system may further include adding third set of expression constructs of corresponding proteins of the PDMs, which comprises one or more known driver mutations in said genes (artificial PDMs), that may be used as experimental control. The third set of expression constructs is added to the addressable array.

In some embodiments, the processing circuitry may be further configured to calculating a curative index, indicative of the reduction in the capacity of the patient specific mutation to drive malignant growth in response to the test drug.

According to some embodiments, there is provided a system for generating an oncogenic grading index, comprising a processing circuitry configured to:
 a) obtain a disparate result indicative of the degree of subcellular translocation of a Fluorescence Translocation Reporter (FTR) gene product in the presence of a first set of expression constructs and in the presence of a second set of expression construct in test cells;
b) determine activation level of patient specific mutations based on the degree of the subcellular translocation or localization of the FTR;
c) normalize the subcellular translocation of localization of the FTR in the presence of the first set of expression constructs, based on the degree of translocation of the FTR in the presence of the second set of expression constructs, to determine normalized activation level of the patient specific mutations; and
d) analyze the correlation between the activation level of the patient specific mutations and a clinical outcome (reference), to thereby determine the oncogenic index;
wherein the disparate result is obtained by:
 i) adding viable assay cells to each locus under conditions enabling transfection of the expression constructs and expression vectors into the assay cells;
 ii) forming an addressable array of a first set of expression constructs harboring genes comprising patient specific mutation(s), and a second set of expression constructs of corresponding wild type genes; and
 iii) adding an expression vector encoding for a Fluorescence Translocation Reporter (FTR) gene comprising a target gene portion linked to a specific reporter gene portion for each locus in the addressable array.

According to some embodiments, there is provided a system for generating an oncogenic grading index, comprising a processing circuitry configured to:
a) obtain a disparate result indicative of the degree of subcellular translocation of a Fluorescence Translocation Reporter (FTR) gene product in the presence of a first set of expression constructs and in the presence of a second set of expression construct in test cells;
b) determine activation level of patient specific mutations based on the degree of the subcellular translocation or localization of the FTR;
c) normalize the subcellular translocation of localization of the FTR in the presence of the first set of expression constructs, based on the degree of translocation of the FTR in the presence of the second set of expression constructs, to determine normalized activation level of the patient specific mutations; and
d) analyze the correlation/mapping between the activation level of the patient specific mutations and a clinical outcome (reference), to thereby determine the oncogenic index;
wherein the disparate result is obtained by a process including one or more the following steps:
 i. obtaining a sample of a plurality of mRNAs from a biological sample of the cancer patient, such as from a biopsy of the tumor;
 ii. generating a cDNA library from the plurality of tumor mRNAs, by methods known in the art;
 iii. amplifying individual cDNA samples of the cDNA library using a set of primers complementary to polynucleotides encoding for known proteins, wherein the proteins are involved in various cell signaling pathways;
 iv. forming individual expression constructs of the amplified cDNAs wherein the cDNAs are operably linked to a promoter and to a reporter gene, to produce chimeric test patient derived reporters (test PDRs);
 v. forming an addressable array of a first set of expression constructs harboring the amplified cDNAs from the tumor (test PDRs), and in parallel a second set of expression constructs of the cDNAs (wt PDRs);
 vi. optionally drying the cDNA constructs on a support solid substrate;
 vii. adding viable assay cells to each locus under conditions enabling transfection of the DNA constructs into the assay cells;
 viii. allowing expression of the constructs and expression vector in the transfected cells to obtain gene products of the first set of cDNAs from the tumor;
 ix. comparing at least one attribute of the chimeric reporter gene in the cells expressing the cDNAs from the tumor with its corresponding wild type expressed cDNAs, wherein a disparate result between the assay cells expressing the cDNA derived from the biological sample of the cancer patient and the corresponding wild type cDNA, is used for identifying the cDNA from the biological sample as a candidate patient specific driver mutation; and
 x. quantifying the disparate result of the candidate patient specific driver mutation to thereby determine the oncogenic grading index of said patient specific driver mutation.

According to some embodiments, there is provided a method of generating a curative index indicative of susceptibility to drug treatment of one or more patient specific mutations, comprising the steps of:
a) forming an addressable array of a first set of expression constructs harboring genes comprising patient specific mutations, and a second set of expression constructs of corresponding wild type genes;
b) adding an expression vector encoding for a Fluorescence Translocation Reporter (FTR) gene comprising a target gene portion linked to a specific reporter gene portion for each locus in the addressable array;
c) adding viable assay cells to each locus under conditions enabling transfection of the expression constructs and expression vectors into the assay cells;
d) comparing the subcellular localization and/or translocation of the expressed FTR in the assay cells expressing the genes comprising the mutation with their corresponding wild type expressed genes to in the presence and absence of a drug, to identify a disparate result;
e) quantifying the disparate result of the candidate patient specific mutation, by:
 i) processing the disparate result to determine the degree of subcellular translocation of the tested FTR in the presence of the first set of expression constructs and the second set of expression construct to determine activation level of the patient specific mutations in the presence or absence of the drug;
 ii) normalizing the degree of subcellular translocation of the FTR in the presence of the first set of expression vectors, based on the degree of subcellular translocation of the FTR in the presence of the second set of expression constructs, in the presence or absence of the drug, to determine normalized activation level of the patient specific mutations; and
 iii) analyzing the correlation between the normalized activation level of the patient specific mutations in the presence or absence of the drug, and with a clinical outcome (reference);
to thereby determine the curative index of the drug on the patient specific mutation.

In some embodiments the drug is an anti-cancer drug. In some embodiments, the method may include adding more than one drug, concomitantly or sequentially. In some embodiments, the method may include adding a combination of drugs. In some embodiments, the method may include adding varying concentration of drug(s).

In some embodiments, step c) may precede step a) and/or step b).

According to some embodiments, there is provided a method of generating a curative index indicative of susceptibility to drug treatment of one or more patient specific mutations, comprising the steps of:
a) adding viable assay cells to each locus under conditions enabling transfection of the expression constructs and expression vectors into the assay cells;
b) forming an addressable array of a first set of expression constructs harboring genes comprising patient specific mutations, and a second set of expression constructs of corresponding wild type genes;
c) adding an expression vector encoding for a Fluorescence Translocation Reporter (FTR) gene comprising a target gene portion linked to a specific reporter gene portion for each locus in the addressable array;
d) comparing the subcellular localization and/or translocation of the expressed FTR in the assay cells expressing the genes comprising the mutation(s) with their corresponding wild type expressed genes to in the presence and absence of a drug, to identify a disparate result;
e) quantifying the disparate result of the candidate patient specific mutation, by:
  i) processing the disparate result to determine the degree of subcellular translocation of the tested FTR in the presence of the first set of expression constructs and the second set of expression construct to determine activation level of the patient specific mutations in the presence or absence of the drug;
  ii) normalizing the degree of subcellular translocation of the FTR in the presence of the first set of expression vectors, based on the degree of subcellular translocation of the FTR in the presence of the second set of expression constructs, in the presence or absence of the drug, to determine normalized activation level of the patient specific mutations; and
  iii) analyzing the correlation between the normalized activation level of the patient specific mutations in the presence or absence of the drug, and with a clinical outcome (reference);
to thereby determine the curative index of the drug on the patient specific mutation.

According to some embodiments, there is provided a system for generating a curative index indicative of susceptibility to drug treatment of one or more patient specific mutations, comprising a processing circuitry configured to:
a) obtain a disparate result indicative of the degree of subcellular translocation of a Fluorescence Translocation Reporter (FTR) gene product in the presence of a first set of expression constructs and in the presence of a second set of expression construct in test cells in the presence and absence of a drug or a combination of drugs;
b) determine activation level of patient specific mutations based on the degree of the subcellular translocation or localization of the FTR;
c) normalize the subcellular translocation of localization of the FTR in the presence of the first set of expression constructs, based on the degree of translocation of the FTR in the presence of the second set of expression constructs in the presence or absence of the drug or combination of drugs, to determine normalized activation level of the patient specific mutations; and
d) analyze the correlation/mapping between the activation level of the patient specific mutations and a clinical outcome (reference), to thereby determine the oncogenic index;
wherein the disparate result is obtained by:
  i) forming an addressable array of a first set of expression constructs harboring genes comprising patient specific mutation(s), and a second set of expression constructs of corresponding wild type genes;
  ii) adding an expression vector encoding for a Fluorescence Translocation Reporter (FTR) gene comprising a target gene portion linked to a specific reporter gene portion for each locus in the addressable array; and
  iii) adding viable assay cells to each locus under conditions enabling transfection of the expression constructs and expression vectors into the assay cells.

According to some embodiments, there is provided a system for generating a curative index indicative of susceptibility to drug treatment (drug response) of one or more patient specific mutations, comprising a processing circuitry configured to:
a) obtain a disparate result indicative of the degree of subcellular translocation of a Fluorescence Translocation Reporter (FTR) gene product in the presence of a first set of expression constructs and in the presence of a second set of expression construct in test cells in the presence and absence of a drug or a combination of drugs;
b) determine activation level of patient specific mutations based on the degree of the subcellular translocation or localization of the FTR;
c) normalize the subcellular translocation of localization of the FTR in the presence of the first set of expression constructs, based on the degree of translocation of the FTR in the presence of the second set of expression constructs in the presence or absence of the drug or combination of drugs, to determine normalized activation level of the patient specific mutations; and
d) analyze the correlation/mapping between the activation level of the patient specific mutations and a clinical outcome (reference), to thereby determine the oncogenic index;
wherein the disparate result is obtained by:
  i) adding viable assay cells to each locus under conditions enabling transfection of the expression constructs and expression vectors into the assay cells;
  ii) forming an addressable array of a first set of expression constructs harboring genes comprising patient specific mutation(s), and a second set of expression constructs of corresponding wild type genes; and
  iii) adding an expression vector encoding for a Fluorescence Translocation Reporter (FTR) gene comprising a target gene portion linked to a specific reporter gene portion for each locus in the addressable array.

According to some embodiments, there is provided a system for generating a curative index indicative of susceptibility to drug treatment of one or more patient specific mutations, comprising a processing circuitry configured to:
a) obtain a disparate result indicative of the degree of subcellular translocation of a Fluorescence Translocation Reporter (FTR) gene product in the presence of a first set of expression constructs and in the presence of a second set of expression construct in test cells in the presence and absence of a drug or a combination of drugs;

b) determine activation level of patient specific mutations based on the degree of the subcellular translocation or localization thereof;

c) normalize the subcellular translocation of localization of the FTR in the presence of the first set of expression constructs, based on the degree of translocation of the FTR in the presence of the second set of expression constructs in the presence or absence of the drug or combination of drugs, to determine normalized activation level of the patient specific mutations; and d) analyze the correlation/mapping between the activation level of the patient specific mutations and a clinical outcome (reference), to thereby determine the oncogenic index;

wherein the disparate result is obtained by a process comprising one or more of the following steps (in any order):

i. obtaining a sample of a plurality of mRNAs from a biological sample of the cancer patient, such as from a biopsy of the tumor;

ii. generating a cDNA library from the plurality of tumor mRNAs, by methods known in the art;

iii. amplifying individual cDNA samples of the cDNA library using a set of primers complementary to polynucleotides encoding for known proteins, wherein the proteins are involved in various cell signaling pathways;

iv. forming individual expression constructs of the amplified cDNAs wherein the cDNAs are operably linked to a promoter and to a reporter gene, to produce chimeric test patient derived reporters (test PDRs);

v. forming an addressable array of a first set of expression constructs harboring the amplified cDNAs from the tumor (test PDRs), and in parallel a second set of expression constructs of the cDNAs (wt PDRs);

vi. optionally drying the cDNA constructs on a support solid substrate;

vii. adding viable assay cells to each locus under conditions enabling transfection of the DNA constructs into the assay cells;

viii. allowing expression of the constructs and expression vector in the transfected cells to obtain gene products of the first set of cDNAs from the tumor;

ix. comparing at least one attribute of the chimeric reporter gene in the cells expressing the cDNAs from the tumor with its corresponding wild type expressed cDNAs, wherein a disparate result between the assay cells expressing the cDNA derived from the biological sample of the cancer patient and the corresponding wild type cDNA, is used for identifying the cDNA from the biological sample as a candidate patient specific driver mutation; and x. quantifying the disparate result of the candidate patient specific driver mutation to thereby determine the oncogenic grading index of said patient specific driver mutation.

According to some embodiments, the expression constructs used in the methods and systems disclosed herein may be obtained by a process comprising one or more of the following steps:

i) generating a cDNA library from a plurality of mRNAs obtained from the biological sample of the patient;

ii) amplifying specific cDNAs of the cDNA library using a set of primers complementary to polynucleotides encoding for genes suspected of harboring an oncogenic mutation; and iii) operably linking the amplified cDNAs to a promoter.

In some embodiments, the patient's genes or gene portions, suspected of harboring one or more mutations, may be synthesized by methods known in the art and optionally be operably linked to a promoter to obtain the expression constructs. In some embodiments, the patient genes (or portions thereof) and/or the corresponding wild type (WT) genes may be artificially synthesized, based on their sequence and further processed to generate the corresponding PDMs, as detailed herein.

According to some embodiments, the identified mutations along with the data regarding the mutation, together with the data obtained regarding paracrine/autocrine activated pathways may be used to generate a "tumor oncogenic map", which indicates the affected signaling pathways within the patient tumor as well as the mutated genes and the oncogenic activity thereof. In some embodiments, the tumor oncogenic map is composed of the summary of the individual oncogenic indexes of the tested genes. In some embodiments, the mutation is an oncogenic mutation. In some embodiments, the mutation is a driver mutation.

According to some embodiments, after identification of the patient specific mutations and the signaling pathways involved (i.e., the generation of the tumor oncogenic map), a second testing may be performed, wherein the second test assay is performed in the presence of a treatment, such as, targeted therapy drug/agent/composition known to inhibit/affect the identified pathways/mutations. A drug/agent/composition having an effect on the oncogenic index of the patient tumor may thus be determined. In some embodiments, the change in the oncogenic activity induced by the tested drug/agent/composition is referred to herein as "Curative index".

In some embodiments, the various drug/agents treatments and their respective curative index may be superimposed on the "tumor oncogenic map" and provide the health care provider with the patient specific underlying molecular tumor mechanism and the treatment options and their respective expected efficacy for treating the specific patient.

According to some embodiments, there is thus provided a method for identifying a candidate treatment capable of affecting the oncogenic index of the patient specific tumor, the method comprising identifying a patient specific driver mutation (by any of the methods disclosed herein) and testing the effect of the candidate drug on the patient specific driver mutation in biological sample of the patient (by any of the methods disclosed herein). In some embodiments the candidate treatment is a drug, an agent, a composition or any type of treatment.

According to some embodiments, there is provided a method for determining an oncogenic index, the oncogenic index is indicative of the capacity of a given identified oncogenic mutation/aberration (PDR/PDM) to drive malignant growth within a given patient tumor sample, the method comprising calculating/computing/determining the degree of translocation of the tested FTR/PDR which is calibrated/normalized to infer the impact of the tested PDM on malignant growth. According to some embodiments the oncogenic index has a numeric value, wherein the higher the value is, the higher the oncogenic index of the tested FTR/PDR is. In some embodiments, the oncogenic index is in the range of 1-100. In some embodiments, the oncogenic index is in the range of 1-50. In some embodiments, the oncogenic index is in the range of 1-10. In some embodiments, the oncogenic index is in the range of 0-10. In some embodiments, the oncogenic index is in the range of 0-5. In some embodiments, the oncogenic index is in the range of 0-1.

According to some embodiments, the term "oncogenic index" and "oncogenic grading index" may be interchangeably used. The terms are directed to a value indicating the capacity of a given oncogenic mutation/aberration to drive malignant growth within a given patient tumor sample.

According to some embodiments, each gene identified as harboring an oncogenic mutation is assigned an oncogenic index that can enable severity comparison between the different identified driver mutations of the tumor.

According to some embodiments, the term "total oncogenic index" is directed to a value indicative of the total capacity of all identified mutations in all signaling pathways to drive malignant growth within a given patient tumor sample. In some embodiments, the total oncogenic index may be calculated by summing all of oncogenic indexes of the identified mutated genes, and is indicative of the overall severity of the disease.

According to some embodiments, the term "Curative Index" is directed to a value (such as a numeric value), which reflects the change in the oncogenic index, produced by one or more anti-cancer treatments (such as drug treatment) of the patient tumor.

According to some embodiments, the term "total curative index" is directed to a value (such as a numeric value), that sums the overall change in the total oncogenic index, produced by a full combinatorial drug treatment of the patient tumor.

In some embodiments, the curative index may be calculated based on the oncogenic index of a specific tested gene, a set of genes or combination of genes, and the change of this index (either reduction/no change/enhancement depending on the nature of the effect) by treatment of the tested cells with a test compound (such as a small molecule, a therapeutic antibody, and the like). If the test compound can induce reduction in the oncogenic index of the tested cells (i.e. there is a reduction in the oncogenic signaling measured by this gene), this results in a high curative index.

According to some embodiments, the term "Metastatic index" is directed to a value (such as a numeric value) which is indicative of the capacity of a given mutation/aberration to drive cell dissociation form a tumor or cell penetration/adhesion in a distal location from the primary tumor site. In some embodiments, the term "total metastatic index" is directed to a value (such as a numeric value) that sums the overall metastatic indexes of the identified mutated genes, and is indicative of the overall metastasis potential of the disease According to some embodiments, the term "angiogenic index" is directed to a value (such as a numeric value) which is indicative of the capacity of a given mutation/aberration to drive blood vessel formation/development/branching/penetration, within a tumor to support tumor burden/tumor growth. According to some embodiments, the term "total angiogenic index" is directed to a value (such as a numeric value) that sums the overall angiogenic indexes of the identified mutated genes.

According to some embodiments, the term "genomic instability index" is directed to a value (such as a numeric value) which is indicative of the capacity of a given mutation/aberration to inhibit DNA repair or stimulate DNA mutations and their establishment within the tumor or as a somatic mutation driving tumor growth or stimulating additional tumor similar or different to the original tumor. In some embodiments, the term "total genomic instability index" is directed to a value (such as a numeric value) that sums the overall genomic instability indexes of the identified mutated genes.

According to some embodiments, the term "Microtubule dynamic instability index" is directed to a value (such as a numeric value), which is indicative of the capacity of a given mutation/aberration on activity or stabilization of microtubule system or other cytoskeletal system to drive tumor growth. In some embodiments, the mutation/aberration may be selected from: protein conformational state in microtubule proteins/microtubule binding proteins, dynamic instability, or other cytoskeleton proteins that can stimulate cell division or be resistant to mitotic inhibitors or other microtubule or cytoskeletal drugs that stabilize the microtubule system or other cytoskeletal system and can thus drive tumor growth. In some embodiments, the term "total microtubule dynamic instability index" is directed to a value (such as a numeric value) that sums the overall Microtubule dynamic instability indexes of the identified mutated genes.

According to some embodiments, the term "cell cycle progression index" is directed to a value (such as a numeric value) which is indicative of the capacity of a given mutation/aberration to affect cell cycle progression.

According to some embodiments, the term "apoptopic index" is directed to a value (such as a numeric value) which is indicative of the capacity of a given mutation/aberration to affect cell apoptosis.

According to some embodiments, the term "differentiation index" is directed to a value (such as a numeric value) which is indicative of the capacity of a given mutation/aberration to affect cellular differentiation.

According to some embodiments, one or more of the oncogenic-related indexes disclosed herein, determined/calculated/computed based on the methods and systems disclosed herein, may be used for identifying, determining and/or recommending a patient specific treatment that can provide the best therapeutic effect for the patient.

According to some embodiments, the methods and systems used for generating the various indexes, may utilize various calculation techniques, such as, for example, machine learning techniques. In some embodiments, machine learning techniques may include such techniques as, but not limited to: Correlation Analysis, Support Vector Machines, Generalized Linear Models, and the like, or combinations thereof.

According to some embodiments, a first step in the calculations for generating indexes is a normalization step (preprocessing). In some embodiments, the normalization step includes providing a reference value. In some exemplary embodiments, determination of the patient's specific mutations and mutated signaling pathways activation levels (by the systems and methods described herein), may be expressed in units of Nucleus to Cytoplasm Ratio (NCR). Hence, a normalization step may include determining the raw NCR of the wild-type (WT) sample/reference (for example, the WT-PDM) is arbitrarily set to a reference value (for example, zero), and each of the measured NCR of the tested PDM ("test NCR") is given a value which is relative to this WT reference. Additionally, or alternatively, each measured test NCR can be relative to a relevant fixed reference and normalized to its units (for example, such that the reference is always 100).

In some embodiments, the normalization step may be followed by a suitable machine learning method (or any other suitable computational system), to learn the function that maps/correlates the actual results obtained from the various biological assay outputs (i.e. testing of patients genes by the methods and systems disclosed herein and determining the activation levels thereof), to a clinical reference/outcome, to provide a clinically relevant index. In some embodiments, clinical outcome references/outcomes may include such references as, but not limited to: clinical trials, clinical results of test labs, clinical results of treatments by health care providers, references of the art, and the like, or combinations thereof.

According to some embodiments, the resulting index depends on the input (data) provided for generating the index and hence, the clinical significance of the index relies upon the input. In some embodiments, when using the biological assay outputs for determining activation levels of the patient specific genes, together with an observed progression free survival, the resulting oncogenic index is the progression free survival index (i.e., the generated index indicates/predicts the progression free survival of the patient, based on the patient specific mutations). In some embodiments, if the input (data) is the biological assay outputs for the patient specific genes, in the presence and absence of a drug, together with measured response to a drug in the clinic, the resulting index is an indicator/predictor of the drug response. In some embodiments, the calculated indexes are quantitative.

According to some embodiments, an index may be generated based on the data obtained from the biological assays (i.e., determining levels of activation of various patient specific PDMs) without the input of additional clinical reference/outcomes.

According to some embodiments, the systems disclosed herein may include any suitable hardware, firmware, or software, such as, a processing circuitry (including a processing logic, a processing unit, a processor, and the like), a non-transitory memory, having stored thereon computer-readable instruction executable by said processing circuitry to perform any of the required steps for generating an index, and the like, or combinations thereof.

According to some embodiments, a patient is a patient afflicted with cancer. In some embodiments, cancers include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocytoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer is selected from prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer.

In some embodiments, the patient has been diagnosed positive for cancer. In some embodiments, the patient is subjected to targeted therapy treatment regimen with known or unknown treatment results. In some embodiments, the patient has an available patient tumor molecular profiling (IHC, FISH, PCR and sequencing). In some embodiments, the patient has available patient history as well as outcome (patient response, resistance, recurrence and survival rates).

In some embodiments, the biological sample is selected from: blood, serum, biopsy, tissue, needle biopsy, bronchoalveolar lavage, pleural effusion urine, saliva and tumor. In some embodiments, the biological sample may be freshly isolated. In some embodiments, the biological sample may be frozen. In some embodiments, the biological sample may be fixed.

In some embodiments, each protein expressed in an assay cell (such as, tested PDM, FTR, WT PDM, PDR) is differentially identifiable. In another embodiment, each protein, directly or indirectly, may be identified by a different marker or reporter or a different fluorescent protein. In another embodiment, each chimeric protein (such as, FTR, or PDR) comprises a different reporter moiety. In another embodiment, different proteins may share a fluorescent protein or reporter. In another embodiment, each chimera protein of the invention comprises a different reporter moiety.

In another embodiment, a PDM is associated with cancer growth. In another embodiment, a PDM is an oncogene or tumor suppressor. In another embodiment, a PDM is a cytoskeletal regulator. In another embodiment, a PDM has a role in tumor growth and metastasis. In another embodiment, a PDM is a vesicle trafficking protein. In another embodiment, a PDM is a vesicle tethering protein. In another embodiment, a PDM is a cell adhesion protein. In another embodiment, a PDM is a nuclear integrity protein. In another embodiment, a PDM is a growth factor receptor. In another embodiment, a PDM is a cytokine receptor. In another embodiment, a PDM is a cell attachment protein. In another embodiment, a PDM is involved in tumor inflammation. In another embodiment, a PDM is a cell polarity protein. In another embodiment, a PDM is a signaling protein. In another embodiment, a PDM is an adaptor protein. In another embodiment, a PDM is a protein kinase. In another embodiment, a PDM is an exchange factor. In another embodiment, a PDM is a cytoskeletal protein. In some exemplary embodiments, a PDM is selected from the group comprising or consisting of: AKT1, AKT2, AKT3, ALK, BRAF, BRCA1, BRCA2, CBL, CTNNB1, EGFR, ERBB2, ERBB3, FGFR1, FGFR2, GNA11, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, ESR1, AR, PR, DDR2, MEK1 or any combination thereof. Each possibility is a separate embodiment.

In another embodiment, a PDM may be expressed in conjunction to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1). In some embodiments, the marker comprises a marker motif of Cys-Cys-Pro-Gly-Cys-Cys (SEQ ID NO:47), and prior to imaging to FlAsH-EDT2 or ReAsH-EDT2 may be added to the test assay, to become fluorescent upon binding to recombinant proteins containing the Cys-Cys-Pro-Gly-Cys-Cys motif. In some embodiments, the protein comprising the Cys-Cys-Pro-Gly-Cys-Cys may be the PDM, a fluorescent protein alone, or a fluorescent protein fused to a subcellular marker that can further be used to tag subcellular organelles, such as, for example, plasma membrane or nucleus. In some embodiments, the marker (tag) expressed in conjunction to the PDM is used as a marker to verify transfection and expression of the PDM is an assay cell.

In another embodiment, a PDR is a PDM fused to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1. In some embodiments, a PDR is a PDM fused to marker (tag), comprising a Cys-Cys-Pro-Gly-Cys-Cys (SEQ ID NO:47) motif.

In some embodiments, the FTR is a fusion (chimeric) protein comprising a reporter portion, such as a fluorescent marker (fluorescent protein, such as mCherry, mApple, GFP, Cherry, DsRed, RFP, EGFP, BFP, YFP, AmCyan1, ZsGreen1, ZsYellow1, DsRed2, AsRed2, and HcRed1) or a Cys-Cys-Pro-Gly-Cys-Cys motif (SEQ ID NO:47), and a target protein portion selected from, but not limited to: a protein associated with cancer growth, an oncogene product, a cytoskeletal regulator, vesicle trafficking protein, vesicle tethering protein, cell adhesion protein, nuclear integrity protein, growth factor receptor, cell attachment protein, cell signaling protein, protein involved in tumor inflammation, cell polarity protein, growth factor signaling protein, an adaptor, a cytoskeletal protein, and the like. Each possibility is a separate embodiment.

In some exemplary embodiments, the FTR is a fusion protein comprising a reporter portion, such as a fluorescent protein, and a target (marker) protein portion selected from the group comprising or consisting of, but not limited to: AKT1, AKT2, mTOR, RelA, NFKB1, NFKB2, ERK1, ERK2, ERF, STAT1, STAT3, STAT5, CTNNB1, JNK1alpha, JNK1beta, JNK2alpha, JNK2beta, ERK5, P38alpha, P38beta, AMPK, STK11, SMARCA4, TP53, ESR1, GATA3, CDK2, SMAD1, NOTCH1, MYB, MYC, SMAD2, SMAD3, SMAD4, PRKACA, NLK or any combination thereof. Each possibility is a separate embodiment.

In some exemplary embodiments, the PDM may be KRas and the target portion of the FTR may be selected from: ERK2, ERF, JNK and AKT1. Each possibility is a separate embodiment.

In some exemplary embodiments, the PDM may be AKT2 or AKT3 and the target portion of the FTR may be selected from: AKT1 and RelA. Each possibility is a separate embodiment.

In some exemplary embodiments, the PDM may be FGFR1 and the target portion of the FTR may be selected from: ERK2, JNK (such as JNK1alpha 1), p38b, AKT1 and STAT3. Each possibility is a separate embodiment.

In some exemplary embodiments, the PDM may be BRaf and the target portion of the FTR may be selected from: ERK2 and ERF. Each possibility is a separate embodiment.

In some exemplary embodiments, the PDM may be EGFR and the target portion of the FTR may be selected from: ERK2, RelA, AKT1, p38b, JNK1a1. Each possibility is a separate embodiment.

In another embodiment, the invention includes assay cells, wherein each assay cell expresses a PDM and/or an FTR. In another embodiment, the invention includes assay cells, wherein each assay cell expresses a different PDM and/or an FTR and/or PDR. In another embodiment, the invention includes assay cells, wherein each assay cell is transfected with a different DNA fragment, wherein each DNA fragment encodes a different PDM and/or an FTR. In some embodiments, the assay cells are placed/plated/grown on solid substrate having designated locuses (locations). In some embodiments, the assay cells are identical for each locus. In some embodiments, the assay cells are not identical for each locus. In some embodiments the assay cells are added in medium to each locus. In some embodiments, the cells are added to a solid substrate already having DNA constructs dehydrated thereto. In some embodiments, the cells are first plated on the solid substrate and transfected after a predetermined period of time.

In another embodiment, the invention includes assay cells, wherein each assay cell is transfected with a different DNA fragment, wherein each DNA fragment encodes a different PDM and/or an FTR and/or PDR.

In some embodiments, identification of localization of the FTR is performed using a protein assay, binding assay, an immunoassay, microscopic imaging, or any other suitable assay known to those of skill in the art. In some embodiments, activation levels of a test PDM may be determined based on the nucleus to cytoplasm ratio (NCR) of the FTR.

In some embodiments, the invention further includes the step of detecting a morphological change in an assay cell. In some embodiments, the methods of the invention do not require sequencing of any patient DNA.

According to some embodiments, the method may further include adding a test drug to the cells, and identifying effect of the drug on the translocation of the FTR under various experimental conditions.

According to some embodiments, the drug is an anti-cancer drug. In some exemplary embodiments, the drug may be selected from, but not limited to: Brentuximab vedotin, cabozantinib, carfilzomib, cetuximab, crizotinib, dabrafenib, dasatinib, denosumab, Erlotinib, Everolimus, gefitinib, ibritumomab tiuxetan, Ibrutinib, imatinib mesylate, ipilimumab, lapatinib, nilotinib hydrochloride monohydrate, obinutuzumab, ofatumumab, panitumumab, pazopanib, pertuzumab, ponatinib, Regorafenib, Rituxan, sorafenib, sunitinib, temsirolimus, trametinib, trastuzumab, vandetanib, vemurafenib, vismodegib, ziv-aflibercept.

According to some embodiments, the drug(s) may be added to the test cells at any desired amount/concentration. For example, the drug may be added at a concentration of: 1 nM to 1 mM.

According to some embodiments, the drug(s) may be added and incubated with the test cells for any desired period of time, such as for example, in the range of: 10 minutes to 24 hours.

According to some embodiments, there is provided a kit for diagnosing cancer in a patient. In some embodiments, there is provided a kit for identifying an aberrant cellular signaling pathway in tumor cells. In some embodiments, there is provided a kit for identifying patient specific driver mutations. In some embodiments, there is provided a kit for determining/detecting/identifying drug response of patient specific driver mutations. In some embodiments, there is provided a kit for measuring the response/resistance of patient mutant genes to drug therapies. According to some embodiments, there is provided a kit for generating/determining various oncogenic related indexes of patient specific oncogenic mutations.

In some embodiments, the invention provides a kit for diagnosing cancer or the molecular cancer profile in a subject, by identifying patient specific driver mutations. The kit can be used, according to some embodiments, for predicting treatment success or identifying paracrine or autocrine factors involved in cancer. In another embodiment, the kit comprises at least one means of detecting a reporter gene. In another embodiment, the kit comprises means for detecting a marker. In some embodiments, the kit contains one or more of: a substrate or container for holding nucleic acid molecules and/or test cells, directions for carrying out detection/translocation assay(s), test cells, transfection reagents, or any combination thereof.

Diagnostic compositions of the present invention may, if desired, be presented in an article of manufacture e.g., kit, such as an FDA approved kit, which may contain diagnostic reagents and instructions for use. The kit may also be accommodated by a notice associated with the container in a form prescribed by a governmental agency regulating the manufacture, use or sale of pharmaceuticals, which notice is reflective of approval by the agency of the form of the compositions or human or veterinary use.

In another embodiment, the methods and kits of the invention increase survival of cancer patients. The assays of the present invention are ideally suited for the preparation of kits. Such a kit may comprise a carrier means being compartmentalized to receive in close confinement there with one or more container means such as vials, tubes, plates, slides, and the like, each of the container means comprising the separate elements of the cell assay.

In one embodiment, a kit for diagnosing cancer in a subject comprising a panel of assay cells each includes a different protein of the invention is provided, the kit comprising a substrate having nucleic acid molecules encoding for PDM (derived from a biological sample of the patient) and/or FTR and/or FTR, wherein the substrate is further capable of holding assay cells and a biological sample isolated from a human subject suspected of having cancer and printed instructions for reacting measuring and or detecting translocation events.

In some embodiments, transfected assay cells are cultured under effective conditions, which allow for the expression of recombinant protein or tagged proteins. In one embodiment, a tagged or marker protein of the invention (such as PDM, FTR) is a recombinant protein or a chimera. In some embodiments, effective culture conditions include, but are not limited to, effective media, bioreactor, temperature, $CO_2$, pH and oxygen conditions that permit protein expression. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, the present invention utilizes redistribution technology for monitoring and recording protein translocation event. In another embodiment, protein targets are labeled with the green fluorescent protein or other fluorescent proteins, and stably or transient transfected cell lines are generated. In another embodiment, the assays of the invention are read using a high-throughput, optical microscope-based instrument.

In another embodiment, protein translocation assay of the invention is high-content, high-throughput assay primarily used for profiling of lead series, primary screening of PDMs derived from biological samples as a constituent of cell media. In another embodiment, a protein translocation assay of the invention includes live-cell imaging, using Spinning Disc technology or any other microscopy based technology.

In some embodiments, a toponomic localization technique is used to follow and record protein translocation events. In some embodiments, means of immunofluorescence, of proteins of the invention, are utilized. In some embodiments, proteins of the invention are labeled with fluorescent markers. In some embodiments, confocal microscopic images are assessed and processed. In another embodiment, a standard dataset included 2-40 images of each cell per biological condition. In another embodiment, automated image analysis is performed. In another embodiment, automated image analysis includes cellular compartment or structure identification.

In another embodiment, spatial relations are captured in different dimensionalities. In another embodiment, quantitative assessment of protein-marker concentrations in bounded regions is performed. In another embodiment, the present invention further provides protein co-localization studies, based on measuring and evaluating isotropic distributions of distances between pixels. In another embodiment, the present invention provides a 2-dimensional analysis (regions). In another embodiment, the present invention further provides a 0-dimensional analysis (points). In another embodiment, the present invention provides 1-dimensional modeling.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "about" in reference to a numerical value stated herein is to be understood as the stated value+/−10%.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate some embodiments of the invention. They should, in no way be construed, however, as limiting the broad scope of the invention.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Biological Sample Collection

Both formalin fixed paraffin embedded (FFPE) tumor biopsies as well as frozen fresh tumor parts or biopsies are collected. The FFPE samples are used to extract specific genomic exons that are known to be involved in cancer progression (such as cKit exon 11). The fresh (fresh or fresh frozen) biopsy is used for both mRNA extraction and interstitial fluid extraction.

Thus, both retrospective and prospective samples are collected. Retrospective study based on frozen tumor sections from cases that the treatment efficacy is known.

Prospective study based on fresh or snap frozen sample/biopsy tissue/tumor section collected immediately following surgery/biopsy/bronchoscopy. This enables amplification of all relevant tested proteins (such as oncogenes or indicators). Other body fluids such as plasma samples (using Heparane sulfate gel tubes), blood samples, peritoneal fluid, pleural effusion and lung fluids obtained through bronchoscopy are of great importance as they accumulate much of the tumor secretions and are also collected.

Following tumor resection (surgery, biopsy, Bronchoscopy), the tumor tissue is placed in a sterile bag or tube on ice (not treated with formalin). A pathologist subdivides the tumor (taking into account size and location of viable tumor section) to those required for fixation and those best representing the tumor that are delivered fresh on ice for further analysis. The pathologist identifies a tissue section or area enriched with malignant cells and with reduced amount of stroma or other non-malignant tissue and excises it. If the net weight of the tissue exceeds 1 grams, tissue is further cut to several pieces and placed on a cellulose column and spun at 100 g for 10 min (100±50 microliter of IF are expected from every gram of tissue). Tissue is then transferred to another 15/50 ml tube and frozen in a −80° C. freezer. Spun down liquid known as the Interstitial fluid (IF) are frozen in original tube.

Needle biopsy—Tissue is placed in a 15 conical tube and frozen in a −80 freezer.

Biopsy via Bronchoscopy—Tissue is placed in a 15 conical tube and frozen in a −80 freezer.

Bronchoalveolar lavage—Extracted liquid is split between 2 50 ml falcon tubes and Spun down (3000 RPM, 15 min.). Liquid is transferred into new tubes and both liquid and cells (in original tubes) are frozen at −80° C.

Pleural effusion—Pleural effusion is spun down (3000 RPM, 15 min.), liquid transferred into new tubes and both liquid and cells (in original tubes) frozen at −80° C.

Cryosection—if possible the tumor is frozen in a microtome and sectioned.

Extraction of Genomic DNA from Formalin Fixed Embedded Tumor Biopsies

To identify genes in which known mutations are present in specific exons, such as cKit mutations in exon 11, EGFR exons 19, 20, HER2 exon 20, DNA extracted from FFPE tissue is used. To this aim, standard DNA extraction kits and protocols are used (for example, Qiagen QIAamp DNA FFPE Tissue, cat. #56404).

Amplification of Exons and Insertion to Full Length Gene

To express desired exons, amplification from the genomic DNA is performed and insertion of the exon into the full length gene lacking this exon. To this aim, full length genes lacking the exon in expression ready vectors are produced and then the exon is incorporated into the construct using conventional molecular biology techniques.

Fresh Biopsies: Extraction of the Needed Amount of Tissue from Frozen Biopsy

A fraction of the biopsy is used for RNA purification and interstitial fluid extraction. The rest of biological material is stored for future reference or additional analysis (Immunohistochemistry (IHC), FISH, and the like).

Extraction of Interstitial Fluid (IF)

The interstitial fluid (IF) extracted as detailed below, is stored for later use as an agonist to the tested cells, to detect the presence of agents that are secreted by the tumor cells and may confer resistance to anti-cancer drugs.

IF extraction is performed by centrifuging the tissue sample in a column with glass fiber filter at 4° C. for 7 min at 1500 g. The fluids are then collected from the bottom part of the column into a new tube.

Extraction of mRNA mRNA extracted from the sample is needed for the amplification of the patient derived markers (PDMs), i.e. genes that are known oncogenes and potentially harbor mutations that provide the cell with oncogenic properties (genes with potential of harboring driver mutations). Exemplary genes that are tested include: AKT1, AKT2, AKT3, ALK, BRAF, BRCA1, BRCA2, CBL, CTNNB1, EGFR, ERBB2, ERBB3, FGFR1, FGFR2, GNA11, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, AR, PR, ESR1, DDR2, MEK1, and MEK2.

RNA extraction is performed by methods known in the art, including the Guanidium-Cesium Chloride Method, Guanidium Acid-Phenol Method and glass fiber filters that bind nucleic acids in the presence of chaotropic salts and/or by use of commercially available kits (such as Qiagen RNeasy kit cat #74106, in accordance with manufacturer instructions).

Generation of cDNA

To allow amplification of PDMs, cDNA is synthesized based on the mRNA extracted from the tissue. cDNA is synthesized based on the template mRNA using a RNA-dependent DNA polymerase reverse transcriptase enzyme and using oligo-dT primers, random hexameric primers, or specific primers. Exemplary protocol includes using SuperScript™ III First-Strand Synthesis SuperMix protocol (Life technologies, cat #18080-051).

Generation of Test PDMs

The generation of the test PDMs is performed in two steps: amplification of the selected PDMs and attachment of additional elements to allow their proper expression in the assay cells.

In a direct approach, a preliminary PCR reaction containing the oligonucleotides related to the test PDMs that are amplified is performed, to allow over-representation of these selected genes within the cDNA sample. In an indirect approach, the test PDM is artificially synthesized, based on the sequence of the specific test PDM, and this artificial PDM may be used as a template for a PCR reaction, using the appropriate primers.

In some examples, the cDNA sample is aliquoted into separate wells/tubes for each gene that is to be amplified.

Using primers designed for each PDM, a PCR reaction is performed to amplify the selected PDM gene from the cDNA library, or based on an artificially generated template PDM.

The following sets of primers are used for the PCR amplification of the following tested PDMs (Table 1):

TABLE 1

| PDM (name) | Accession number | 5' primer | 3' primer |
|---|---|---|---|
| AKT1 (v-akt murine thymoma viral oncogene homolog 1) | NM_001014431.1 | ATGAGCGACGTGGCTATTG T (SEQ ID NO: 1) | TCAGGCCGTGCCGCTGGC (SEQ ID NO: 2) |
| AKT2 (v-akt murine thymoma viral oncogene homolog 2) | NM_001626.4 | ATGAATGAGGTGTCTGTCA TCAAAG (SEQ ID NO: 23) | TCACTCGCGGATGCTGG (SEQ ID NO: 24) |
| AKT3 (v-akt murine thymoma viral oncogene homolog 3) | NM_005465.4 | ATGAGCGATGTTACCATTG TG (SEQ ID NO: 25) | TTATTCTCGTCCACTTGCA GAG (SEQ ID NO: 26) |
| BRAF (v-raf murine sarcoma viral oncogene homolog B) | NM_004333.4 | ATGGCGGCGCTGAGCGGTG ((SEQ ID NO: 3) | TCAGTGGACAGGAAACGC AC (SEQ ID NO: 4) |
| EGFR (Epidermal growth factor) | NM_005228.3 | ATGCGACCCTCCGGGACG (SEQ ID NO: 5) | TCATGCTCCAATAAATTCA CTGCT (SEQ ID NO: 6) |
| HRAS (Harvey rat sarcoma viral oncogene homolog) | NM_005343.2 | ATGACGGAATATAAGCTGG TGGT (SEQ ID NO: 7) | TCAGGAGAGCACACACTT GC (SEQ ID NO: 8) |
| MEK1 (mitogen-activated protein kinase kinase 1) | NM_002755.3 | ATGCCCAAGAAGAAGCCG AC (SEQ ID NO: 9) | TTAGACGCCAGCAGCATG G (SEQ ID NO: 10) |

TABLE 1-continued

| PDM (name) | Accession number | 5' primer | 3' primer |
|---|---|---|---|
| NRAS (neuroblastoma RAS viral (v-ras) oncogene homolog) | NM_002524.4 | ATGACTGAGTACAAACTGG TGGT (SEQ ID NO: 11) | TTACATCACCACACATGGC A (SEQ ID NO: 12) |
| PDGFRA (platelet-derived growth factor receptor, alpha polypeptide) | NM_006206.4 | ATGGGGACTTCCCATCCGG (SEQ ID NO: 13) | TTACAGGAAGCTGTCTTCC ACC (SEQ ID NO: 14) |
| PIK3CA (phosphatidylino-sitol-4,5-bisphosphate 3-kinase, catalytic subunit alpha) | NM_006218.2 | ATGCCTCCACGACCATCAT C (SEQ ID NO: 15) | TCAGTTCAATGCATGCTGT T (SEQ ID NO: 16) |
| PTEN (phosphatase and tensin homolog) | NM_000314 | ATGACAGCCATCATCAAAG AGA (SEQ ID NO: 17) | TCAGACTTTTGTAATTTGT GTATGC (SEQ ID NO: 18) |
| RAF1 (v-raf-1 murine leukemia viral oncogene homolog 1) | NM_002880.3 | ATGGAGCACATACAGGGA GC (SEQ ID NO: 19) | CTAGAAGACAGGCAGCCT CG (SEQ ID NO: 20) |
| TP53 (tumor protein p53) | NM_000546.5 | ATGGAGGAGCCGCAGTCA (SEQ ID NO: 21) | TCAGTCTGAGTCAGGCCCT T (SEQ ID NO: 22) |
| FGFR1 (Fibroblast growth factor 1) | NM_023110.2 | ATGTGGAGCTGGAAGTGC (SEQ ID NO: 27) | TCAGCGGCGTTTGAGTC (SEQ ID NO: 28) |
| FGFR2 (Fibroblast growth factor 2) | NM_000141.4 | ATGGTCAGCTGGGGTCG (SEQ ID NO: 29) | TCATGTTTTAACACTGCCG TTTATG (SEQ ID NO: 30) |
| KRAS (Kirsten rat sarcoma viral oncogene homolog) | NM_004985.3 | GCCTGCTGAAAATGACTGA ATATAAAC (SEQ ID NO: 31) | TTACATAATTACACACTTT GTCTTTGACTTC (SEQ ID NO: 32) |
| SMAD2 (SMAD family member 2) | NM_005901.5 | ATGTCGTCCATCTTGCCAT TC (SEQ ID NO: 33) | TTATGACATGCTTGAGCAA CG (SEQ ID NO: 34) |

Once the PDM gene regions are amplified, a second PCR reaction is performed to add to the 5' end of each PDM gene sequence, a promoter (either constitutive promoter such as CMV or an inducible promoter such as tetracycline promoter) and to the 3' end an IRES followed by a fluorescent reporter gene (such as GFP, RFP, BFP, or any other reporter gene, as designated).

In some examples, the addition of the promoter and IRES+fluorescent reporter elements is performed by molecular biology cloning tools, by fusing the PCR products to the desired elements by PCR approaches, ligation enzymes or recombination approaches (such as T4 DNA ligase or InFusion enzymes (Clontech), respectively).

When the full length nucleic acid molecule is formed (i.e. 5' promoter-PDM-3'IRES+Reporter (or any other order of these elements)), amplification using a PCR reaction is performed, to obtain sufficient amount of the nucleic acid molecule for transfection into cells.

In some cases, amplification of the nucleic acid molecule is achieved by ligating the full length nucleic acid molecule into an appropriate expression vector and transformation into bacteria. Plasmids thus formed are extracted using standard plasmid extraction kits such as Qiagen QIAprep Miniprep kit. In some case, the linear PCR fragments of the various PDMs are used for transfection into test cells.

Generation of FTRs:

The following sets of primers were used for the PCR amplification of the target portions of the following FTRs (Table 2):

TABLE 2

| FTR (name) | Accession number | 5' primer | 3' primer |
|---|---|---|---|
| AKT1 (v-akt murine thymoma viral oncogene homolog 1) | NM_001014431.1 | ATGAGCGACGTGGC TATTGT (SEQ ID NO: 1) | TCAGGCCGTGCCGCT GGC (SEQ ID NO: 2) |
| ERK2 (mitogen-activated protein kinase 1) | NM_002745.4 | ATGGCGGCGGCGGC GG (SEQ ID NO: 35) | TTAAGATCTGTATCCT GG (SEQ ID NO: 36) |
| ERF (Ets2 repressor factor) | NM_006494.2 | ATGAAGACCCCGGC GGACAC (SEQ ID NO: 37) | TCAGGAGTCTCGGTG CTCC (SEQ ID NO: 38) |
| JNK1a1 (mitogen-activated protein kinase 8 alpha 1) | NM_002750.3 | ATGAGCAGAAGCAA GCG (SEQ ID NO: 39) | TCACTGCTGCACCTG TGC (SEQ ID NO: 40) |
| RelA (v-rel avian reticuloendotheliosis viral oncogene homolog A) | NM_021975.3 | ATGGACGAACTGTT CCCCCT (SEQ ID NO: 41) | TAGGAGCTGATCTGA CTCAGC (SEQ ID NO: 42) |
| P38b (mitogen-activated protein kinase 11) | NM_002751.5 | ATGTCGGGCCCTCG (SEQ ID NO: 43) | TCACTGCTCAATCTCC AGGC (SEQ ID NO: 44) |
| STAT3 (signal transducer and activator of transcription 3) | NM_139276.2 | ATGGCCCAATGGAA TCAG (SEQ ID NO: 45) | TCACATGGGGGAGGT AGC (SEQ ID NO: 46) |

Transfection of Expression Constructs (FTR and PDM Mixtures)

According to a predesigned matrix, each reporter gene (FTR) that is used in the analysis is mixed with either a control wild type PDM gene or a test PDM gene, prepared as described above, and mixed with appropriate transfection reagents.

In one option, the transfection mixes are placed and optionally dehydrated on an appropriate solid support substrate. In various settings, the substrate includes various solid substrates, such as: microscope slides, chip, cell culture plates, multi-plate wells, 96-well plates, 384-well plates and the like. Each mixture is placed in a designated, traceable locus/spot (i.e. a designated well or a designated location on the slide or chip). To the transfection mixtures on the substrate, a fixed number of cells (in the range of about 100 to 100,000, depending on the substrate type and as described above) is dispensed onto each spot, in normal full growth media. The cells are selected from HeLa cells, HEK 293 cells, NCI60 cell lines such as A549, EKVX, T47D, HT29 or any other suitable cell line, based on the tested PDM and assay. The test cells are placed on the solid substrate and incubated for 12-48 hours, in accordance with the type of cell, growth media and transfection conditions. The incubation time allows the cells to adhere to the substrate, and to introduce and express the FTR and PDM.

In another option, cells are plated on the solid substrate according to a predesigned matrix (in a designated, traceable locus/spot (i.e. a designated well or a designated location on the slide or chip)). After a predetermined period of time, the cells are transfected with the FTR and the appropriate PDM (WT PDM or test PDM), under appropriate transfection conditions. The FTR and the appropriate PDM may be located on two separate molecules, or on a single molecule encoding for both genes.

Assay Implementation: Inducible Promoter

Following adequate expression of the reporter FTR, growth media is replaced with low serum media (to remove any growth factors/ligands present in the media), to reduce to minimum background stimulated signaling.

When signaling level is significantly reduced (within 4 to 16 hours), induction of PDM expression is initiated. This is achieved by addition of tetracyclin when using a tetracyclin inducible promoter and ecdysone when using an ecdysone inducible promoter.

In some examples, interstitial fluid (IF) and/or anti-cancer drugs are added to induce expression of the PDM, to thereby test the effect of the IF or drug on the PDM.

Assay Implementation—Constitutive Promoter

Following adequate expression of FTR and PDM in the cells (both under the control of a constitutive promoter), growth media is replaced with low serum media (to remove of any growth factors/ligands present in the media) to reduce to minimum background stimulated signaling.

In some examples, interstitial fluid and/or anti-cancer drugs are added to induce expression of the PDM, and thereby test the effect of the IF or drug on the PDM.

Image Acquisition and Analysis

Following PDM expression (30 hours after transfection), cells are fixed by washing 3 times with phosphate buffered saline (PBS), incubation for 5 minutes in 4% paraformaldehyde (PFA), and 3 subsequent washes with PBS. The slide is then covered by a cover slip and the localization of each corresponding FTR is imaged.

Image analysis of each FTR, both in control wild-type cells as well as in the PDM transfected cell, is performed and comparison is made. The difference between the localization of the FTR in control cells vs. PDM transfected cells, is quantified, and used to determine whether an oncogenic or a wild type form of the tested PDM was present in the tested sample. The quantification is done using standard image analysis software, such as ImageJ.

An exemplary assay using HeLa cells as the assay cells:
Day 0: slides are precoated with poly-1-lysine 0.01%, for 5 minutes at room temperature (RT) and then washed with sterile water (DDW). The water is aspirated and the slides are dried for 2 hrs. HeLa cells are plated (15000 cells) in 200 μl complete medium for each well (complete medium: DMEM, 10% FBS, 1% pen/strep (P/S)).

Day 1: Transfection reagent (FugeneHD reagent (Promege, Cat. NO. E2311) is warmed to RT and Vortexed. For each well, a transfection mix is prepared in tubes, which includes: 50/100/200 ng expression construct of the PDM in tubes; 50/100 ng of expression construct of the appropriate FTR; Optimem buffer (to a total of 10 μl) and FugeneHD (1 μl for each 3 μg of DNA). The transfection mixture is incubated at RT for 15 minutes. The cell medium is aspirated from the wells, and each well is supplemented with 100 μl transfection medium (DMEM, 10% FCS, no antibiotics). 10 μl of the transfection mixture is added to each well. The cells are then incubated at 37° C. in humidified incubator (5% $CO_2$). Six-eight hours later, the medium is replaced to starvation medium 1 (DMEM with 0.1% FCS, 1% Pen/Strep) and the cells are incubated at 37° C. humidified incubator, 5% $CO_2$. For assays which require a 24 hour incubation of a drug/chemical inhibitor, it is added at the needed concentration. For assays which require incubation with drug: Replace medium with starvation medium 2 supplemented with the drug as needed. The cells are then incubated at 37° C. in humidified incubator (5% CO2). Additionally, if a shorter incubation time of a drug is needed, it may be conducted.

Day 2: 26 hours later (i.e., 4 hours prior to fixation of the cells), the medium is changed to starvation medium 2 (DMEM with 1% P/S). The cells are then incubated at 37° C. in humidified incubator (5% $CO_2$).

For assays which require inducement of signaling: Replace medium with starvation medium 2 supplemented with the inducer as needed. The cells are then incubated at 7° C. in humidified incubator (5% $CO_2$). Additionally, if a shorter incubation time of a drug/chemical inhibitor is needed, it may be conducted.

30 hours after transfection, the cells are fixed (all steps at room temp) by the following process: the cells are washed 3 times with PBS. Fixed with fixation solution (5% Glucose/4% paraformaldehyde (PFA) in PBS) for 10 minutes, Washed 3 times with PBS. The cells are optionally stained with DAPI solution, after which they are washed three times with PBS.

Figure 2A:
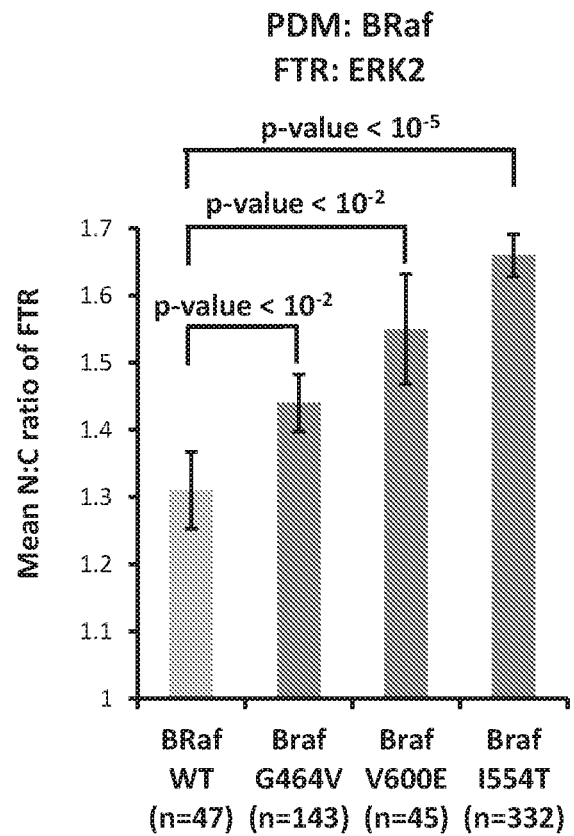
FIG. 2A—A bar graph showing results of a cell based assay in which the genes encoding BRAF in wild type (BRAF WT) or mutant forms (BRAF mutants G464V or V600E or I554T) have been expressed in test cells, along with a reporter protein (FTR), and the amount of the FTR (ERK2-GFP) in the cytoplasm and in the nucleus was quantified, based on fluorescence microscope images of the cells (fixed 30 hours after transfection). The ratio between the intensity of the FTR (ERK2) in the nucleus (N) and cytoplasm (C) was measured (N:C ratio). The number of cells measured (n) is indicated for each condition.
Figure 2B:
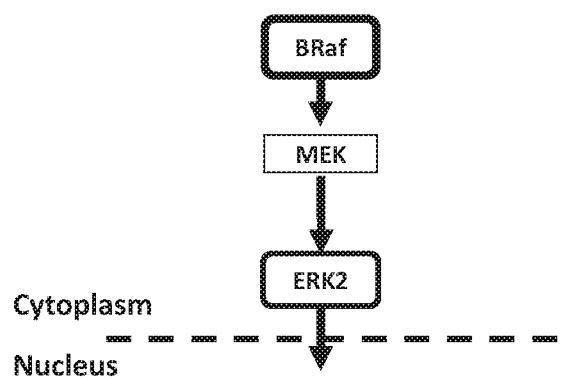

Example 1: Subcellular Translocation Assay of the ERK1/2 Pathway can Discriminate Between the WT and Mutant BRAF and Identify BRAF Driver Mutations in a Quantitative Manner HeLa assay cells were transfected with a WT PDM (BRAF-WT) or the indicated mutated PDMs (mutated BRAF, harboring one of the following mutations: known driver mutations G464V orvV600E, a functionally unknown mutation, I554T, which resides in the kinase domain of BRAF), along with a corresponding FTR (ERK-2). 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). Altogether, the results show that the two functionally known mutations (G464V and V600E) activate the ERK1/2 signaling pathway (FIG. 2A). The results further show that the functionally unknown mutation (I544T) also actives the tested signaling pathway, indicating that this is an oncogenic mutation. Moreover, when using ERK2 as the FTR, the activation levels by the mutated BRAF harboring the functionally unknown I544T mutation, are as high as those observed for the BRAF harboring the known V600E mutation, which has been previously reported to be more active than the G464V mutation.

Thus, by using the methods disclosed herein, a BRAF mutant (I544T), is identified as a functionally active mutant, capable of inducing aberrant signal transduction pathway, wherein the graded increase in subcellular translocation of the FTR is correlated to the gravity of the BRAF oncogenic mutation.

Figure 3A:
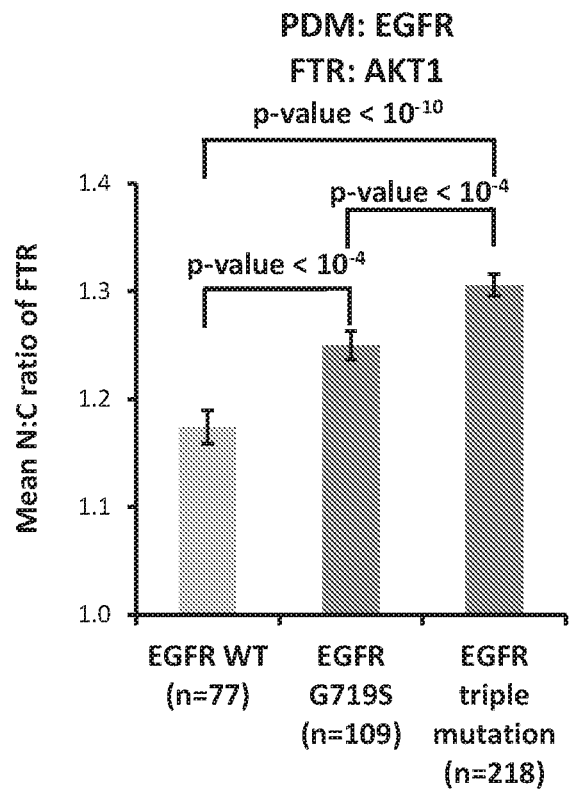
FIG. 3A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (AKT1-GFP) in the cytoplasm and in the nucleus was quantified based on fluorescence microscope images of the cells (fixed 30 hours after transfection). The ratio between the intensity of the FTR (AKT1) in the nucleus (N) and cytoplasm (C) was measured (N:C ratio). The number of cells measured (n) is indicated for each condition.
Figure 3B:
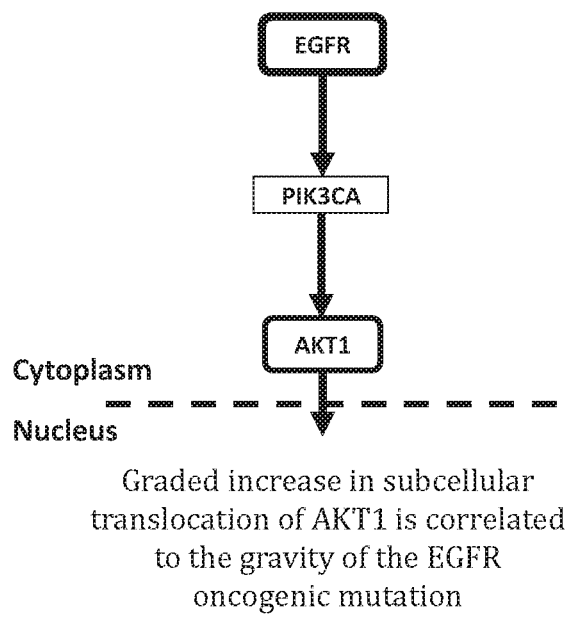
Figure 4A:
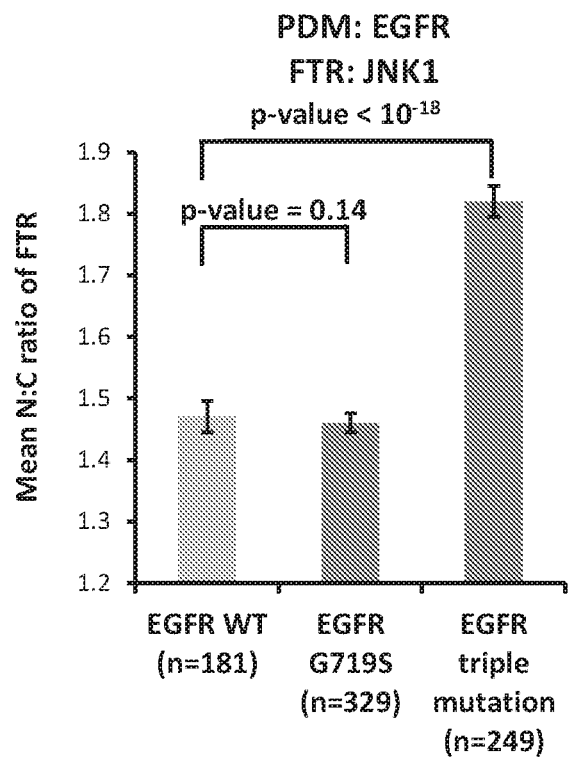
FIG. 4A—A bar graph showing the results of a cell based assay in which the genes encoding for EGFR in wild type form (EGFR WT), single mutant form (EGFR G719S) or triple mutant form (EGFR triple mutant, G719A, T790M and L861Q) have been expressed in test cells, along with a reporter protein (FTR), and the amount of the FTR (JNK1A1-GFP) in the cytoplasm and in the nucleus was quantified based on fluorescence microscope images of the cells (fixed 30 hours after transfection). The ratio between the intensity of the FTR (JNK1A1) in the nucleus (N) and cytoplasm (C) was measured (N:C ratio). The number of cells measured (n) is indicated for each condition.
Figure 4B:
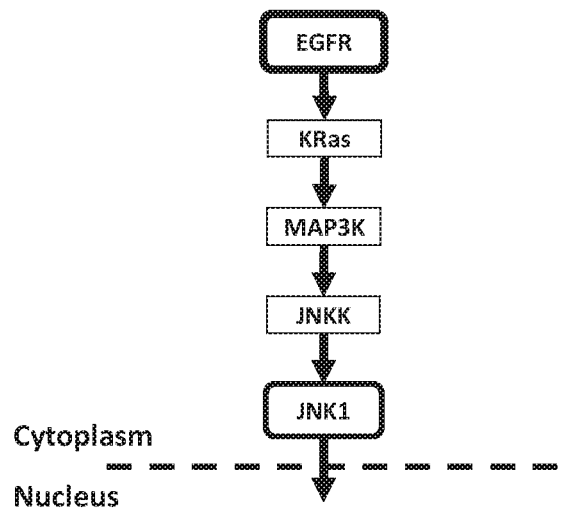
Figure 5A:
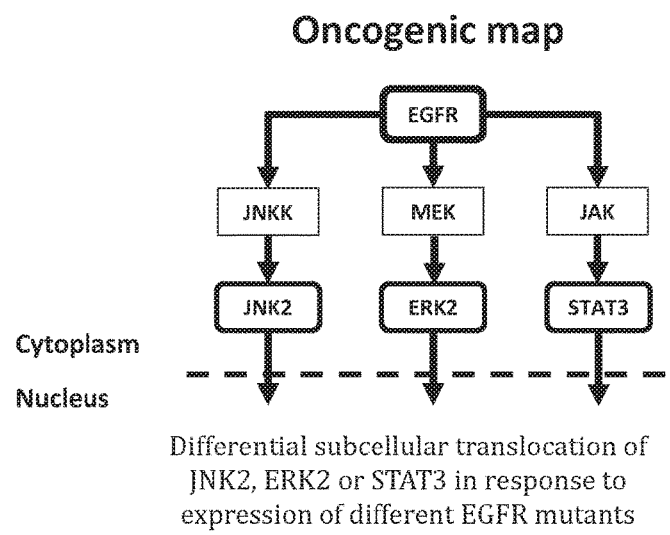
FIG. 5A—A schematic representation of the signaling pathway affected by PDM (EGFR) and the corresponding FTRs (JNK2, ERK2, STAT3).
Figure 5B:
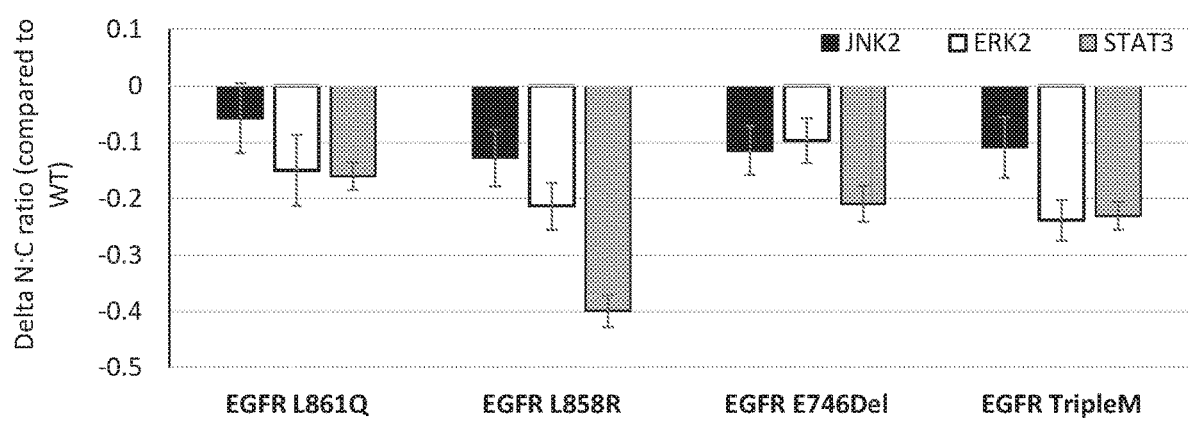

Example 2: Subcellular Translocation Assay can Discriminate Between the WT and Mutant EGFR and Grading EGFR Mutation Severity HeLa assay cells were transfected with a WT PDM (EGFR-WT) or the indicated mutated PDMs (mutated EGFR, harboring one of the following mutations: known driver mutation G719S, L861Q, L858R, E746Del or a mutant which includes three known driver mutations- G719A, T790M (known to confer resistance to small molecule EGFR inhibitors) and L861Q, (triple mutation)), along with a corresponding FTR. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 3A, 4A and 5B. In FIG. 3A, the FTR is AKT1 and in FIG. 4A, the FTR is JNK1. FIG. 5B is an enhanced comparison of 4 mutations along 3 different pathway, presented as the difference in N:C ratio (Delta N:C ratio) compared to the WT. Altogether, the results show that when using AKT1 as the FTR (FIG. 3A), JNK1 as the FTR (FIG. 4A) or JNK2, ERK2 and STAT3 (FIG. 5B), the activation levels vary in the different mutants. Thus, by using the methods disclosed herein, that graded increase in subcellular translocation of the FTR is correlated to the gravity of the EGFR oncogenic mutation.

Figure 6A:
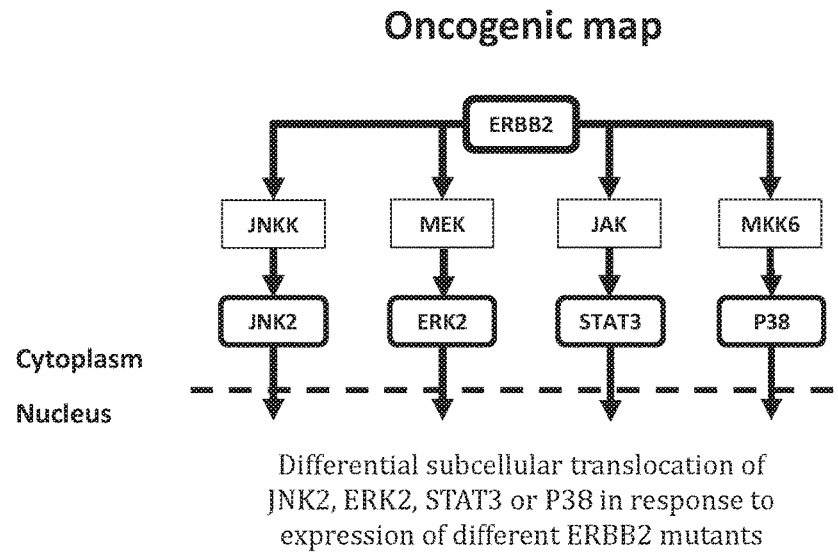
FIG. 6A—A schematic representation of the signaling pathway affected by PDM (ERBB2) and the corresponding FTRs (JNK2, ERK2, STAT3, P38).
Figure 6B:
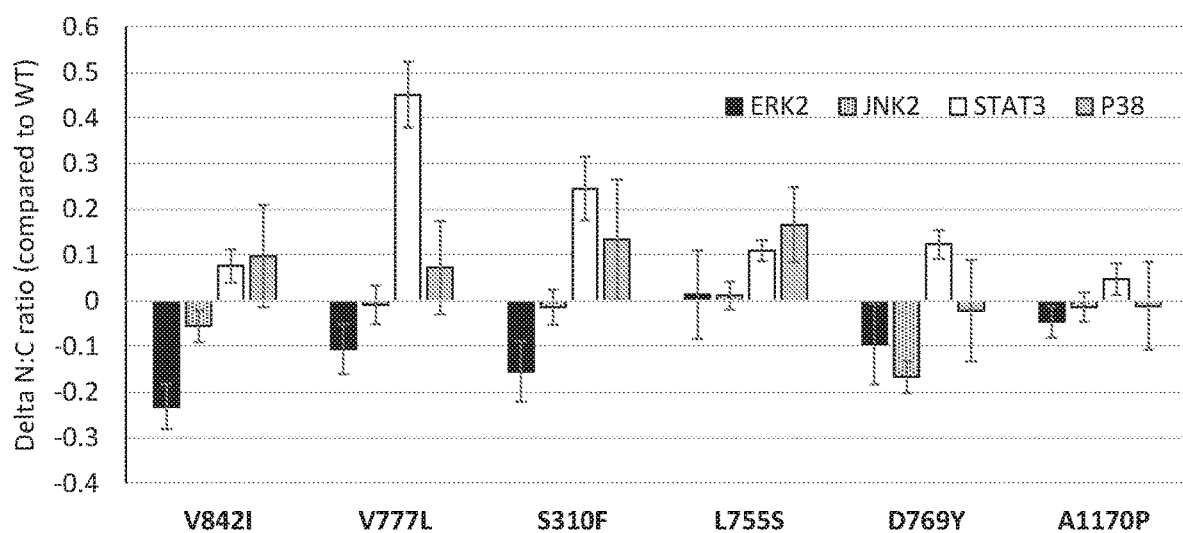

Example 3: Subcellular Translocation Assay can Allow Grading ERBB2 Mutation Severity HeLa assay cells were transfected with a WT PDM or the indicated mutated PDMs (ERBB2 V8421, V777L, S310F, L755S, D769Y, A1170P), along with a corresponding FTR, JNK2, ERK2, STAT3 or P38. 24 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio) and is presented as the difference in N:C ratio (Delta N:C ratio) compared to the WT. The results presented in FIG. 6B are an enhanced comparison of 6 mutations along 4 different pathways.

Altogether, the results show that the activation levels vary in the different mutants. Thus, by using the methods disclosed herein, that graded increase in subcellular translocation of the FTR is correlated to the gravity of the ERBB2 oncogenic mutation.

Figure 7A:
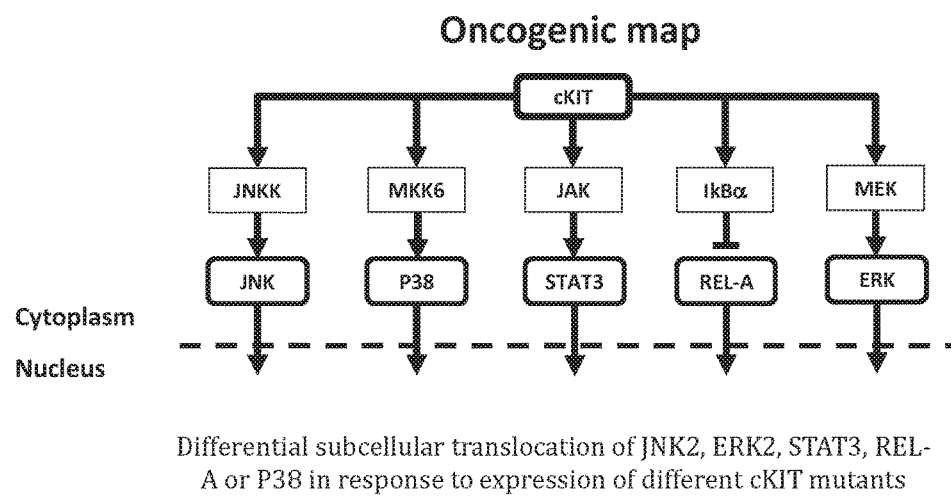
FIG. 7A—A schematic representation of the signaling pathway affected by PDM (cKIT) and the corresponding FTRs (JNK2, ERK2, STAT3, P38, REL-A).
Figure 7B:
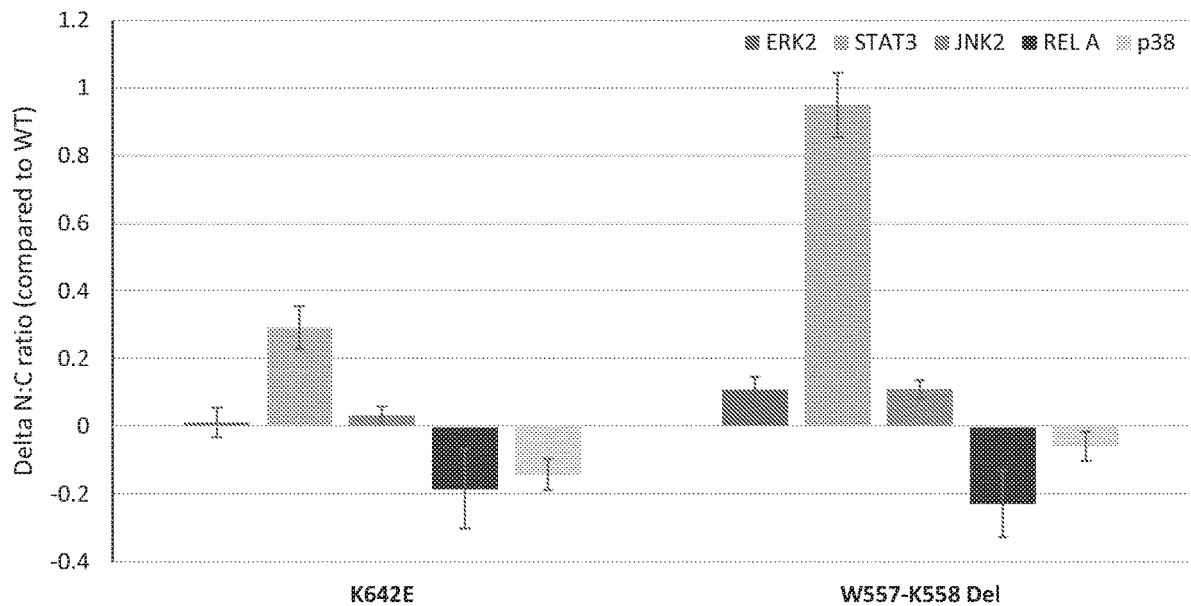

Example 4: Subcellular Translocation Assay can Allow Grading cKIT Mutation Severity HeLa assay cells were transfected with a WT PDM or the indicated mutated PDMs (cKIT K642E, W557-K558del), along with a corresponding FTR, ERK2, STAT3, JNK2, REL-A or P38. 24 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio) and presented as the difference in N:C ratio (Delta N:C ratio) compared to the WT. The results presented in FIG. 7B are an enhanced comparison of 2 mutations along 5 different pathways.

Altogether, the results show that the activation levels vary in the different mutants. Thus, by using the methods disclosed herein, that graded increase in subcellular translocation of the FTR is correlated to the gravity of the cKIT oncogenic mutation.

Figure 8A:
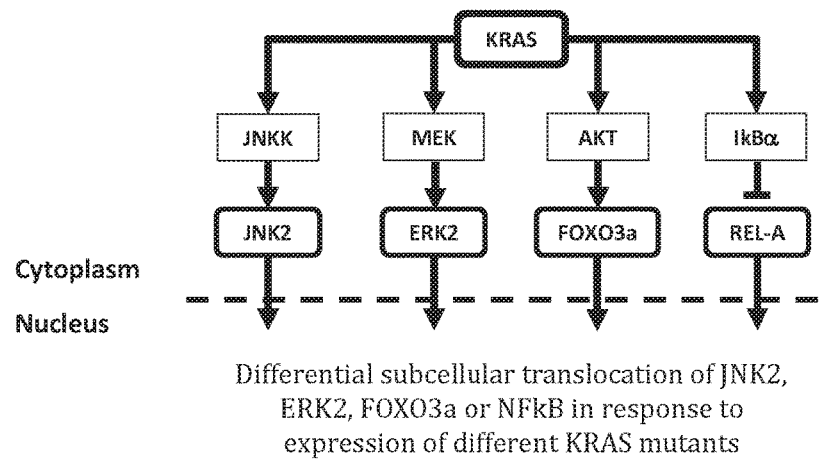
FIG. 8A—A schematic representation of the signaling pathway affected by PDM (KRAS) and the corresponding FTRs (JNK2, ERK2, FOXO3a, REL-A).
Figure 8B:
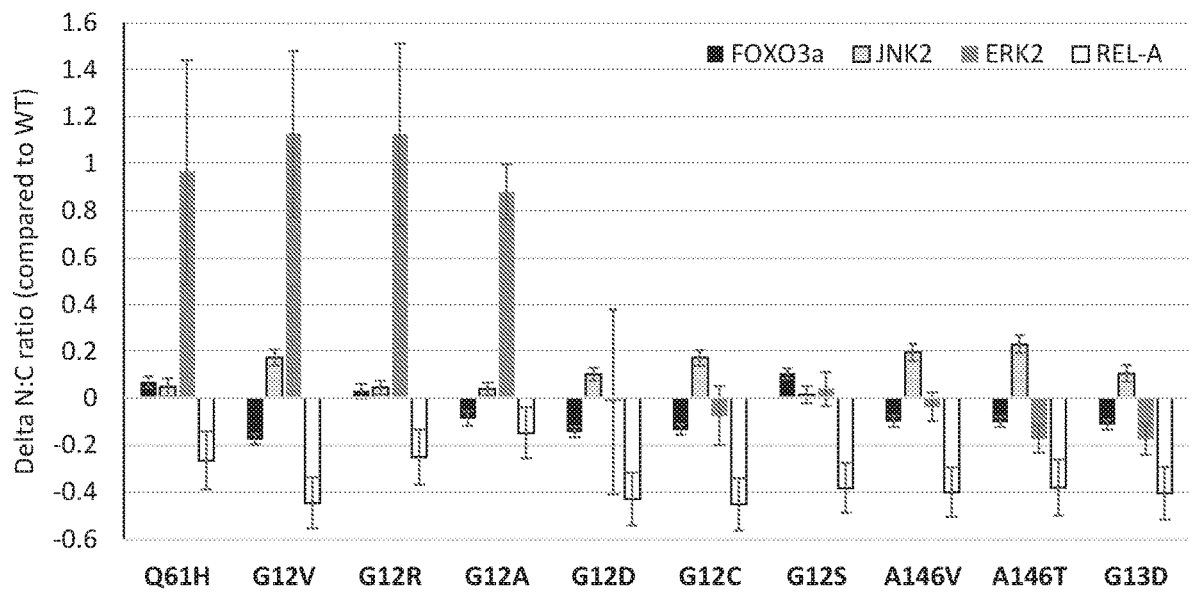

Example 5: Subcellular Translocation Assay can Allow Grading KRAS Mutation Severity HeLa assay cells were transfected with a WT PDM or the indicated mutated PDMs (KRAS Q61H, G12V, G12R, G12A, G12D, G12C, G12S, A146V, A146T, G13D), along with a corresponding FTR, FOXO3a, JNK2, ERK2 or REL-A. 24 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio) and presented as the difference in N:C ratio (Delta N:C ratio) compared to the WT. The results presented in FIG. 8B are an enhanced comparison of 10 mutations along 4 different pathways. Altogether, the results show that the activation levels vary in the different mutants. Thus, by using the methods disclosed herein, that graded increase in subcellular translocation of the FTR is correlated to the gravity of the KRAS oncogenic mutation.

Figure 9A:
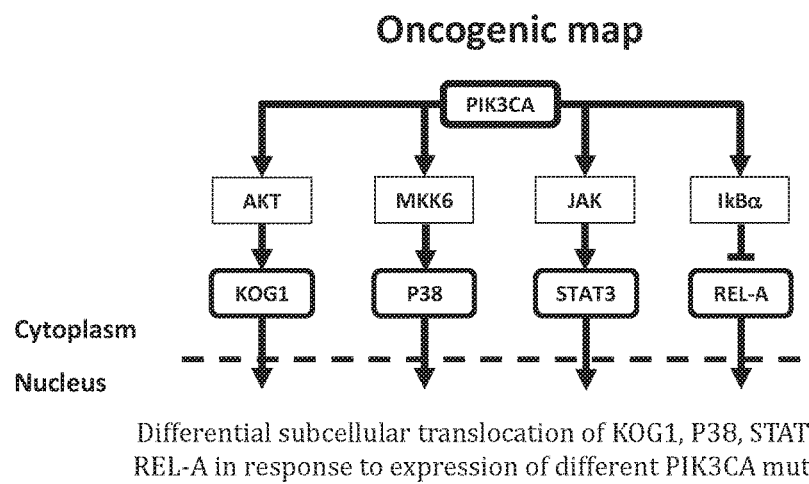
FIG. 9A—A schematic representation of the signaling pathway affected by PDM (PIK3CA) and the corresponding FTRs (KOG1, P38 STAT3, REL-A).
Figure 9B:
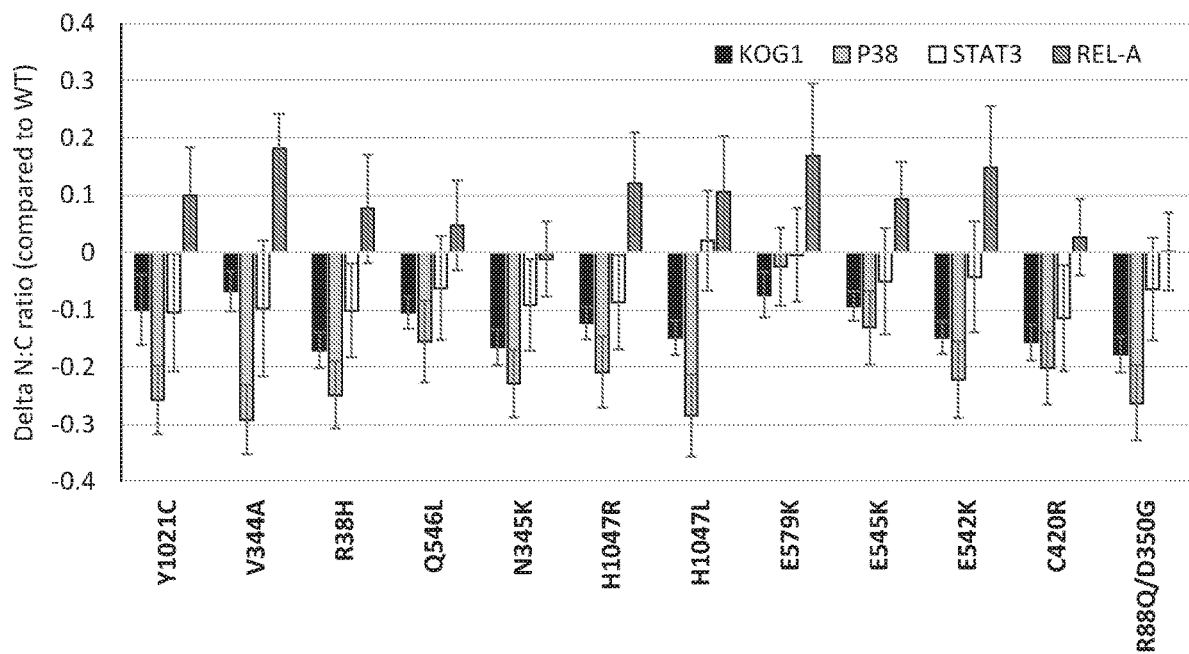

Example 6: Subcellular Translocation Assay can Allow Grading PIK3CA Mutation Severity HeLa assay cells were transfected with a WT PDM or the indicated mutated PDMs (PIK3CA Y1021C, V344A, R38H, Q546L, N345K, H1047R, H1047L, E579K, E545K, E542K, C420R, R88Q/D350G), along with a corresponding FTR, KOG1, P38, STAT3 or REL-A. 24 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio) and is presented as the difference in N:C ratio (Delta N:C ratio) compared to the WT. The results presented in FIG. 9B are an enhanced comparison of 12 mutations along 4 different pathways. Altogether, the results show that the activation levels vary in the different mutants. Thus, by using the methods disclosed herein, that graded increase in subcellular translocation of the FTR is correlated to the gravity of the PIK3CA oncogenic mutation.

Figure 10A:
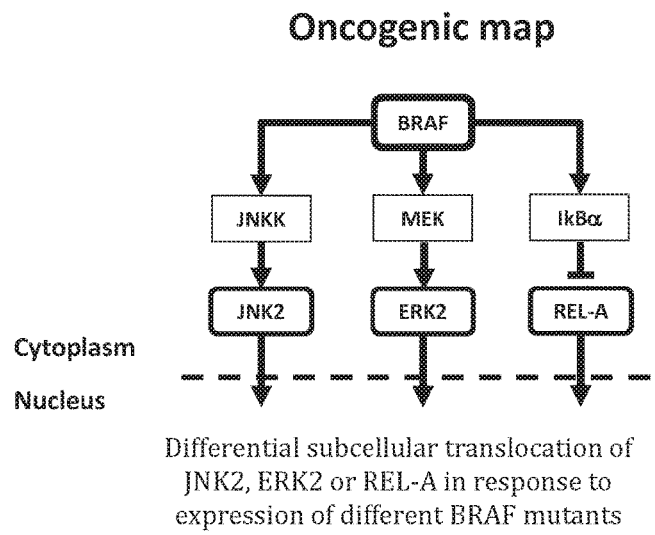
FIG. 10A—A schematic representation of the signaling pathway affected by PDM (BRAF) and the corresponding FTRs (ERK2, JNK2, REL-A).
Figure 10B:
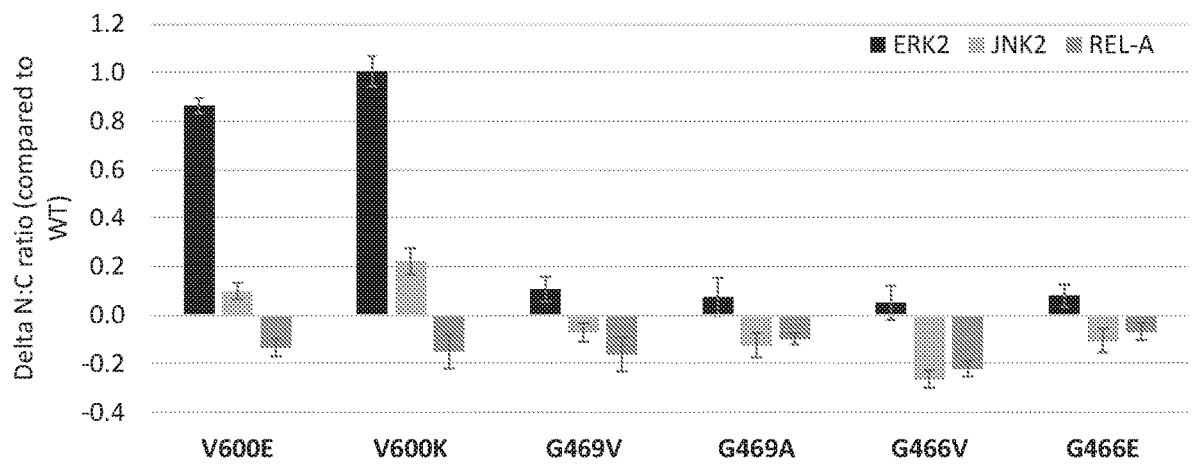

Example 7: Subcellular Translocation Assay can Allow Grading BRAF Mutation Severity HeLa assay cells were transfected with a WT PDM or the indicated mutated PDMs (BRAF V600E, V600K, G468V, G469A, G466V, G466E), along with a corresponding FTR, ERK2, JNK2 or REL-A. 24 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio) presented as the difference in N:C ratio (Delta N:C ratio) compared to the WT. The results presented in FIG. 10B are an enhanced comparison of 6 mutations along 3 different pathways. Altogether, the results show that the activation levels vary in the different mutants. Thus, by using the methods disclosed herein, that graded increase in subcellular translocation of the FTR is correlated to the gravity of the BRAF oncogenic mutation.

Figure 11A:
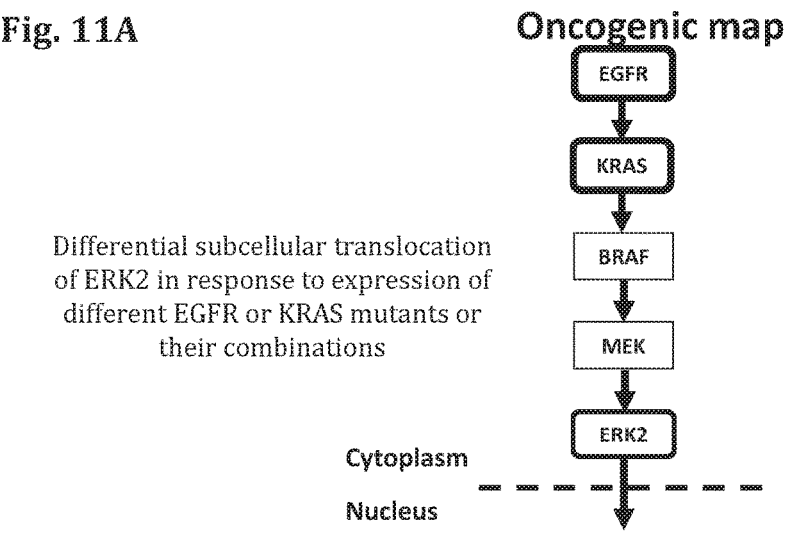
FIG. 11A—A schematic representation of the signaling pathway affected by PDMs (EGFR and KRAS) and the corresponding FTR (ERK2).
Figure 11B:
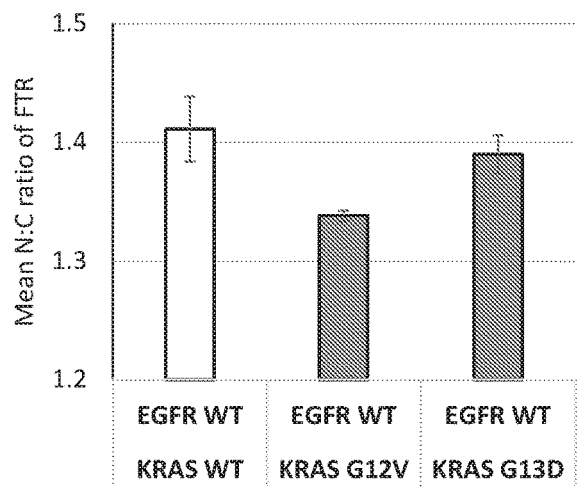
Figure 11C:
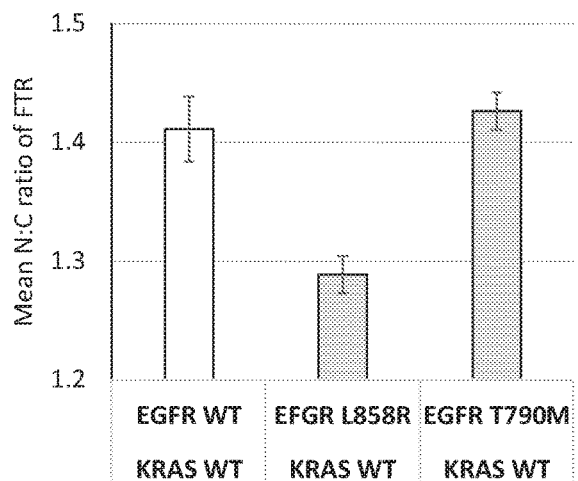
Figure 11D:
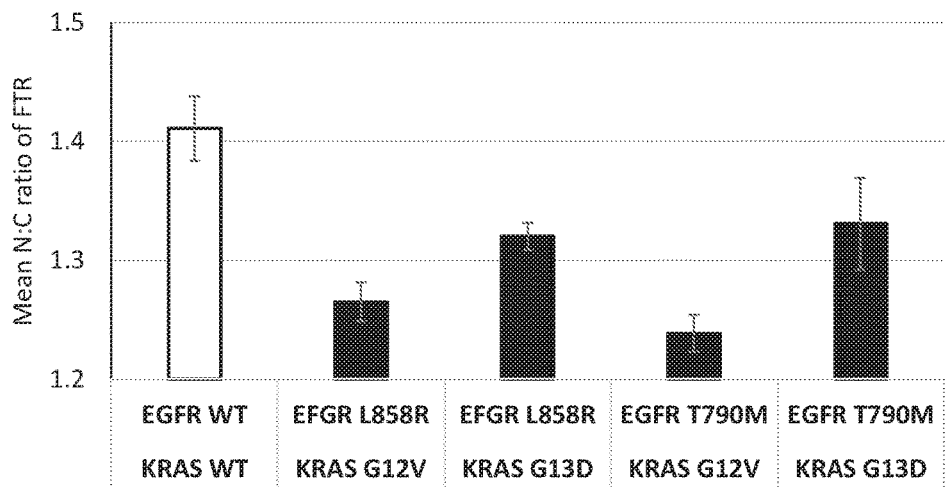
Figure 12A:
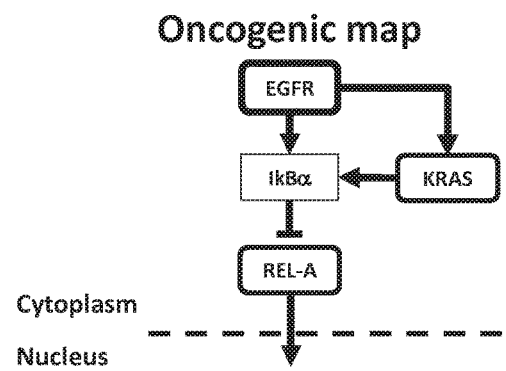
FIG. 12A—A schematic representation of the signaling pathway affected by PDMs (EGFR and KRAS) and the corresponding FTR (REL-A).
Figure 12B:
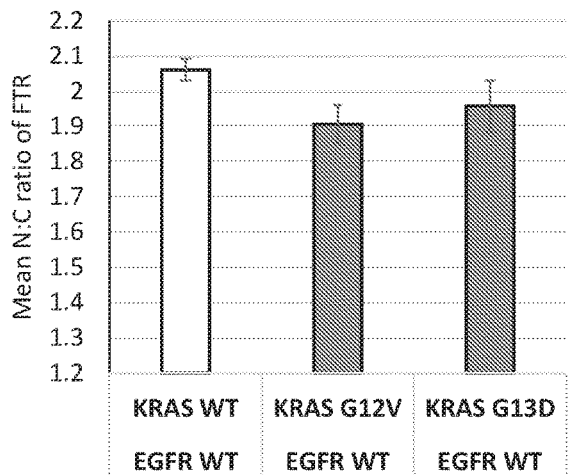
Figure 12C:
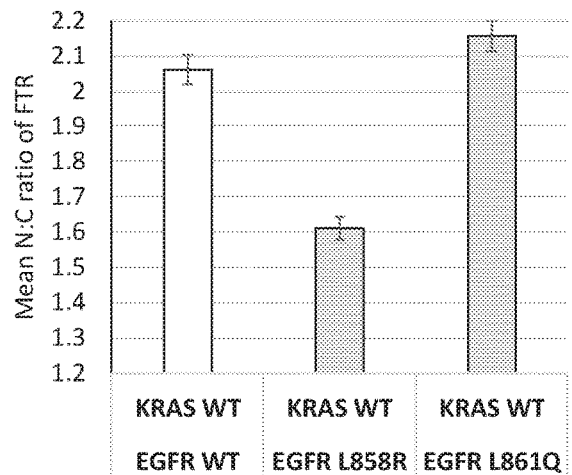
Figure 12D:
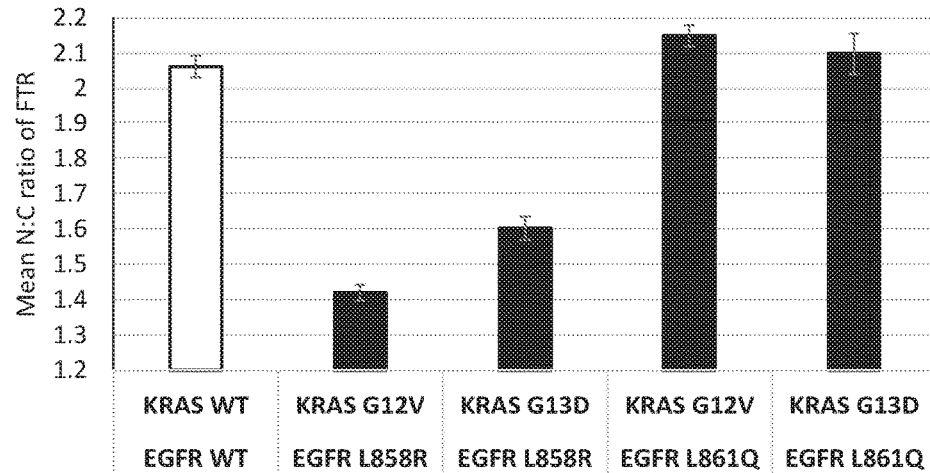
Figure 13A:
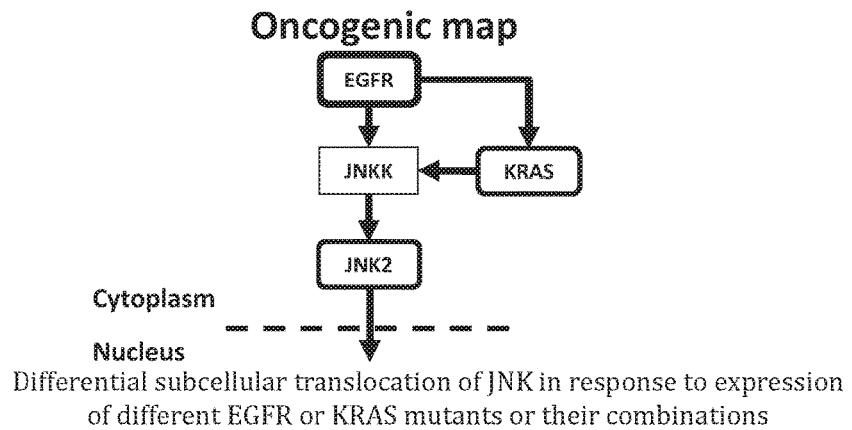
FIG. 13A—A schematic representation of the signaling pathway affected by PDMs (EGFR and KRAS) and the corresponding FTR (ERK2).
Figure 13B:
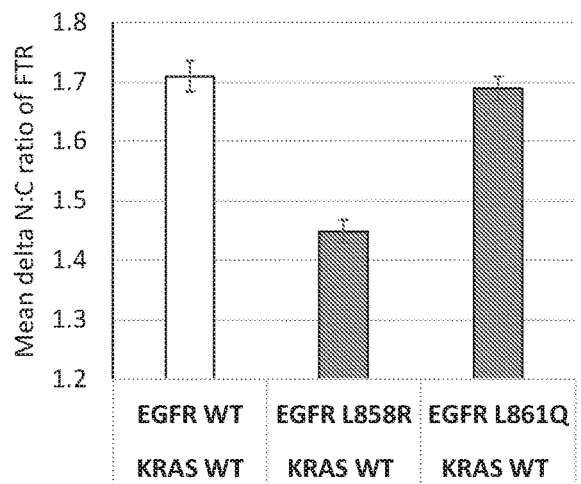
Figure 13C:
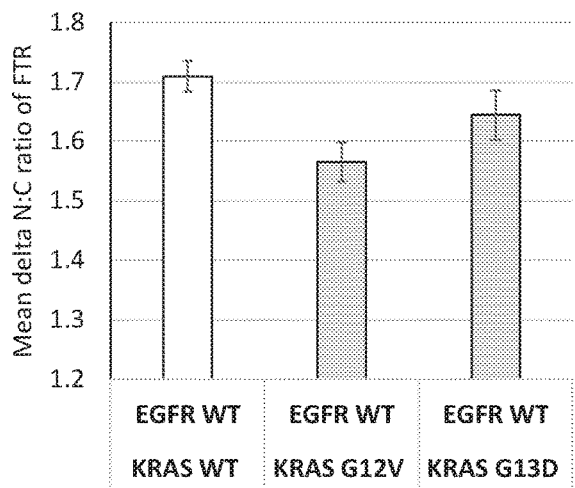
Figure 13D:
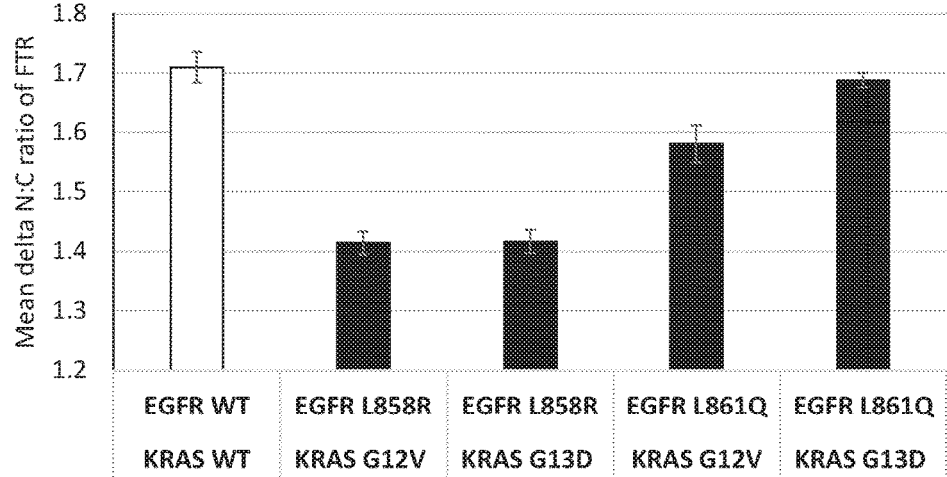

Example 8: Subcellular Translocation Assay can Allow Determining of the Dominant Mutation Between EGFR and KRAS Among Different Pathways HeLa assay cells were transfected with a WT EGFR PDM or KRAS PDM or the indicated mutated PDMs (EGFR L858R, T790M, L861Q, KRAS G12V, G13D), along with a corresponding FTR: ERK2, JNK2 or REL-A. 24 hours post transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results presented in FIG. 11B, FIG. 11C and FIG. 11D show that while each mutation separately effects the ERK1/2 pathway, combining both EGFR and KRAS mutations reveals that the EGFR L858R mutation is dominant in respect to the KRAS mutations (with G12V having a slightly added effect), while the KRAS mutations are dominant over the EGFR T790M mutation. When measuring a second pathway, NFkB, (FIG. 12B, FIG. 12C and FIG. 12D), the EGFR L858R mutations is dominant, and the L861Q, implying that for this pathway KRAS mutations are secondary to EGFR mutations. Lastly, when measuring the JNK pathway, the results presented in FIG. 13B, FIG. 13C and FIG. 13D, show that the EGFR L858R mutation is dominant over the KRAS mutations but the KRAS mutants are dominant over the EGFR L861Q mutation. Overall, the pathway directly linked to KRAS show differential dominance in comparison to the EGFR mutants, while EGFR specific pathways are not affected by the precise of the KRAS mutations. The results demonstrate that using the methods disclosed herein, testing combinations of genes can provide additional insights as to their activity as well as their dominance, importance or interaction with other mutations.

Figure 14A:
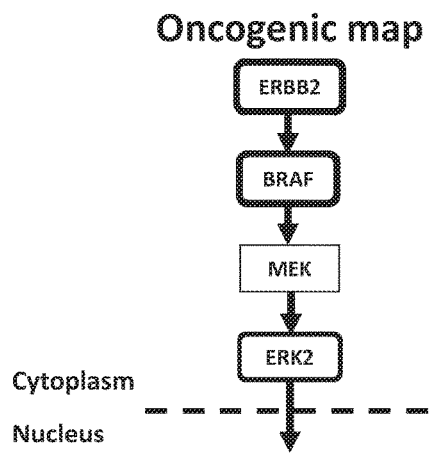
FIG. 14A—A schematic representation of the signaling pathway affected by PDMs (EGFR and BRAF) and the corresponding FTR (ERK2).
Figure 14C:
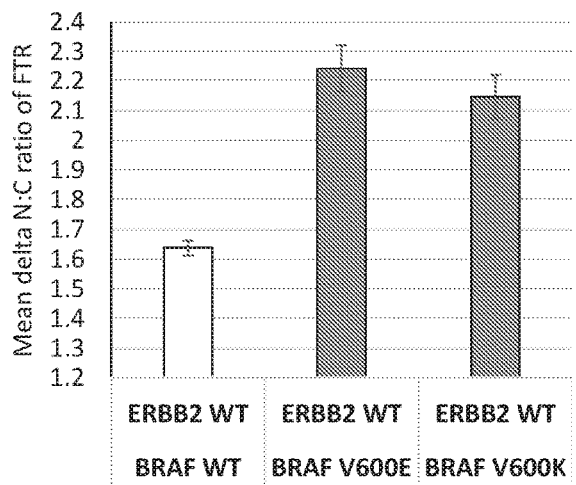
Figure 14B:
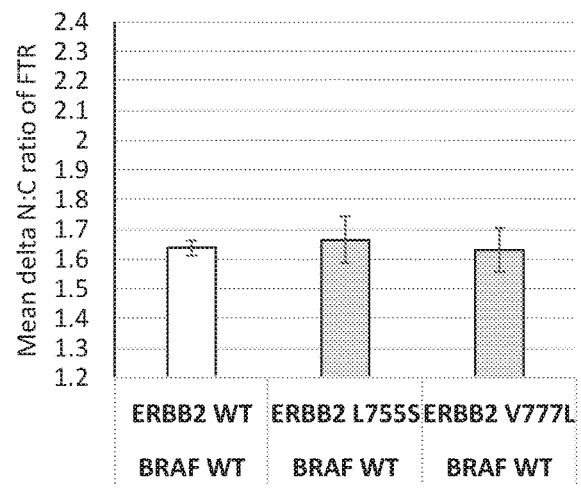
Figure 14D:
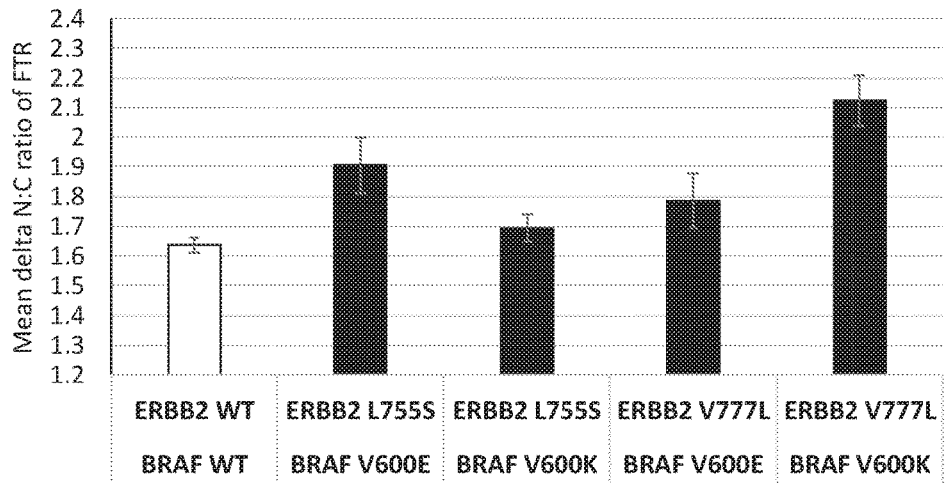

Example 9: Subcellular Translocation Assay can Allow Determining of the Dominant Mutation Between ERBB2 and BRAF Among Different Pathways HeLa assay cells were transfected with a WT ERBB2 PDM or BRAF PDM or the indicated mutated PDMs (ERBB2 L755S, V777L, BRAF V600E, V600K), along with a corresponding FTR: ERK2. 24 hours post transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results presented in FIG. 14B and FIG. 4C show that while BRAF mutants affects the ERK1/2 pathway, the ERBB2 mutant are not significantly active. When combining both ERBB2 and BRAF mutations, the results shown in FIG. 14D reveal that the presence of ERBB2 decreases to some extent the effect of the BRAF mutants with the exception of the ERBB2 V777L/BRAF V600K combination. Therefore, the ERK1/2 pathway is affected to a different degree by ERBB2 and BRAF combined mutations. The results demonstrate that using the methods disclosed herein, testing combinations of genes can provide additional insights as to their activity, and the interaction therebetween.

Example 10: Exemplary Calculation of Oncogenic Indexes (Progression Free Survival Index, Overall Survival Index, Probability of Response to a Drug)

The methods used for generating the following exemplary oncogenic indexes utilize, among others, machine learning techniques. A first step in the calculations is a normalization step (preprocessing). The normalization step may be followed by a suitable machine learning method to learn the function that maps the actual results obtained from the various biological assay outputs (i.e. Testing of patients genes by the methods and systems disclosed herein and determining the activation levels thereof) to a clinically relevant index.

In the following examples, the output of the various calculations is an oncogenic index. The type of index depends on the input (data) provided for generating the index. For example, when using the biological assay outputs for the patient specific genes, together with an observed progression free survival, the resulting index is the progression free survival index (i.e., the generated index indicates/predicts the progression free survival of the patient, based on the patient specific mutations). Similarly, if the input (data) is the biological assay outputs for the patient specific genes, in the presence and absence of a drug, together with measured response to a drug in the clinic, the resulting index is a indicator/predictor of the drug response.

Normalization:

As detailed herein above, the methods and systems utilized allow for the determination of the patient's specific mutations and mutated signaling pathways activation levels. The activation levels may be expressed in units of Nucleus to Cytoplasm Ratio (NCR), which is measured and determined by the methods disclosed herein.

In this example, the raw NCR of the wild-type (WT) reference is arbitrarily set to a reference value (for example, zero), and each of the measured NCR of the tested PDM ("test NCR") is given a value which is relative to this WT reference. For example, if, for a particular patient tumor specimen the NCR of the reference WT gene X found to be 1.4, and NCR of test gene X is found to be 2.1, the reported value for gene X is 0.7 (i.e., 2.1-1.4). Similarly, each measured test NCR can be relative to a relevant fixed reference and normalized to its units (i.e. so that the reference is always 100). For example, for an exemplary PDM-FTR pair, KRAS-ERK: if the value for KRAS-WT-ERK is 1.4 and the patient-KRAS-ERK value is 1.7, the KRAS_WT-ERK may be normalized to 100 and the patient-KRAS-ERK pair would be accordingly given the value 121 (121=1.7/1.4*100).

Thus, the normalized output of the biological assay may be used as the input for various suitable machine learning techniques. Exemplary techniques are described below:

Correlation Uni/Multi variate Analysis: The normalized data can be used to analyze correlation between the activation level of particular signaling pathway and, for example, patient response. Standard statistical methods are applied to identify those pathways, for which the correlation between activation and a beneficial patient response, in a univariate analysis, is statistically significant. These pathways are markers of outcome, given the existing clinical status. Multivariate analysis can be applied to identify sets of genes and/or pathways, the activation levels of which, when used in combination, are better markers of outcome (patient response) than the individual genes/pathways that constitute the sets. Further, it is possible to define groups of genes/pathways known or suspected to be associated with particular aspects of the molecular pathology of cancer. A gene/pathway can be assigned to a particular group based either on its known or suspected role in a particular aspect of the molecular biology of cancer or based on its co-activation with another gene/pathway already assigned to a particular group.

Support Vector Machine (SVM): After a normalization step, the data is provided to a SVM that can categorize activation patterns into groups and subgroups of clinical relevance. An SVM uses a kernel to map activation levels to higher dimensional spaces and can identify a hyperplane that separates the activation level of different groups. Examples of kernels (K in the equation below) can include such kernels as, but not limited to: Linear, Polynomial, Gaussian radial basis function, Hyperbolic tangent, or any other non-linear function.

Given some training data D, a set of n the form:

$$\mathcal{D} = \{(x_i, y_i) | x_i \in \mathbb{R}^p, y_i \in \{-1, 1\}\}_{i=1}^n,$$

Where y is the response variable of a clinical outcome (such as responder vs. non responder) to which the point x belongs. X is a vector of the normalized outputs of the biological assay (as described herein) and is the high dimensional description of all the activity levels observed for a specific patient. The SVM reduces to the following optimization problem:

$$\tilde{L}(\alpha) = \sum_{i=1}^n \alpha_i - \frac{1}{2} \sum_{i,j} \alpha_i \alpha_j y_i y_j x_i^T x_j = \sum_{i=1}^n \alpha_i - \frac{1}{2} \sum_{i,j} \alpha_i \alpha_j y_i y_j k(x_i, x_j)$$

Where the quantity is maximized with respect to a subject to several constraints specifically that: $\alpha_i \geq 0$, and that $$\sum_{i=1}^n \alpha_i y_i = 0.$$

The end result of the optimization problem is a hyper plans defined by the $\alpha$'s:

$$W = \sum_i \alpha_i y_i x_i.$$

This hyper-plane divides the space of patient activation to the two response categories (such as the responding patients and non-responding patients). Though the natural application of the SVM is a binary categorization, Multiclass SVM may be used to add higher resolution of categories and more response features. For example, the normalized data can be used to categorize based on the activation level of sets of genes/pathway to groups of patient prognosis (i.e. progression free survival: category A 1-3 month, category B 4-6 month, category C 7-9 month, etc.). The SVM's are trained on the normalized activation data in conjunction with the observed category of each patient in the training set, D. The SVM's can be retained and tuned to accommodate further data.

Generalized Linear Models (GLM)—After a normalization step (as above), the data is fed to a GLM that can predict clinical relevance. A GLM uses kernels to unify various other statistical models, including linear regression, logistic regression and Poisson regression and map activation levels to result of variables of clinical relevance.

The expected value of the dependent variable (i.e. the index) is expressed as a link function g( ) over the linear predictor X β as in the following equation:

$$E(Y)=\mu=g^{-1}(X\beta)$$

Where X is the vector of all the covariates and β is vector of unknown parameters that need to be learned from examples in order to assign 'significance' to each of the covariate variables. The link function can take many forms, such as, for example, but not limited to: Normal, Exponential, Gamma, Inverse Gaussian, Poisson, and the like. The choice of the link function is determined from the observed data as well as considerations of the resulting index.

In some examples, the vector β of unknown weights can be found using Maximum Likelihood optimization by many techniques, such as, for example, using the Newton-Raphson method.

Once the vector β is found, new normalized outputs of the biological assay can be added into the equation and the resulting figure is the clinical index.

As an example, a vector of activation levels is determined by the biological assay: KRAS-ERK, KRAS-FOXO3, KRAS-RelA, PI3K-FOXO3, PI3K-RelA, EGFR-STAT3, EGFR-ERK, EGFR-FOXO3, EGFR-RelA. The normalized outcome of this vector of observations might be [110, 160, 100, 80, 80, 160, 100, 100, 100] and the vector of unknown weights might be learned as (β=[0.0017, 0.0033, 0.0053, 0.0002, 0.0002, 0.0033, 0.0067, 0.0067 0]. With an exponential link function an expected index of 23.1810 is generated.

If the learned β parameters have been learned using response variables of progression free survival (in weeks, for example) than the index of 23.18 would indicate an estimated progression free survival of ~23 weeks for the tested patient.

Example 11: Generation of an Exemplary Oncogenic Index (Median Progression Free Survival Predictor)

In order to generate this exemplary index, the following calculations and algorithms are used:

$$OI = \sum_{i_{PDM}=1}^{N} \sum_{j_{FTR}=1}^{M} (|A_{i,j}| \cdot W_{i,j})$$

OI—Oncogenic Index (The median progressions free survival predictor)
 A—Normalized activation matrix between every PDM and every FTR.
 W—the weight matrix between every PDM and FTR. Machine learned (fitting of the obtained biological results and available clinical data).

This is one realization, as an example, of the Generalized Linear Model (GLM) described above. In this example, the link function used is the identity function (for simplicity) and the normalization of the measured activation levels include the absolute value operator.

For this example, the activation of the following set of PDMs and FTRs was determined.

The tested PDMs are EGFR L861Q and L858R. The tested FTRs are: JNK1, JNK2, ERK2, STAT3, P38b.
The resulting normalized activation levels are:
$A_{i,j} = $

|  | JNK2 | JNK1 | ERK2 | STAT3 | P38b |
|---|---|---|---|---|---|
| EGFR L861Q | 0.06 | 0.11 | 0.14 | 0.16 | 0.07 |
| EGFR L858R | 0.13 | 0 | 0.21 | 0.4 | 0.25 |

The results show that the EGFR gene harboring the L861Q mutation caused a normalized activation of: 0.06, 0.11, 0.14, 0.16, 0.07 in the FTRs: JNK2, JNK1, ERK2, STAT3, P38b, respectively. The results show that the EGFR gene harboring the L858R mutation caused a normalized activation of: 0.13, 0, 0.21, 0.4, 0.25 in the respective FTRs as determined by the methods disclosed herein.

The activation levels have been used to train the system in conjunction with a response variable of the median progression free survival observed for patients with these specific mutations. The resulting learned vector of parameters W is:
$W_{i,j} = $

|  | JNK2 | JNK1 | ERK2 | STAT3 | P38b |
|---|---|---|---|---|---|
| EGFR | 9.7 | 31.62 | 9.7 | 9.7 | 9.7 |

The thus obtained index (i.e. an index of the median progression free survival expected for the patient) indicates that:

The estimate for the median progression free survival expected for the patient carrying the L861Q mutation in the EGFR gene is 8.03 month. This value is comparable to a 8.1 month value observed in the art (Chiu, Chao-Hua, et al. (2015), Journal of Thoracic Oncology 10 793-799).

The estimate for the median progression free survival expected for the patient carrying the L858R mutation in the EGFR gene is 10.4 month. This value is comparable to a 10.8 month observed in the art (Rosell, Rafael, et al. (2012), The lancet oncology 13.3 (2012): 239-246).

Thus, the results presented herein indicate that oncogenic indexes generated by the methods and systems disclosed herein are sensitive and accurate and can indeed be used to provide a reliable assessment as to the degree of oncogenity of the tested mutations and of the condition of the patient in general and prognosis thereof.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of generating a curative index indicative of susceptibility to drug treatment of one or more patient specific mutations, comprising the steps of:
   a) forming an addressable array of a first set of expression constructs harboring genes comprising one or more patient specific mutations, and a second set of expression constructs of corresponding wild type genes;
   b) adding an expression vector encoding a Fluorescence Translocation Reporter (FTR) comprising a target gene portion linked to a specific reporter gene portion for each locus in the addressable array;
   c) adding viable assay cells to each locus under conditions enabling transfection of the expression constructs and expression vectors into the assay cells, wherein each assay cell co-expresses a gene comprising one or more patient specific mutations or its corresponding wild type gene, and an FTR;
   d) comparing the subcellular localization and/or translocation of the FTR in assay cells expressing the genes comprising the one or more mutations with assay cells expressing the corresponding wild type gene to identify a disparate result in the subcellular localization and/or translocation of the FTRs in the absence of a drug;
   e) determining the degree of subcellular translocation of the FTR in the assay cells expressing the gene comprising the one or more mutations and normalizing the result with respect to the degree of subcellular translocation of the FTR in the assay cells expressing the corresponding wild type gene, to obtain a normalized activation level of the one or more mutations in the absence of a drug;
   f) adding a drug to the assay cells and repeating step e), to obtain a normalized activation level of the one or more mutations in the presence of the drug; and
   g) analyzing a correlation between the normalized activation level of the one or more mutations in the presence of the drug, the normalized activation level of the one or more mutations in the absence of the drug, and a clinical outcome of response to treatment with the drug, wherein a correlation between the normalized activation level in the presence of the drug and response to treatment represents the curative index of the drug.

2. The method of claim 1, wherein the drug is an anticancer drug.

3. The method of claim 1, comprising adding more than one drug, concomitantly or sequentially and/or adding varying concentration of drug(s).

4. The method of claim 1, wherein the first and/or second sets of expression constructs comprise a double stranded linear DNA or wherein the promoter of the first and second set of expression constructs is an inducible or constitutive promoter.

5. The method of claim 1, wherein step c) precedes step a) and/or step b).

6. The method of claim 1, wherein analyzing comprises utilizing machine learning, correlation univariate analysis, multivariate analysis, support vector machine, generalized linear model or combinations thereof.

* * * * *